United States Patent [19]
Wilson et al.

[11] Patent Number: 6,057,119
[45] Date of Patent: May 2, 2000

[54] CRYSTAL STRUCTURE AND MUTANTS OF INTERLEUKIN-1β CONVERTING ENZYME

[75] Inventors: Keith P. Wilson, Hopkinton; James P. Griffith, Weston; Eunice E. Kim, Framingham; David J. Livingston, Newtonville, all of Mass.

[73] Assignee: Vertex Pharmaceuticals, Incorporated, Cambridge, Mass.

[21] Appl. No.: 08/450,362

[22] Filed: May 25, 1995

Related U.S. Application Data

[62] Division of application No. 08/261,582, Jun. 17, 1994, abandoned.

[51] Int. Cl.$^7$ ...................................................... C12Q 1/37
[52] U.S. Cl. .............................. 435/23; 435/24; 435/212; 435/219; 435/226
[58] Field of Search ..................................... 435/219, 212, 435/213, 214, 23, 24

[56] References Cited

U.S. PATENT DOCUMENTS 5,492,824  2/1996  Talanian et al. ......................... 435/226

OTHER PUBLICATIONS

Bryan, P.N., "Protein Engineering", *Biotech Adv.*, 5, pp. 221–234 (1987).

Campbell, I.D. and Dwek, R.A., "Diffraction", *Biol. Spect.*, Ch. 12, pp. 299–327 (1984).

Kajihara, A., et al., "Protein Modeling Using a Chimera Reference Protein Derived From Exons", *Protein Engineering*, 6, pp. 615–620 (1993).

Musil, D., et al., "The Refined 2.15 Å X–Ray Crystal Structure of Human Liver Cathepsin B: The Structural Basis for its Specificity", *EMBO J.*, 10, pp. 2321–2330 (1991).

Russell, A.J. and Fersht, A.R., "Rational Modification of Enzyme Catalysis by Engineering Surface Charge", *Nature*, 328, pp. 496–500 (1987).

Walker, N.P.C. et al., "Crystal Structure of the Cysteine Protease Interleukin–1β–Converting Enzyme: A (p20/p10)$_2$ Homodimer", *Cell.*, 78, pp. 343–352 (Jul., 1994).

Wilson, K.P., et al., "Structure and Mechanism of Interleukin–1β Convertig Enzyme", *Nature*, 370, pp. 270–275 (Jul., 1994).

Wright, C.S. et al., "Structure of Subtilisn BPN' at 2.5 Å Resolution", *Nature*, 221, pp. 235–242 (1969).

Sielecki, A.R. et al., "Structure of Recombinant Human Renin, a Target for Cardiovascular–Active Drugs, at 2.5 Å Resolution", *Science*, 243, pp. 1346–1351 (1989).

Thompson, J.A., et al., "In Vitro Folding and Autoprocessing of Active Interleukin–1β Converting Enzyme From an Inactive Recombinant Precursor", *J. Cell. Biochem. Keystone Symp. on Molec. & Cell. Biol.*, Supp. 18 D, p. 148, S 229 (Mar., 1994).

*Primary Examiner*—Robert A. Wax
*Assistant Examiner*—Nashaat T. Nashed
*Attorney, Agent, or Firm*—Fish & Neave; James F. Haley, Jr., Esq.; Lisa A. Dixon

[57] ABSTRACT

Interleukin-1β converting enzyme ("ICE") processes an inactive precursor to the pro-inflammatory cytokine, interleukin-1β. The high-resolution structure of human ICE crystallized in complex with an inhibitor is determined by X-ray diffraction. The active site spans both the 10 and 20 kilodalton subunits. The accessory binding site is composed of residues from the p10 and p20 subunits that are adjacent to the two-fold axis of the crystal. The structure coordinates of the enzyme may be used to design novel classes of ICE inhibitors.

7 Claims, 101 Drawing Sheets

(2 of 101 Drawing Sheet(s) Filed in Color)

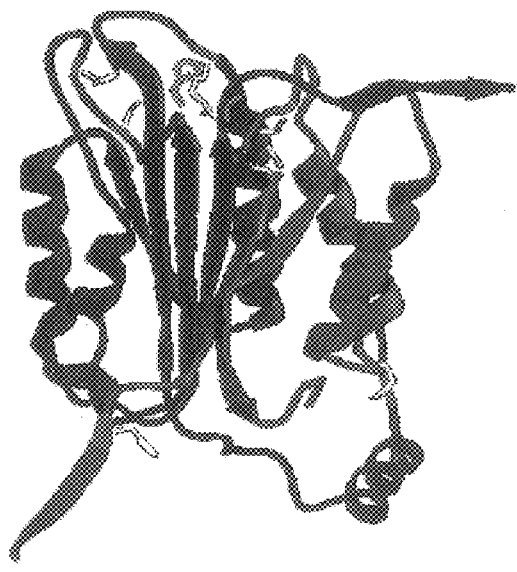 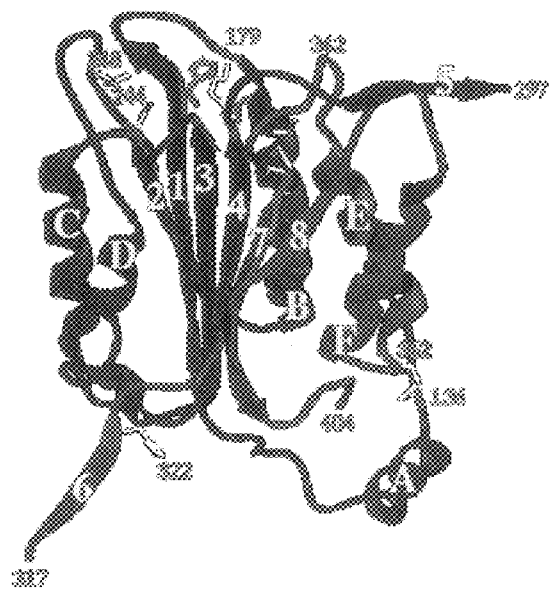
FIG. IA  FIG. IB

FIG. 4A

TETRAMER INTERFACE CONTACTS

| Residue | |
|---|---|
| P20 | P10 |
| 150 | 375 |
| 151 | 371 |
| 151 | 372 |
| 151 | 375 |
| 291 | 323 |
| 291 | 321 |
| 291 | 322 |
| 291 | 323 |
| 292 | 321 |
| 293 | 321 |
| 293 | 319 |
| 293 | 320 |
| 294 | 318 |
| 294 | 319 |
| 294 | 320 |
| 295 | 318 |
| 295 | 319 |
| 295 | 320 |
| 295 | 321 |
| 296 | 317 |
| 297 | 317 |

| Residue | |
|---|---|
| P10 | P10 |
| 320 | 382 |
| 320 | 380 |
| 322 | 377 |
| 322 | 378 |
| 322 | 380 |
| 322 | 384 |
| 322 | 385 |
| 322 | 386 |
| 323 | 327 |
| 324 | 334 |
| 324 | 386 |
| 325 | 378 |
| 325 | 386 |
| 334 | 393 |
| 335 | 391 |
| 367 | 367 |
| 367 | 374 |
| 371 | 394 |
| 371 | 395 |
| 371 | 396 |
| 374 | 392 |
| 374 | 393 |
| 374 | 394 |
| 375 | 395 |
| 375 | 396 |
| 378 | 395 |
| 378 | 396 |

| Residue | |
|---|---|
| P20 | P20 |
| 240 | 259 |
| 267 | 293 |
| 268 | 293 |
| 274 | 295 |

FIG. 4B

| 386 | 393 |
|-----|-----|
| 386 | 395 |
| 388 | 392 |
| 388 | 391 |
| 388 | 393 |
| 389 | 392 |
| 389 | 391 |
| 390 | 391 |

FIG. 5A

STRUCTURE COORDINATES OF ICE

| Atom | Atom Type | Residue | # | X | Y | Z | OCC | B |
|---|---|---|---|---|---|---|---|---|
| 1 | C | GLY | 131 | 49.848 | 81.525 | -9.909 | 1.00 | 66.26 |
| 2 | O | GLY | 131 | 50.205 | 82.686 | -9.789 | 1.00 | 67.80 |
| 3 | HT1 | GLY | 131 | 51.316 | 82.385 | -11.694 | 1.00 | 0.00 |
| 4 | HT2 | GLY | 131 | 49.746 | 82.510 | -12.180 | 1.00 | 0.00 |
| 5 | N | GLY | 131 | 50.546 | 81.841 | -12.148 | 1.00 | 71.76 |
| 6 | HT3 | GLY | 131 | 50.783 | 81.456 | -13.079 | 1.00 | 0.00 |
| 7 | CA | GLY | 131 | 50.192 | 80.805 | -11.207 | 1.00 | 65.90 |
| 8 | N | ASN | 132 | 49.175 | 80.916 | -8.934 | 1.00 | 63.34 |
| 9 | H | ASN | 132 | 48.640 | 80.121 | -9.141 | 1.00 | 0.00 |
| 10 | CA | ASN | 132 | 49.178 | 81.466 | -7.566 | 1.00 | 57.35 |
| 11 | CB | ASN | 132 | 47.778 | 81.260 | -6.979 | 1.00 | 63.76 |
| 12 | CG | ASN | 132 | 47.550 | 82.132 | -5.758 | 1.00 | 65.77 |
| 13 | OD1 | ASN | 132 | 48.228 | 83.107 | -5.487 | 1.00 | 65.21 |
| 14 | ND2 | ASN | 132 | 46.506 | 81.860 | -4.997 | 1.00 | 67.11 |
| 15 | HD21 | ASN | 132 | 45.919 | 81.109 | -5.228 | 1.00 | 0.00 |
| 16 | HD22 | ASN | 132 | 46.382 | 82.450 | -4.223 | 1.00 | 0.00 |
| 17 | C | ASN | 132 | 50.261 | 80.777 | -6.706 | 1.00 | 51.45 |
| 18 | O | ASN | 132 | 50.487 | 80.946 | -5.521 | 1.00 | 46.19 |
| 19 | N | VAL | 133 | 50.972 | 79.911 | -7.425 | 1.00 | 47.07 |
| 20 | H | VAL | 133 | 50.765 | 79.856 | -8.373 | 1.00 | 0.00 |
| 21 | CA | VAL | 133 | 52.081 | 79.094 | -6.973 | 1.00 | 42.45 |
| 22 | CB | VAL | 133 | 52.214 | 77.891 | -7.947 | 1.00 | 39.63 |
| 23 | CG1 | VAL | 133 | 53.342 | 76.953 | -7.538 | 1.00 | 39.92 |
| 24 | CG2 | VAL | 133 | 50.868 | 77.172 | -8.010 | 1.00 | 35.70 |
| 25 | C | VAL | 133 | 53.302 | 79.986 | -7.029 | 1.00 | 42.39 |
| 26 | O | VAL | 133 | 53.511 | 80.670 | -8.020 | 1.00 | 41.5 |
| 27 | N | LYS | 134 | 54.119 | 79.997 | -5.986 | 1.00 | 43.94 |
| 28 | NZ | LYS | 134 | 53.921 | 79.394 | -5.236 | 1.00 | 0.00 |

FIG. 5B

| Atom | Atom Type | Residue | # | X | Y | Z | OCC | B |
|---|---|---|---|---|---|---|---|---|
| 29 | CA | LYS | 134 | 55.301 | 80.832 | -5.918 | 1.00 | 43.48 |
| 30 | CB | LYS | 134 | 55.842 | 80.694 | -4.498 | 1.00 | 47.92 |
| 31 | CG | LYS | 134 | 57.200 | 81.347 | -4.244 | 1.00 | 58.49 |
| 32 | CD | LYS | 134 | 57.671 | 81.322 | -2.773 | 1.00 | 68.37 |
| 33 | CE | LYS | 134 | 56.793 | 82.161 | -1.815 | 1.00 | 73.02 |
| 34 | NZ | LYS | 134 | 57.422 | 82.316 | -0.513 | 1.00 | 74.14 |
| 35 | HZ1 | LYS | 134 | 58.339 | 82.793 | -0.625 | 1.00 | 0.00 |
| 36 | HZ2 | LYS | 134 | 57.568 | 81.376 | -0.092 | 1.00 | 0.00 |
| 37 | HZ3 | LYS | 134 | 56.805 | 82.880 | 0.105 | 1.00 | 0.00 |
| 38 | C | LYS | 134 | 56.311 | 80.428 | -6.979 | 1.00 | 43.98 |
| 39 | O | LYS | 134 | 56.604 | 79.261 | -7.186 | 1.00 | 40.75 |
| 40 | N | LEU | 135 | 56.897 | 81.384 | -7.698 | 1.00 | 45.99 |
| 41 | H | LEU | 135 | 56.807 | 82.326 | -7.445 | 1.00 | 0.00 |
| 42 | CA | LEU | 135 | 57.679 | 81.019 | -8.861 | 1.00 | 47.05 |
| 43 | CB | LEU | 135 | 57.569 | 82.064 | -9.970 | 1.00 | 47.39 |
| 44 | CG | LEU | 135 | 56.156 | 82.207 | -10.535 | 1.00 | 45.83 |
| 45 | CD1 | LEU | 135 | 56.210 | 83.182 | -11.700 | 1.00 | 50.59 |
| 46 | CD2 | LEU | 135 | 55.609 | 80.873 | -11.014 | 1.00 | 48.32 |
| 47 | C | LEU | 135 | 59.140 | 80.819 | -8.610 | 1.00 | 49.94 |
| 48 | O | LEU | 135 | 59.802 | 81.521 | -7.860 | 1.00 | 47.32 |
| 49 | N | CYS | 136 | 59.601 | 79.787 | -9.312 | 1.00 | 53.47 |
| 50 | H | CYS | 136 | 58.954 | 79.191 | -9.740 | 1.00 | 0.00 |
| 51 | CA | CYS | 136 | 61.014 | 79.522 | -9.495 | 1.00 | 57.62 |
| 52 | C | CYS | 136 | 61.688 | 80.552 | -10.387 | 1.00 | 60.29 |
| 53 | O | CYS | 136 | 61.471 | 80.621 | -11.594 | 1.00 | 62.12 |
| 54 | CB | CYS | 136 | 61.208 | 78.144 | -10.115 | 1.00 | 53.99 |
| 55 | SG | CYS | 136 | 61.894 | 76.980 | -8.918 | 1.00 | 58.70 |
| 56 | N | SER | 137 | 62.538 | 81.402 | -9.833 | 1.00 | 59.84 |
| 57 | H | SER | 137 | 62.572 | 81.519 | -8.858 | 1.00 | 0.00 |

FIG. 5C

| Atom | Atom Type | Residue | # | X | Y | Z | OCC | B |
|---|---|---|---|---|---|---|---|---|
| 58 | CA | SER | 137 | 63.390 | 82.210 | -10.667 | 1.00 | 62.00 |
| 59 | CB | SER | 137 | 64.149 | 83.158 | -9.766 | 1.00 | 65.68 |
| 60 | OG | SER | 137 | 63.234 | 83.655 | -8.792 | 1.00 | 75.16 |
| 61 | HG | SER | 137 | 62.492 | 84.111 | -9.205 | 1.00 | 0.00 |
| 62 | C | SER | 137 | 64.313 | 81.329 | -11.458 | 1.00 | 61.26 |
| 63 | O | SER | 137 | 64.602 | 80.202 | -11.086 | 1.00 | 62.99 |
| 64 | N | LEU | 138 | 64.823 | 81.792 | -12.585 | 1.00 | 61.53 |
| 65 | H | LEU | 138 | 64.686 | 82.728 | -12.829 | 1.00 | 0.00 |
| 66 | CA | LEU | 138 | 65.553 | 80.911 | -13.478 | 1.00 | 64.28 |
| 67 | CB | LEU | 138 | 65.884 | 81.695 | -14.748 | 1.00 | 63.19 |
| 68 | CG | LEU | 138 | 66.536 | 80.878 | -15.866 | 1.00 | 61.50 |
| 69 | CD1 | LEU | 138 | 65.823 | 79.540 | -16.097 | 1.00 | 62.16 |
| 70 | CD2 | LEU | 138 | 66.528 | 81.749 | -17.112 | 1.00 | 65.07 |
| 71 | C | LEU | 138 | 66.813 | 80.309 | -12.877 | 1.00 | 67.11 |
| 72 | O | LEU | 138 | 67.183 | 79.164 | -13.115 | 1.00 | 66.56 |
| 73 | N | GLU | 139 | 67.503 | 81.099 | -12.063 | 1.00 | 68.85 |
| 74 | H | GLU | 139 | 67.248 | 82.038 | -11.982 | 1.00 | 0.00 |
| 75 | CA | GLU | 139 | 68.645 | 80.591 | -11.330 | 1.00 | 71.48 |
| 76 | CB | GLU | 139 | 69.271 | 81.757 | -10.558 | 1.00 | 78.29 |
| 77 | CG | GLU | 139 | 68.277 | 82.677 | -9.821 | 1.00 | 89.52 |
| 78 | CD | GLU | 139 | 68.983 | 83.966 | -9.426 | 1.00 | 98.5 |
| 79 | OE1 | GLU | 139 | 68.705 | 85.009 | -10.033 | 1.00 | 99.9 |
| 80 | OE2 | GLU | 139 | 69.811 | 83.927 | -8.510 | 1.00 | 101.79 |
| 81 | C | GLU | 139 | 68.241 | 79.453 | -10.411 | 1.00 | 69.73 |
| 82 | O | GLU | 139 | 68.938 | 78.458 | -10.328 | 1.00 | 70.27 |
| 83 | N | GLU | 140 | 67.107 | 79.556 | -9.711 | 1.00 | 67.40 |
| 84 | H | GLU | 140 | 66.567 | 80.364 | -9.814 | 1.00 | 0.00 |
| 85 | CA | GLU | 140 | 66.616 | 78.489 | -8.849 | 1.00 | 66.30 |
| 86 | CB | GLU | 140 | 65.290 | 78.874 | -8.234 | 1.00 | 69.93 |

FIG. 5D

| Atom | Atom Type | Residue | # | X | Y | Z | OCC | B |
|---|---|---|---|---|---|---|---|---|
| 87 | CG | GLU | 140 | 65.411 | 80.248 | -7.577 | 1.00 | 79.22 |
| 88 | CD | GLU | 140 | 64.097 | 80.745 | -7.015 | 1.00 | 83.51 |
| 89 | OE1 | GLU | 140 | 63.207 | 79.947 | -6.716 | 1.00 | 86.55 |
| 90 | OE2 | GLU | 140 | 63.971 | 81.956 | -6.866 | 1.00 | 89.13 |
| 91 | C | GLU | 140 | 66.431 | 77.221 | -9.621 | 1.00 | 64.12 |
| 92 | O | GLU | 140 | 66.927 | 76.166 | -9.273 | 1.00 | 61.28 |
| 93 | N | ALA | 141 | 65.703 | 77.298 | -10.720 | 1.00 | 64.66 |
| 94 | H | ALA | 141 | 65.236 | 78.135 | -10.921 | 1.00 | 0.00 |
| 95 | CA | ALA | 141 | 65.611 | 76.153 | -11.604 | 1.00 | 68.98 |
| 96 | CB | ALA | 141 | 64.889 | 76.570 | -12.884 | 1.00 | 70.25 |
| 97 | C | ALA | 141 | 66.979 | 75.596 | -11.947 | 1.00 | 71.14 |
| 98 | O | ALA | 141 | 67.313 | 74.428 | -11.765 | 1.00 | 72.56 |
| 99 | N | GLN | 142 | 67.818 | 76.487 | -12.459 | 1.00 | 72.92 |
| 100 | OH | GLN | 142 | 67.532 | 77.424 | -12.537 | 1.00 | 0.00 |
| 101 | CA | GLN | 142 | 69.151 | 76.115 | -12.892 | 1.00 | 73.96 |
| 102 | CB | GLN | 142 | 69.866 | 77.409 | -13.316 | 1.00 | 77.97 |
| 103 | CG | GLN | 142 | 70.887 | 77.279 | -14.452 | 1.00 | 87.44 |
| 104 | CD | GLN | 142 | 70.264 | 76.716 | -15.714 | 1.00 | 92.53 |
| 105 | OE1 | GLN | 142 | 70.722 | 75.733 | -16.286 | 1.00 | 95.95 |
| 106 | NE2 | GLN | 142 | 69.200 | 77.287 | -16.242 | 1.00 | 93.80 |
| 107 | HE21 | GLN | 142 | 68.816 | 78.075 | -15.810 | 1.00 | 0.00 |
| 108 | HE22 | GLN | 142 | 68.852 | 76.862 | -17.056 | 1.00 | 0.00 |
| 109 | C | GLN | 142 | 69.900 | 75.373 | -11.802 | 1.00 | 71.44 |
| 110 | O | GLN | 142 | 70.472 | 74.312 | -12.010 | 1.00 | 69.41 |
| 111 | N | ARG | 143 | 69.911 | 75.911 | -10.590 | 1.00 | 70.71 |
| 112 | H | ARG | 143 | 69.467 | 76.774 | -10.440 | 1.00 | 0.00 |
| 113 | CA | ARG | 143 | 70.560 | 75.235 | -9.482 | 1.00 | 71.58 |
| 114 | CB | ARG | 143 | 70.398 | 76.011 | -8.169 | 1.00 | 66.09 |
| 115 | CG | ARG | 143 | 71.452 | 77.103 | -8.009 | 1.00 | 68.24 |

FIG. 5E

| Atom | Atom Type | Residue | # | X | Y | Z | OCC | B |
|---|---|---|---|---|---|---|---|---|
| 116 | CD | ARG | 143 | 71.260 | 77.893 | -6.715 | 1.00 | 67.96 |
| 117 | NE | ARG | 143 | 70.068 | 78.720 | -6.772 | 1.00 | 68.10 |
| 118 | HE | ARG | 143 | 69.189 | 78.300 | -6.871 | 1.00 | 0.00 |
| 119 | CZ | ARG | 143 | 70.158 | 80.048 | -6.694 | 1.00 | 68.46 |
| 120 | NH1 | ARG | 143 | 69.028 | 80.800 | -6.754 | 1.00 | 68.32 |
| 121 | HH11 | ARG | 143 | 68.137 | 80.358 | -6.858 | 1.00 | 0.00 |
| 122 | HH12 | ARG | 143 | 69.090 | 81.797 | -6.697 | 1.00 | 0.00 |
| 123 | NH2 | ARG | 143 | 71.365 | 80.664 | -6.550 | 1.00 | 68.45 |
| 124 | HH21 | ARG | 143 | 72.206 | 80.125 | -6.498 | 1.00 | 0.00 |
| 125 | HH22 | ARG | 143 | 71.412 | 81.661 | -6.490 | 1.00 | 0.00 |
| 126 | C | ARG | 143 | 70.013 | 73.850 | -9.263 | 1.00 | 73.97 |
| 127 | O | ARG | 143 | 70.765 | 72.907 | -9.074 | 1.00 | 77.08 |
| 128 | N | ILE | 144 | 68.696 | 73.662 | -9.285 | 1.00 | 73.91 |
| 129 | H | ILE | 144 | 68.105 | 74.411 | -9.519 | 1.00 | 0.00 |
| 130 | CA | ILE | 144 | 68.143 | 72.352 | -8.995 | 1.00 | 71.75 |
| 131 | CB | ILE | 144 | 66.605 | 72.394 | -8.986 | 1.00 | 69.05 |
| 132 | CG2 | ILE | 144 | 66.077 | 70.990 | -8.729 | 1.00 | 69.68 |
| 133 | CG1 | ILE | 144 | 66.084 | 73.314 | -7.895 | 1.00 | 65.22 |
| 134 | CD1 | ILE | 144 | 64.588 | 73.540 | -8.061 | 1.00 | 62.44 |
| 135 | C | ILE | 144 | 68.604 | 71.367 | -10.036 | 1.00 | 72.66 |
| 136 | O | ILE | 144 | 69.045 | 70.260 | -9.743 | 1.00 | 71.17 |
| 137 | N | TRP | 145 | 68.507 | 71.765 | -11.304 | 1.00 | 75.70 |
| 138 | H | TRP | 145 | 68.167 | 72.662 | -11.514 | 1.00 | 0.00 |
| 139 | CA | TRP | 145 | 68.929 | 70.861 | -12.351 | 1.00 | 83.94 |
| 140 | CB | TRP | 145 | 68.658 | 71.462 | -13.746 | 1.00 | 86.15 |
| 141 | CG | TRP | 145 | 69.038 | 70.460 | -14.839 | 1.00 | 93.70 |
| 142 | CD2 | TRP | 145 | 68.217 | 69.255 | -15.098 | 1.00 | 95.01 |
| 143 | CE2 | TRP | 145 | 69.056 | 68.711 | -16.236 | 1.00 | 96.30 |
| 144 | CE3 | TRP | 145 | 67.071 | 68.594 | -14.711 | 1.00 | 94.15 |

FIG. 5F

| Atom | Atom Type | Residue | # | X | Y | Z | OCC | B |
|---|---|---|---|---|---|---|---|---|
| 145 | CD1 | TRP | 145 | 70.133 | 70.564 | -15.670 | 1.00 | 95.29 |
| 146 | NE1 | TRP | 145 | 70.111 | 69.520 | -16.475 | 1.00 | 93.47 |
| 147 | HE1 | TRP | 145 | 70.787 | 69.359 | -17.166 | 1.00 | 0.00 |
| 148 | CZ2 | TRP | 145 | 68.642 | 67.562 | -16.873 | 1.00 | 100.90 |
| 149 | CZ3 | TRP | 145 | 66.717 | 67.444 | -15.394 | 1.00 | 96.37 |
| 150 | CH2 | TRP | 145 | 67.473 | 66.945 | -16.445 | 1.00 | 98.93 |
| 151 | C | TRP | 145 | 70.411 | 70.588 | -12.184 | 1.00 | 87.50 |
| 152 | O | TRP | 145 | 70.817 | 69.442 | -12.042 | 1.00 | 88.19 |
| 153 | N | ALA | 146 | 71.240 | 71.638 | -12.196 | 1.00 | 90.23 |
| 154 | H | ALA | 146 | 70.872 | 72.546 | -12.279 | 1.00 | 0.00 |
| 155 | CA | ALA | 146 | 72.678 | 71.479 | -12.055 | 1.00 | 90.96 |
| 156 | CB | ALA | 146 | 73.316 | 72.866 | -12.003 | 1.00 | 89.47 |
| 157 | C | ALA | 146 | 73.078 | 70.678 | -10.827 | 1.00 | 92.53 |
| 158 | O | ALA | 146 | 74.075 | 69.975 | -10.833 | 1.00 | 93.84 |
| 159 | N | GLN | 147 | 72.310 | 70.767 | -9.739 | 1.00 | 93.24 |
| 160 | H | GLN | 147 | 71.578 | 71.421 | -9.711 | 1.00 | 0.00 |
| 161 | CA | GLN | 147 | 72.543 | 69.925 | -8.583 | 1.00 | 94.09 |
| 162 | CB | GLN | 147 | 71.690 | 70.379 | -7.387 | 1.00 | 96.74 |
| 163 | CG | GLN | 147 | 72.033 | 69.642 | -6.090 | 1.00 | 102.36 |
| 164 | CD | GLN | 147 | 70.829 | 69.585 | -5.181 | 1.00 | 107.75 |
| 165 | OE1 | GLN | 147 | 69.729 | 70.018 | -5.491 | 1.00 | 109.80 |
| 166 | NE2 | GLN | 147 | 70.957 | 68.991 | -4.006 | 1.00 | 109.34 |
| 167 | HE21 | GLN | 147 | 71.821 | 68.602 | -3.760 | 1.00 | 0.00 |
| 168 | HE22 | GLN | 147 | 70.155 | 68.987 | -3.438 | 1.00 | 0.00 |
| 169 | C | GLN | 147 | 72.216 | 68.479 | -8.875 | 1.00 | 93.64 |
| 170 | O | GLN | 147 | 73.058 | 67.595 | -8.801 | 1.00 | 93.43 |
| 171 | N | LYS | 148 | 70.969 | 68.171 | -9.211 | 1.00 | 91.82 |
| 172 | H | LYS | 148 | 70.319 | 68.869 | -9.439 | 1.00 | 0.00 |
| 173 | CA | LYS | 148 | 70.621 | 66.770 | -9.239 | 1.00 | 89.79 |

FIG. 5G

| Atom | Atom Type | Residue | # | X | Y | Z | OCC | B |
|---|---|---|---|---|---|---|---|---|
| 174 | CB | LYS | 148 | 69.339 | 66.539 | -8.438 | 1.00 | 91.49 |
| 175 | CG | LYS | 148 | 69.449 | 66.861 | -6.954 | 1.00 | 91.59 |
| 176 | CD | LYS | 148 | 68.211 | 66.386 | -6.193 | 1.00 | 94.76 |
| 177 | CE | LYS | 148 | 68.288 | 66.715 | -4.706 | 1.00 | 97.17 |
| 178 | NZ | LYS | 148 | 69.521 | 66.190 | -4.145 | 1.00 | 102.16 |
| 179 | HZ1 | LYS | 148 | 70.339 | 66.615 | -4.627 | 1.00 | 0.00 |
| 180 | HZ2 | LYS | 148 | 69.553 | 65.158 | -4.275 | 1.00 | 0.00 |
| 181 | HZ3 | LYS | 148 | 69.574 | 66.411 | -3.131 | 1.00 | 0.00 |
| 182 | C | LYS | 148 | 70.457 | 66.096 | -10.578 | 1.00 | 87.23 |
| 183 | O | LYS | 148 | 70.294 | 64.882 | -10.625 | 1.00 | 88.22 |
| 184 | N | ALA | 149 | 70.496 | 66.825 | -11.691 | 1.00 | 83.64 |
| 185 | H | ALA | 149 | 70.728 | 67.775 | -11.599 | 1.00 | 0.00 |
| 186 | CA | ALA | 149 | 70.271 | 66.316 | -13.039 | 1.00 | 81.28 |
| 187 | CB | ALA | 149 | 71.416 | 66.848 | -13.906 | 1.00 | 80.46 |
| 188 | C | ALA | 149 | 70.092 | 64.807 | -13.272 | 1.00 | 80.23 |
| 189 | O | ALA | 149 | 69.034 | 64.377 | -13.709 | 1.00 | 81.20 |
| 190 | N | ALA | 150 | 71.079 | 63.939 | -13.002 | 1.00 | 77.26 |
| 191 | H | ALA | 150 | 71.903 | 64.290 | -12.604 | 1.00 | 0.00 |
| 192 | CA | ALA | 150 | 70.928 | 62.493 | -13.224 | 1.00 | 72.54 |
| 193 | CB | ALA | 150 | 72.254 | 61.803 | -12.872 | 1.00 | 71.93 |
| 194 | C | ALA | 150 | 69.786 | 61.803 | -12.458 | 1.00 | 67.17 |
| 195 | O | ALA | 150 | 69.332 | 60.728 | -12.832 | 1.00 | 64.24 |
| 196 | N | GLU | 151 | 69.298 | 62.391 | -11.366 | 1.00 | 58.90 |
| 197 | H | GLU | 151 | 69.693 | 63.225 | -11.031 | 1.00 | 0.00 |
| 198 | CA | GLU | 151 | 68.153 | 61.823 | -10.700 | 1.00 | 55.46 |
| 199 | CB | GLU | 151 | 68.612 | 61.333 | -9.316 | 1.00 | 60.03 |
| 200 | CG | GLU | 151 | 69.510 | 60.091 | -9.532 | 1.00 | 67.91 |
| 201 | CD | GLU | 151 | 69.733 | 59.292 | -8.259 | 1.00 | 72.08 |
| 202 | OE1 | GLU | 151 | 68.753 | 58.778 | -7.702 | 1.00 | 75.94 |

FIG. 5H

| Atom | Atom Type | Residue | # | X | Y | Z | OCC | B |
|---|---|---|---|---|---|---|---|---|
| 203 | OE2 | GLU | 151 | 70.887 | 59.159 | -7.846 | 1.00 | 70.44 |
| 204 | C | GLU | 151 | 66.966 | 62.759 | -10.610 | 1.00 | 49.03 |
| 205 | O | GLU | 151 | 66.237 | 62.811 | -9.632 | 1.00 | 40.75 |
| 206 | N | ILE | 152 | 66.751 | 63.538 | -11.671 | 1.00 | 46.24 |
| 207 | H | ILE | 152 | 67.390 | 63.525 | -12.419 | 1.00 | 0.00 |
| 208 | CA | ILE | 152 | 65.578 | 64.379 | -11.820 | 1.00 | 41.23 |
| 209 | CB | ILE | 152 | 66.006 | 65.876 | -11.979 | 1.00 | 41.97 |
| 210 | CG2 | ILE | 152 | 64.846 | 66.776 | -12.375 | 1.00 | 37.44 |
| 211 | CG1 | ILE | 152 | 66.456 | 66.419 | -10.633 | 1.00 | 39.50 |
| 212 | CD1 | ILE | 152 | 67.026 | 67.826 | -10.790 | 1.00 | 45.38 |
| 213 | C | ILE | 152 | 64.838 | 63.880 | -13.063 | 1.00 | 39.41 |
| 214 | O | ILE | 152 | 65.399 | 63.521 | -14.089 | 1.00 | 38.70 |
| 215 | N | TYR | 153 | 63.506 | 63.846 | -12.966 | 1.00 | 37.18 |
| 216 | H | TYR | 153 | 63.125 | 64.015 | -12.080 | 1.00 | 0.00 |
| 217 | CA | TYR | 153 | 62.606 | 63.601 | -14.098 | 1.00 | 34.02 |
| 218 | CB | TYR | 153 | 61.131 | 63.521 | -13.608 | 1.00 | 30.99 |
| 219 | CG | TYR | 153 | 60.815 | 62.157 | -13.006 | 1.00 | 28.21 |
| 220 | CD1 | TYR | 153 | 60.889 | 61.023 | -13.795 | 1.00 | 27.24 |
| 221 | CE1 | TYR | 153 | 60.661 | 59.769 | -13.266 | 1.00 | 25.65 |
| 222 | CD2 | TYR | 153 | 60.496 | 62.024 | -11.663 | 1.00 | 24.92 |
| 223 | CE2 | TYR | 153 | 60.266 | 60.774 | -11.126 | 1.00 | 20.91 |
| 224 | CZ | TYR | 153 | 60.352 | 59.657 | -11.934 | 1.00 | 24.92 |
| 225 | OH | TYR | 153 | 60.116 | 58.405 | -11.404 | 1.00 | 22.74 |
| 226 | HH | TYR | 153 | 59.896 | 58.542 | -10.481 | 1.00 | 0.00 |
| 227 | C | TYR | 153 | 62.734 | 64.754 | -15.092 | 1.00 | 31.41 |
| 228 | O | TYR | 153 | 62.545 | 65.895 | -14.708 | 1.00 | 30.52 |
| 229 | N | PRO | 154 | 63.045 | 64.585 | -16.332 | 1.00 | 29.09 |
| 230 | CD | PRO | 154 | 63.433 | 63.298 | -16.886 | 1.00 | 26.14 |
| 231 | CA | PRO | 154 | 63.119 | 65.685 | -17.300 | 1.00 | 26.59 |

FIG. 5I

| Atom | Atom Type | Residue | # | X | Y | Z | OCC | B |
|---|---|---|---|---|---|---|---|---|
| 232 | CB | PRO | 154 | 63.791 | 65.078 | -18.508 | 1.00 | 21.73 |
| 233 | CG | PRO | 154 | 63.408 | 63.614 | -18.383 | 1.00 | 26.66 |
| 234 | C | PRO | 154 | 61.782 | 66.309 | -17.627 | 1.00 | 27.17 |
| 235 | O | PRO | 154 | 60.763 | 65.693 | -17.860 | 1.00 | 30.28 |
| 236 | N | ILE | 155 | 61.791 | 67.620 | -17.645 | 1.00 | 27.49 |
| 237 | H | ILE | 155 | 62.636 | 68.068 | -17.453 | 1.00 | 0.00 |
| 238 | CA | ILE | 155 | 60.623 | 68.417 | -17.912 | 1.00 | 27.05 |
| 239 | CB | ILE | 155 | 60.810 | 69.687 | -17.067 | 1.00 | 27.13 |
| 240 | CG2 | ILE | 155 | 59.893 | 70.851 | -17.429 | 1.00 | 28.62 |
| 241 | CG1 | ILE | 155 | 60.584 | 69.235 | -15.624 | 1.00 | 27.98 |
| 242 | CD1 | ILE | 155 | 59.370 | 68.340 | -15.354 | 1.00 | 30.26 |
| 243 | C | ILE | 155 | 60.648 | 68.636 | -19.414 | 1.00 | 33.41 |
| 244 | O | ILE | 155 | 61.715 | 68.804 | -19.990 | 1.00 | 34.72 |
| 245 | N | MET | 156 | 59.510 | 68.638 | -20.116 | 1.00 | 33.95 |
| 246 | H | MET | 156 | 58.677 | 68.455 | -19.642 | 1.00 | 0.00 |
| 247 | CA | MET | 156 | 59.471 | 68.939 | -21.542 | 1.00 | 31.70 |
| 248 | CB | MET | 156 | 58.252 | 68.339 | -22.224 | 1.00 | 31.01 |
| 249 | CG | MET | 156 | 58.574 | 67.001 | -22.838 | 1.00 | 30.35 |
| 250 | SD | MET | 156 | 57.118 | 66.252 | -23.577 | 1.00 | 39.82 |
| 251 | CE | MET | 156 | 57.590 | 64.545 | -23.528 | 1.00 | 34.89 |
| 252 | C | MET | 156 | 59.384 | 70.434 | -21.735 | 1.00 | 34.78 |
| 253 | O | MET | 156 | 59.035 | 71.208 | -20.854 | 1.00 | 32.33 |
| 254 | N | ASP | 157 | 59.711 | 70.869 | -22.942 | 1.00 | 37.95 |
| 255 | H | ASP | 157 | 59.923 | 70.224 | -23.648 | 1.00 | 0.00 |
| 256 | CA | ASP | 157 | 59.715 | 72.281 | -23.240 | 1.00 | 38.36 |
| 257 | CB | ASP | 157 | 60.385 | 72.438 | -24.613 | 1.00 | 51.68 |
| 258 | CG | ASP | 157 | 60.369 | 73.848 | -25.178 | 1.00 | 61.42 |
| 259 | OD1 | ASP | 157 | 60.483 | 73.957 | -26.401 | 1.00 | 68.30 |
| 260 | OD2 | ASP | 157 | 60.249 | 74.822 | -24.421 | 1.00 | 67.14 |

FIG. 5J

| Atom | Atom Type | Residue | # | X | Y | Z | OCC | B |
|---|---|---|---|---|---|---|---|---|
| 261 | C | ASP | 157 | 58.315 | 72.829 | -23.203 | 1.00 | 31.15 |
| 262 | O | ASP | 157 | 57.360 | 72.284 | -23.730 | 1.00 | 27.50 |
| 263 | N | LYS | 158 | 58.232 | 73.965 | -22.543 | 1.00 | 30.63 |
| 264 | H | LYS | 158 | 59.032 | 74.318 | -22.102 | 1.00 | 0.00 |
| 265 | CA | LYS | 158 | 56.975 | 74.638 | -22.320 | 1.00 | 33.69 |
| 266 | CB | LYS | 158 | 57.265 | 75.906 | -21.540 | 1.00 | 34.01 |
| 267 | CG | LYS | 158 | 56.037 | 76.664 | -21.085 | 1.00 | 40.80 |
| 268 | CD | LYS | 158 | 56.390 | 77.826 | -20.154 | 1.00 | 48.58 |
| 269 | CE | LYS | 158 | 55.152 | 78.472 | -19.524 | 1.00 | 52.61 |
| 270 | NZ | LYS | 158 | 55.537 | 79.342 | -18.431 | 1.00 | 59.47 |
| 271 | HZ1 | LYS | 158 | 56.154 | 80.095 | -18.794 | 1.00 | 0.00 |
| 272 | HZ2 | LYS | 158 | 56.050 | 78.792 | -17.712 | 1.00 | 0.00 |
| 273 | HZ3 | LYS | 158 | 54.691 | 79.763 | -17.998 | 1.00 | 0.00 |
| 274 | C | LYS | 158 | 56.275 | 74.942 | -23.618 | 1.00 | 38.44 |
| 275 | O | LYS | 158 | 55.076 | 74.803 | -23.735 | 1.00 | 41.75 |
| 276 | N | SER | 159 | 56.962 | 75.367 | -24.672 | 1.00 | 41.20 |
| 277 | H | SER | 159 | 57.938 | 75.470 | -24.645 | 1.00 | 0.00 |
| 278 | CA | SER | 159 | 56.297 | 75.717 | -25.916 | 1.00 | 39.99 |
| 279 | CB | SER | 159 | 57.304 | 76.202 | -26.930 | 1.00 | 39.69 |
| 280 | OG | SER | 159 | 58.553 | 75.552 | -26.729 | 1.00 | 40.47 |
| 281 | HG | SER | 159 | 58.453 | 74.606 | -26.880 | 1.00 | 0.00 |
| 282 | C | SER | 159 | 55.543 | 74.590 | -26.548 | 1.00 | 40.83 |
| 283 | O | SER | 159 | 54.666 | 74.774 | -27.370 | 1.00 | 43.09 |
| 284 | N | SER | 160 | 55.886 | 73.373 | -26.184 | 1.00 | 43.73 |
| 285 | H | SER | 160 | 56.444 | 73.181 | -25.399 | 1.00 | 0.00 |
| 286 | CA | SER | 160 | 55.410 | 72.261 | -26.959 | 1.00 | 45.71 |
| 287 | CB | SER | 160 | 56.592 | 71.756 | -27.769 | 1.00 | 45.15 |
| 288 | OG | SER | 160 | 57.835 | 71.958 | -27.083 | 1.00 | 53.30 |
| 289 | HG | SER | 160 | 58.517 | 71.533 | -27.614 | 1.00 | 0.00 |

FIG. 5K

| Atom | Atom Type | Residue | # | X | Y | Z | OCC | B |
|---|---|---|---|---|---|---|---|---|
| 290 | C | SER | 160 | 54.800 | 71.154 | -26.121 | 1.00 | 45.78 |
| 291 | O | SER | 160 | 54.262 | 70.217 | -26.700 | 1.00 | 48.03 |
| 292 | N | ARG | 161 | 54.842 | 71.162 | -24.782 | 1.00 | 38.45 |
| 293 | H | ARG | 161 | 55.201 | 71.921 | -24.278 | 1.00 | 0.00 |
| 294 | CA | ARG | 161 | 54.322 | 70.004 | -24.097 | 1.00 | 32.89 |
| 295 | CB | ARG | 161 | 54.987 | 69.929 | -22.727 | 1.00 | 31.71 |
| 296 | CG | ARG | 161 | 54.631 | 71.054 | -21.769 | 1.00 | 29.23 |
| 297 | CD | ARG | 161 | 55.579 | 71.078 | -20.571 | 1.00 | 26.52 |
| 298 | NE | ARG | 161 | 55.148 | 72.182 | -19.760 | 1.00 | 23.86 |
| 299 | HE | ARG | 161 | 54.189 | 72.357 | -19.663 | 1.00 | 0.00 |
| 300 | CZ | ARG | 161 | 56.001 | 72.971 | -19.138 | 1.00 | 24.88 |
| 301 | NH1 | ARG | 161 | 55.486 | 74.036 | -18.477 | 1.00 | 23.22 |
| 302 | HH11 | ARG | 161 | 54.499 | 74.198 | -18.481 | 1.00 | 0.00 |
| 303 | HH12 | ARG | 161 | 56.093 | 74.673 | -18.006 | 1.00 | 0.00 |
| 304 | NH2 | ARG | 161 | 57.339 | 72.712 | -19.115 | 1.00 | 26.60 |
| 305 | HH21 | ARG | 161 | 57.703 | 71.901 | -19.572 | 1.00 | 0.00 |
| 306 | HH22 | ARG | 161 | 57.957 | 73.331 | -18.630 | 1.00 | 0.00 |
| 307 | C | ARG | 161 | 52.816 | 70.077 | -23.999 | 1.00 | 30.40 |
| 308 | O | ARG | 161 | 52.219 | 71.144 | -23.981 | 1.00 | 30.63 |
| 309 | N | THR | 162 | 52.134 | 68.955 | -23.937 | 1.00 | 25.20 |
| 310 | H | THR | 162 | 52.595 | 68.099 | -24.073 | 1.00 | 0.00 |
| 311 | CA | THR | 162 | 50.699 | 68.963 | -23.791 | 1.00 | 23.14 |
| 312 | CB | THR | 162 | 50.068 | 68.276 | -25.028 | 1.00 | 23.65 |
| 313 | OG1 | THR | 162 | 50.780 | 67.056 | -25.252 | 1.00 | 26.56 |
| 314 | HG1 | THR | 162 | 50.721 | 66.510 | -24.445 | 1.00 | 0.00 |
| 315 | CG2 | THR | 162 | 50.148 | 69.114 | -26.306 | 1.00 | 23.19 |
| 316 | C | THR | 162 | 50.373 | 68.219 | -22.510 | 1.00 | 25.37 |
| 317 | O | THR | 162 | 50.062 | 67.030 | -22.548 | 1.00 | 27.75 |
| 318 | N | ARG | 163 | 50.423 | 68.826 | -21.340 | 1.00 | 24.62 |

FIG. 5L

| Atom | Atom Type | Residue | # | X | Y | Z | OCC | B |
|---|---|---|---|---|---|---|---|---|
| 319 | H | ARG | 163 | 50.560 | 69.797 | -21.312 | 1.00 | 0.00 |
| 320 | CA | ARG | 163 | 50.174 | 68.133 | -20.077 | 1.00 | 24.12 |
| 321 | CB | ARG | 163 | 50.757 | 68.905 | -18.918 | 1.00 | 15.48 |
| 322 | CG | ARG | 163 | 52.227 | 68.612 | -18.793 | 1.00 | 17.34 |
| 323 | CD | ARG | 163 | 52.721 | 69.593 | -17.772 | 1.00 | 18.83 |
| 324 | NE | ARG | 163 | 54.136 | 69.427 | -17.669 | 1.00 | 24.11 |
| 325 | HE | ARG | 163 | 54.592 | 68.736 | -18.195 | 1.00 | 0.00 |
| 326 | CZ | ARG | 163 | 54.822 | 70.232 | -16.883 | 1.00 | 25.67 |
| 327 | NH1 | ARG | 163 | 56.160 | 70.051 | -16.807 | 1.00 | 34.46 |
| 328 | HH11 | ARG | 163 | 56.596 | 69.318 | -17.328 | 1.00 | 0.00 |
| 329 | HH12 | ARG | 163 | 56.710 | 70.634 | -16.209 | 1.00 | 0.00 |
| 330 | NH2 | ARG | 163 | 54.219 | 71.220 | -16.167 | 1.00 | 27.39 |
| 331 | HH21 | ARG | 163 | 53.229 | 71.357 | -16.223 | 1.00 | 0.00 |
| 332 | HH22 | ARG | 163 | 54.772 | 71.806 | -15.575 | 1.00 | 0.00 |
| 333 | C | ARG | 163 | 48.738 | 67.876 | -19.714 | 1.00 | 24.62 |
| 334 | O | ARG | 163 | 47.893 | 68.762 | -19.750 | 1.00 | 29.04 |
| 335 | N | LEU | 164 | 48.357 | 66.667 | -19.340 | 1.00 | 23.75 |
| 336 | H | LEU | 164 | 49.023 | 65.971 | -19.147 | 1.00 | 0.00 |
| 337 | CA | LEU | 164 | 46.944 | 66.455 | -19.043 | 1.00 | 24.57 |
| 338 | CB | LEU | 164 | 46.366 | 65.336 | -19.893 | 1.00 | 27.72 |
| 339 | CG | LEU | 164 | 45.556 | 65.607 | -21.165 | 1.00 | 28.04 |
| 340 | CD1 | LEU | 164 | 46.108 | 66.789 | -21.926 | 1.00 | 30.94 |
| 341 | CD2 | LEU | 164 | 45.573 | 64.331 | -22.006 | 1.00 | 27.16 |
| 342 | C | LEU | 164 | 46.774 | 66.047 | -17.612 | 1.00 | 23.76 |
| 343 | O | LEU | 164 | 47.607 | 65.281 | -17.142 | 1.00 | 22.71 |
| 344 | N | ALA | 165 | 45.733 | 66.505 | -16.907 | 1.00 | 21.51 |
| 345 | H | ALA | 165 | 45.124 | 67.175 | -17.292 | 1.00 | 0.00 |
| 346 | CA | ALA | 165 | 45.396 | 65.986 | -15.589 | 1.00 | 24.14 |
| 347 | CB | ALA | 165 | 45.687 | 67.006 | -14.488 | 1.00 | 21.16 |

FIG. 5M

| Atom | Atom Type | Residue | # | X | Y | Z | OCC | B |
|---|---|---|---|---|---|---|---|---|
| 348 | C | ALA | 165 | 43.924 | 65.668 | -15.543 | 1.00 | 24.40 |
| 349 | O | ALA | 165 | 43.162 | 66.279 | -16.279 | 1.00 | 25.81 |
| 350 | N | LEU | 166 | 43.495 | 64.730 | -14.699 | 1.00 | 24.86 |
| 351 | H | LEU | 166 | 44.143 | 64.282 | -14.114 | 1.00 | 0.00 |
| 352 | CA | LEU | 166 | 42.091 | 64.361 | -14.592 | 1.00 | 27.92 |
| 353 | CB | LEU | 166 | 41.914 | 62.948 | -15.196 | 1.00 | 23.03 |
| 354 | CG | LEU | 166 | 40.571 | 62.280 | -14.919 | 1.00 | 20.45 |
| 355 | CD1 | LEU | 166 | 39.446 | 62.990 | -15.658 | 1.00 | 14.43 |
| 356 | CD2 | LEU | 166 | 40.691 | 60.807 | -15.320 | 1.00 | 21.71 |
| 357 | C | LEU | 166 | 41.580 | 64.404 | -13.149 | 1.00 | 28.64 |
| 358 | O | LEU | 166 | 42.207 | 63.838 | -12.261 | 1.00 | 26.66 |
| 359 | N | ILE | 167 | 40.441 | 65.079 | -12.901 | 1.00 | 27.07 |
| 360 | H | ILE | 167 | 39.991 | 65.549 | -13.638 | 1.00 | 0.00 |
| 361 | CA | ILE | 167 | 39.802 | 65.137 | -11.600 | 1.00 | 21.18 |
| 362 | CB | ILE | 167 | 39.494 | 66.602 | -11.205 | 1.00 | 20.90 |
| 363 | CG2 | ILE | 167 | 38.719 | 66.663 | -9.893 | 1.00 | 21.77 |
| 364 | CG1 | ILE | 167 | 40.793 | 67.354 | -11.003 | 1.00 | 17.47 |
| 365 | CD1 | ILE | 167 | 40.499 | 68.753 | -10.522 | 1.00 | 17.98 |
| 366 | C | ILE | 167 | 38.513 | 64.358 | -11.684 | 1.00 | 24.82 |
| 367 | O | ILE | 167 | 37.634 | 64.653 | -12.493 | 1.00 | 23.12 |
| 368 | N | ILE | 168 | 38.333 | 63.328 | -10.865 | 1.00 | 25.26 |
| 369 | H | ILE | 168 | 39.066 | 63.004 | -10.297 | 1.00 | 0.00 |
| 370 | CA | ILE | 168 | 37.022 | 62.731 | -10.757 | 1.00 | 23.44 |
| 371 | CB | ILE | 168 | 37.119 | 61.228 | -11.076 | 1.00 | 23.97 |
| 372 | CG2 | ILE | 168 | 35.741 | 60.582 | -10.863 | 1.00 | 28.80 |
| 373 | CG1 | ILE | 168 | 37.581 | 61.030 | -12.546 | 1.00 | 22.39 |
| 374 | CD1 | ILE | 168 | 37.869 | 59.587 | -12.959 | 1.00 | 22.21 |
| 375 | C | ILE | 168 | 36.506 | 62.981 | -9.353 | 1.00 | 24.34 |
| 376 | O | ILE | 168 | 37.126 | 62.633 | -8.356 | 1.00 | 23.09 |

FIG. 5N

| Atom | Atom Type | Residue | # | X | Y | Z | OCC | B |
|---|---|---|---|---|---|---|---|---|
| 377 | N | CYS | 169 | 35.337 | 63.613 | -9.260 | 1.00 | 26.60 |
| 378 | H | CYS | 169 | 34.821 | 63.777 | -10.079 | 1.00 | 0.00 |
| 379 | CA | CYS | 169 | 34.765 | 64.030 | -7.986 | 1.00 | 27.82 |
| 380 | CB | CYS | 169 | 34.847 | 65.544 | -7.831 | 1.00 | 26.82 |
| 381 | SG | CYS | 169 | 34.147 | 66.177 | -6.282 | 1.00 | 31.50 |
| 382 | C | CYS | 169 | 33.323 | 63.629 | -7.866 | 1.00 | 28.36 |
| 383 | O | CYS | 169 | 32.520 | 63.950 | -8.735 | 1.00 | 25.83 |
| 384 | N | ASN | 170 | 32.948 | 62.918 | -6.803 | 1.00 | 27.23 |
| 385 | H | ASN | 170 | 33.617 | 62.683 | -6.124 | 1.00 | 0.00 |
| 386 | CA | ASN | 170 | 31.554 | 62.555 | -6.619 | 1.00 | 29.76 |
| 387 | CB | ASN | 170 | 31.372 | 61.071 | -6.286 | 1.00 | 26.22 |
| 388 | CG | ASN | 170 | 31.674 | 60.138 | -7.440 | 1.00 | 29.16 |
| 389 | OD1 | ASN | 170 | 31.709 | 60.485 | -8.614 | 1.00 | 32.47 |
| 390 | ND2 | ASN | 170 | 31.970 | 58.887 | -7.151 | 1.00 | 25.45 |
| 391 | HD21 | ASN | 170 | 32.015 | 58.569 | -6.216 | 1.00 | 0.00 |
| 392 | HD22 | ASN | 170 | 32.132 | 58.288 | -7.901 | 1.00 | 0.00 |
| 393 | C | ASN | 170 | 30.957 | 63.328 | -5.478 | 1.00 | 32.01 |
| 394 | O | ASN | 170 | 31.382 | 63.086 | -4.361 | 1.00 | 34.71 |
| 395 | N | GLU | 171 | 30.000 | 64.247 | -5.672 | 1.00 | 36.94 |
| 396 | H | GLU | 171 | 29.711 | 64.420 | -6.594 | 1.00 | 0.00 |
| 397 | CA | GLU | 171 | 29.301 | 64.905 | -4.558 | 1.00 | 39.76 |
| 398 | CB | GLU | 171 | 29.119 | 66.413 | -4.822 | 1.00 | 36.97 |
| 399 | CG | GLU | 171 | 28.418 | 67.084 | -3.634 | 1.00 | 43.98 |
| 400 | CD | GLU | 171 | 28.233 | 68.579 | -3.777 | 1.00 | 47.95 |
| 401 | OE1 | GLU | 171 | 28.302 | 69.095 | -4.890 | 1.00 | 53.49 |
| 402 | OE2 | GLU | 171 | 28.003 | 69.233 | -2.761 | 1.00 | 48.17 |
| 403 | C | GLU | 171 | 27.914 | 64.338 | -4.240 | 1.00 | 41.90 |
| 404 | O | GLU | 171 | 27.509 | 64.214 | -3.096 | 1.00 | 40.97 |
| 405 | N | GLU | 172 | 27.133 | 63.976 | -5.251 | 1.00 | 48.24 |

FIG. 50

| Atom | Atom Type | Residue | # | X | Y | Z | OCC | B |
|---|---|---|---|---|---|---|---|---|
| 406 | H | GLU | 172 | 27.505 | 63.929 | -6.159 | 1.00 | 0.00 |
| 407 | CA | GLU | 172 | 25.760 | 63.534 | -5.050 | 1.00 | 51.31 |
| 408 | CB | GLU | 172 | 24.802 | 64.170 | -6.061 | 1.00 | 55.01 |
| 409 | CG | GLU | 172 | 23.819 | 65.134 | -5.408 | 1.00 | 66.24 |
| 410 | CD | GLU | 172 | 24.170 | 66.580 | -5.699 | 1.00 | 74.35 |
| 411 | OE1 | GLU | 172 | 23.249 | 67.402 | -5.708 | 1.00 | 81.11 |
| 412 | OE2 | GLU | 172 | 25.342 | 66.893 | -5.911 | 1.00 | 76.04 |
| 413 | C | GLU | 172 | 25.676 | 62.035 | -5.242 | 1.00 | 49.78 |
| 414 | O | GLU | 172 | 26.092 | 61.501 | -6.266 | 1.00 | 46.42 |
| 415 | N | PHE | 173 | 25.125 | 61.338 | -4.250 | 1.00 | 49.39 |
| 416 | H | PHE | 173 | 24.695 | 61.780 | -3.485 | 1.00 | 0.00 |
| 417 | CA | PHE | 173 | 25.085 | 59.888 | -4.303 | 1.00 | 53.47 |
| 418 | CB | PHE | 173 | 25.878 | 59.313 | -3.142 | 1.00 | 50.77 |
| 419 | CG | PHE | 173 | 27.371 | 59.547 | -3.286 | 1.00 | 46.81 |
| 420 | CD1 | PHE | 173 | 28.173 | 58.521 | -3.768 | 1.00 | 40.36 |
| 421 | CD2 | PHE | 173 | 27.927 | 60.747 | -2.867 | 1.00 | 42.17 |
| 422 | CE1 | PHE | 173 | 29.535 | 58.684 | -3.778 | 1.00 | 37.00 |
| 423 | CE2 | PHE | 173 | 29.291 | 60.904 | -2.902 | 1.00 | 38.90 |
| 424 | CZ | PHE | 173 | 30.089 | 59.870 | -3.332 | 1.00 | 39.65 |
| 425 | C | PHE | 173 | 23.661 | 59.372 | -4.221 | 1.00 | 56.41 |
| 426 | O | PHE | 173 | 22.772 | 60.010 | -3.675 | 1.00 | 60.38 |
| 427 | N | ASP | 174 | 23.394 | 58.194 | -4.764 | 1.00 | 54.59 |
| 428 | H | ASP | 174 | 24.131 | 57.657 | -5.134 | 1.00 | 0.00 |
| 429 | CA | ASP | 174 | 22.044 | 57.658 | -4.745 | 1.00 | 53.81 |
| 430 | CB | ASP | 174 | 21.943 | 56.370 | -5.557 | 1.00 | 51.10 |
| 431 | CG | ASP | 174 | 22.091 | 56.666 | -7.030 | 1.00 | 53.87 |
| 432 | OD1 | ASP | 174 | 22.150 | 55.698 | -7.795 | 1.00 | 53.10 |
| 433 | OD2 | ASP | 174 | 22.148 | 57.850 | -7.408 | 1.00 | 53.80 |
| 434 | C | ASP | 174 | 21.500 | 57.347 | -3.370 | 1.00 | 56.79 |

FIG. 5P

| Atom | Atom Type | Residue | # | X | Y | Z | OCC | B |
|---|---|---|---|---|---|---|---|---|
| 435 | O | ASP | 174 | 20.317 | 57.447 | -3.086 | 1.00 | 60.64 |
| 436 | N | SER | 175 | 22.354 | 56.940 | -2.457 | 1.00 | 57.04 |
| 437 | H | SER | 175 | 23.312 | 57.026 | -2.628 | 1.00 | 0.00 |
| 438 | CA | SER | 175 | 21.856 | 56.461 | -1.185 | 1.00 | 56.82 |
| 439 | CB | SER | 175 | 22.007 | 54.938 | -1.152 | 1.00 | 53.73 |
| 440 | OG | SER | 175 | 21.821 | 54.307 | -2.423 | 1.00 | 50.93 |
| 441 | HG | SER | 175 | 22.453 | 54.685 | -3.041 | 1.00 | 0.00 |
| 442 | C | SER | 175 | 22.614 | 57.115 | -0.038 | 1.00 | 59.19 |
| 443 | O | SER | 175 | 22.050 | 57.584 | 0.945 | 1.00 | 63.80 |
| 444 | N | ILE | 176 | 23.949 | 57.172 | -0.133 | 1.00 | 57.13 |
| 445 | H | ILE | 176 | 24.384 | 56.889 | -0.963 | 1.00 | 0.00 |
| 446 | CA | ILE | 176 | 24.725 | 57.758 | 0.942 | 1.00 | 50.84 |
| 447 | CB | ILE | 176 | 26.167 | 57.155 | 0.920 | 1.00 | 52.16 |
| 448 | CG2 | ILE | 176 | 25.982 | 55.645 | 1.127 | 1.00 | 54.09 |
| 449 | CG1 | ILE | 176 | 26.947 | 57.381 | -0.375 | 1.00 | 51.82 |
| 450 | CD1 | ILE | 176 | 28.205 | 56.486 | -0.451 | 1.00 | 47.41 |
| 451 | C | ILE | 176 | 24.716 | 59.262 | 0.770 | 1.00 | 47.11 |
| 452 | O | ILE | 176 | 24.516 | 59.755 | -0.332 | 1.00 | 45.21 |
| 453 | N | PRO | 177 | 24.918 | 60.009 | 1.801 | 1.00 | 47.09 |
| 454 | CD | PRO | 177 | 25.067 | 59.502 | 3.162 | 1.00 | 46.36 |
| 455 | CA | PRO | 177 | 24.821 | 61.475 | 1.806 | 1.00 | 48.52 |
| 456 | CB | PRO | 177 | 24.733 | 61.862 | 3.280 | 1.00 | 45.72 |
| 457 | CG | PRO | 177 | 25.513 | 60.744 | 3.937 | 1.00 | 45.89 |
| 458 | C | PRO | 177 | 25.870 | 62.308 | 1.096 | 1.00 | 51.58 |
| 459 | O | PRO | 177 | 27.078 | 62.045 | 1.042 | 1.00 | 56.38 |
| 460 | N | ARG | 178 | 25.287 | 63.373 | 0.559 | 1.00 | 50.95 |
| 461 | H | ARG | 178 | 24.351 | 63.552 | 0.778 | 1.00 | 0.00 |
| 462 | CA | ARG | 178 | 25.959 | 64.288 | -0.328 | 1.00 | 52.24 |
| 463 | CB | ARG | 178 | 24.910 | 65.270 | -0.842 | 1.00 | 54.80 |

FIG. 5Q

| Atom | Atom Type | Residue | # | X | Y | Z | OCC | B |
|---|---|---|---|---|---|---|---|---|
| 464 | CG | ARG | 178 | 25.505 | 66.396 | -1.661 | 1.00 | 62.55 |
| 465 | CD | ARG | 178 | 24.484 | 67.300 | -2.273 | 1.00 | 67.32 |
| 466 | NE | ARG | 178 | 25.167 | 68.507 | -2.664 | 1.00 | 77.79 |
| 467 | HE | ARG | 178 | 26.144 | 68.522 | -2.727 | 1.00 | 0.00 |
| 468 | CZ | ARG | 178 | 24.473 | 69.607 | -2.918 | 1.00 | 85.85 |
| 469 | NH1 | ARG | 178 | 23.102 | 69.585 | -2.899 | 1.00 | 92.67 |
| 470 | HH11 | ARG | 178 | 22.609 | 68.736 | -2.708 | 1.00 | 0.00 |
| 471 | HH12 | ARG | 178 | 22.586 | 70.415 | -3.103 | 1.00 | 0.00 |
| 472 | NH2 | ARG | 178 | 25.133 | 70.773 | -3.165 | 1.00 | 90.17 |
| 473 | HH21 | ARG | 178 | 26.133 | 70.802 | -3.145 | 1.00 | 0.00 |
| 474 | HH22 | ARG | 178 | 24.609 | 71.605 | -3.354 | 1.00 | 0.00 |
| 475 | C | ARG | 178 | 27.133 | 65.020 | 0.280 | 1.00 | 49.82 |
| 476 | O | ARG | 178 | 27.078 | 65.589 | 1.354 | 1.00 | 51.03 |
| 477 | N | ARG | 179 | 28.243 | 65.007 | -0.439 | 1.00 | 47.03 |
| 478 | H | ARG | 179 | 28.218 | 64.607 | -1.336 | 1.00 | 0.00 |
| 479 | CA | ARG | 179 | 29.458 | 65.625 | 0.039 | 1.00 | 42.75 |
| 480 | CB | ARG | 179 | 30.625 | 64.919 | -0.632 | 1.00 | 42.27 |
| 481 | CG | ARG | 179 | 30.599 | 63.395 | -0.447 | 1.00 | 39.14 |
| 482 | CD | ARG | 179 | 31.759 | 62.682 | -1.159 | 1.00 | 40.61 |
| 483 | NE | ARG | 179 | 33.057 | 63.164 | -0.704 | 1.00 | 40.03 |
| 484 | HE | ARG | 179 | 33.387 | 62.869 | 0.169 | 1.00 | 0.00 |
| 485 | CZ | ARG | 179 | 33.827 | 63.996 | -1.427 | 1.00 | 40.60 |
| 486 | NH1 | ARG | 179 | 33.483 | 64.391 | -2.691 | 1.00 | 35.23 |
| 487 | HH11 | ARG | 179 | 32.630 | 64.073 | -3.103 | 1.00 | 0.00 |
| 488 | HH12 | ARG | 179 | 34.077 | 65.023 | -3.191 | 1.00 | 0.00 |
| 489 | NH2 | ARG | 179 | 34.965 | 64.483 | -0.859 | 1.00 | 35.40 |
| 490 | HH21 | ARG | 179 | 35.205 | 64.214 | 0.074 | 1.00 | 0.00 |
| 491 | HH22 | ARG | 179 | 35.562 | 65.100 | -1.370 | 1.00 | 0.00 |
| 492 | C | ARG | 179 | 29.512 | 67.124 | -0.198 | 1.00 | 44.55 |

FIG. 5R

| Atom | Atom Type | Residue | # | X | Y | Z | OCC | B |
|---|---|---|---|---|---|---|---|---|
| 493 | O | ARG | 179 | 30.215 | 67.684 | -1.034 | 1.00 | 44.42 |
| 494 | N | THR | 180 | 28.730 | 67.862 | 0.570 | 1.00 | 45.86 |
| 495 | H | THR | 180 | 28.063 | 67.420 | 1.138 | 1.00 | 0.00 |
| 496 | CA | THR | 180 | 28.816 | 69.308 | 0.548 | 1.00 | 46.36 |
| 497 | CB | THR | 180 | 27.770 | 69.840 | 1.532 | 1.00 | 50.60 |
| 498 | OG1 | THR | 180 | 26.517 | 69.456 | 0.968 | 1.00 | 54.63 |
| 499 | HG1 | THR | 180 | 25.800 | 69.689 | 1.568 | 1.00 | 0.00 |
| 500 | CG2 | THR | 180 | 27.792 | 71.351 | 1.735 | 1.00 | 53.13 |
| 501 | C | THR | 180 | 30.221 | 69.783 | 0.901 | 1.00 | 46.41 |
| 502 | O | THR | 180 | 30.882 | 69.285 | 1.807 | 1.00 | 47.93 |
| 503 | N | GLY | 181 | 30.713 | 70.783 | 0.171 | 1.00 | 46.30 |
| 504 | H | GLY | 181 | 30.090 | 71.312 | -0.350 | 1.00 | 0.00 |
| 505 | CA | GLY | 181 | 32.118 | 71.193 | 0.236 | 1.00 | 41.25 |
| 506 | C | GLY | 181 | 32.915 | 70.679 | -0.948 | 1.00 | 40.64 |
| 507 | O | GLY | 181 | 34.005 | 71.154 | -1.278 | 1.00 | 37.29 |
| 508 | N | ALA | 182 | 32.381 | 69.688 | -1.672 | 1.00 | 35.93 |
| 509 | H | ALA | 182 | 31.540 | 69.257 | -1.418 | 1.00 | 0.00 |
| 510 | CA | ALA | 182 | 33.136 | 69.171 | -2.785 | 1.00 | 39.67 |
| 511 | CB | ALA | 182 | 32.314 | 68.028 | -3.377 | 1.00 | 35.68 |
| 512 | C | ALA | 182 | 33.503 | 70.220 | -3.824 | 1.00 | 39.67 |
| 513 | O | ALA | 182 | 34.590 | 70.239 | -4.378 | 1.00 | 40.75 |
| 514 | N | GLU | 183 | 32.599 | 71.153 | -4.107 | 1.00 | 42.72 |
| 515 | H | GLU | 183 | 31.748 | 71.149 | -3.627 | 1.00 | 0.00 |
| 516 | CA | GLU | 183 | 32.824 | 72.180 | -5.108 | 1.00 | 40.12 |
| 517 | CB | GLU | 183 | 31.614 | 73.091 | -5.246 | 1.00 | 47.30 |
| 518 | CG | GLU | 183 | 31.637 | 73.914 | -6.544 | 1.00 | 63.74 |
| 519 | CD | GLU | 183 | 30.918 | 73.216 | -7.697 | 1.00 | 71.48 |
| 520 | OE1 | GLU | 183 | 30.272 | 73.920 | -8.481 | 1.00 | 78.62 |
| 521 | OE2 | GLU | 183 | 30.994 | 71.988 | -7.818 | 1.00 | 76.00 |

FIG. 5S

| Atom | Atom Type | Residue | # | X | Y | Z | OCC | B |
|---|---|---|---|---|---|---|---|---|
| 522 | C | GLU | 183 | 33.998 | 73.045 | -4.776 | 1.00 | 35.44 |
| 523 | O | GLU | 183 | 34.778 | 73.390 | -5.639 | 1.00 | 37.02 |
| 524 | N | VAL | 184 | 34.197 | 73.424 | -3.521 | 1.00 | 32.69 |
| 525 | H | VAL | 184 | 33.502 | 73.236 | -2.857 | 1.00 | 0.00 |
| 526 | CA | VAL | 184 | 35.437 | 74.093 | -3.114 | 1.00 | 32.56 |
| 527 | CB | VAL | 184 | 35.391 | 74.286 | -1.598 | 1.00 | 30.19 |
| 528 | CG1 | VAL | 184 | 36.568 | 75.090 | -1.054 | 1.00 | 28.08 |
| 529 | CG2 | VAL | 184 | 34.081 | 74.992 | -1.308 | 1.00 | 34.05 |
| 530 | C | VAL | 184 | 36.707 | 73.335 | -3.505 | 1.00 | 31.95 |
| 531 | O | VAL | 184 | 37.716 | 73.836 | -3.987 | 1.00 | 31.94 |
| 532 | N | ASP | 185 | 36.649 | 72.025 | -3.278 | 1.00 | 36.44 |
| 533 | H | ASP | 185 | 35.811 | 71.642 | -2.945 | 1.00 | 0.00 |
| 534 | CA | ASP | 185 | 37.768 | 71.151 | -3.586 | 1.00 | 32.53 |
| 535 | CB | ASP | 185 | 37.470 | 69.728 | -3.077 | 1.00 | 33.96 |
| 536 | CG | ASP | 185 | 37.375 | 69.592 | -1.539 | 1.00 | 35.35 |
| 537 | OD1 | ASP | 185 | 38.047 | 70.367 | -0.833 | 1.00 | 28.61 |
| 538 | OD2 | ASP | 185 | 36.635 | 68.705 | -1.082 | 1.00 | 32.20 |
| 539 | C | ASP | 185 | 38.020 | 71.139 | -5.059 | 1.00 | 30.28 |
| 540 | O | ASP | 185 | 39.161 | 71.233 | -5.493 | 1.00 | 29.51 |
| 541 | N | ILE | 186 | 36.956 | 71.032 | -5.849 | 1.00 | 29.28 |
| 542 | H | ILE | 186 | 36.070 | 70.902 | -5.447 | 1.00 | 0.00 |
| 543 | CA | ILE | 186 | 37.096 | 71.078 | -7.305 | 1.00 | 31.19 |
| 544 | CB | ILE | 186 | 35.728 | 70.861 | -8.016 | 1.00 | 31.31 |
| 545 | CG2 | ILE | 186 | 35.874 | 71.027 | -9.544 | 1.00 | 29.98 |
| 546 | CG1 | ILE | 186 | 35.212 | 69.446 | -7.688 | 1.00 | 33.52 |
| 547 | CD1 | ILE | 186 | 33.829 | 69.127 | -8.292 | 1.00 | 24.25 |
| 548 | C | ILE | 186 | 37.684 | 72.413 | -7.748 | 1.00 | 30.16 |
| 549 | O | ILE | 186 | 38.691 | 72.466 | -8.447 | 1.00 | 30.56 |
| 550 | N | THR | 187 | 37.132 | 73.560 | -7.388 | 1.00 | 27.47 |

FIG. 5T

| Atom | Atom Type | Residue | # | X | Y | Z | OCC | B |
|---|---|---|---|---|---|---|---|---|
| 551 | H | THR | 187 | 36.310 | 73.583 | -6.842 | 1.00 | 0.00 |
| 552 | CA | THR | 187 | 37.739 | 74.820 | -7.788 | 1.00 | 27.93 |
| 553 | CB | THR | 187 | 36.943 | 75.985 | -7.175 | 1.00 | 27.45 |
| 554 | OG1 | THR | 187 | 35.600 | 75.803 | -7.625 | 1.00 | 32.61 |
| 555 | HG1 | THR | 187 | 35.578 | 75.839 | -8.583 | 1.00 | 0.00 |
| 556 | CG2 | THR | 187 | 37.461 | 77.371 | -7.566 | 1.00 | 24.19 |
| 557 | C | THR | 187 | 39.193 | 74.935 | -7.395 | 1.00 | 28.16 |
| 558 | O | THR | 187 | 39.997 | 75.448 | -8.163 | 1.00 | 28.74 |
| 559 | N | GLY | 188 | 39.561 | 74.456 | -6.203 | 1.00 | 28.71 |
| 560 | H | GLY | 188 | 38.908 | 74.010 | -5.619 | 1.00 | 0.00 |
| 561 | CA | GLY | 188 | 40.932 | 74.607 | -5.753 | 1.00 | 25.69 |
| 562 | C | GLY | 188 | 41.872 | 73.681 | -6.483 | 1.00 | 27.48 |
| 563 | O | GLY | 188 | 42.983 | 74.024 | -6.871 | 1.00 | 28.61 |
| 564 | N | MET | 189 | 41.491 | 72.438 | -6.720 | 1.00 | 27.34 |
| 565 | H | MET | 189 | 40.618 | 72.115 | -6.415 | 1.00 | 0.00 |
| 566 | CA | MET | 189 | 42.405 | 71.582 | -7.426 | 1.00 | 25.62 |
| 567 | CB | MET | 189 | 42.016 | 70.117 | -7.218 | 1.00 | 31.58 |
| 568 | CG | MET | 189 | 42.445 | 69.542 | -5.843 | 1.00 | 37.74 |
| 569 | SD | MET | 189 | 44.201 | 69.754 | -5.409 | 1.00 | 37.50 |
| 570 | CE | MET | 189 | 44.983 | 68.533 | -6.417 | 1.00 | 38.22 |
| 571 | C | MET | 189 | 42.477 | 71.893 | -8.893 | 1.00 | 24.18 |
| 572 | O | MET | 189 | 43.559 | 71.814 | -9.460 | 1.00 | 27.99 |
| 573 | N | THR | 190 | 41.385 | 72.251 | -9.570 | 1.00 | 24.30 |
| 574 | H | THR | 190 | 40.494 | 72.204 | -9.158 | 1.00 | 0.00 |
| 575 | CA | THR | 190 | 41.446 | 72.677 | -10.959 | 1.00 | 23.16 |
| 576 | CB | THR | 190 | 40.030 | 73.023 | -11.453 | 1.00 | 23.46 |
| 577 | OG1 | THR | 190 | 39.259 | 71.861 | -11.228 | 1.00 | 23.54 |
| 578 | HG1 | THR | 190 | 38.355 | 72.025 | -11.500 | 1.00 | 0.00 |
| 579 | CG2 | THR | 190 | 39.922 | 73.321 | -12.943 | 1.00 | 19.04 |

FIG. 5U

| Atom | Atom Type | Residue | # | X | Y | Z | OCC | B |
|---|---|---|---|---|---|---|---|---|
| 580 | C | THR | 190 | 42.363 | 73.878 | -11.143 | 1.00 | 25.40 |
| 581 | O | THR | 190 | 43.255 | 73.913 | -11.989 | 1.00 | 25.28 |
| 582 | N | MET | 191 | 42.207 | 74.935 | -10.353 | 1.00 | 25.85 |
| 583 | H | MET | 191 | 41.531 | 74.956 | -9.640 | 1.00 | 0.00 |
| 584 | CA | MET | 191 | 43.092 | 76.058 | -10.563 | 1.00 | 26.80 |
| 585 | CB | MET | 191 | 42.618 | 77.263 | -9.731 | 1.00 | 31.82 |
| 586 | CG | MET | 191 | 41.203 | 77.811 | -10.021 | 1.00 | 30.18 |
| 587 | SD | MET | 191 | 40.720 | 77.816 | -11.767 | 1.00 | 42.05 |
| 588 | CE | MET | 191 | 42.005 | 78.898 | -12.322 | 1.00 | 40.61 |
| 589 | C | MET | 191 | 44.534 | 75.727 | -10.227 | 1.00 | 26.94 |
| 590 | O | MET | 191 | 45.439 | 76.102 | -10.949 | 1.00 | 28.00 |
| 591 | N | LEU | 192 | 44.841 | 75.015 | -9.139 | 1.00 | 25.81 |
| 592 | H | LEU | 192 | 44.141 | 74.785 | -8.487 | 1.00 | 0.00 |
| 593 | CA | LEU | 192 | 46.207 | 74.599 | -8.872 | 1.00 | 22.18 |
| 594 | CB | LEU | 192 | 46.226 | 73.695 | -7.637 | 1.00 | 19.29 |
| 595 | CG | LEU | 192 | 47.592 | 73.125 | -7.246 | 1.00 | 25.33 |
| 596 | CD1 | LEU | 192 | 48.470 | 74.276 | -6.797 | 1.00 | 25.29 |
| 597 | CD2 | LEU | 192 | 47.450 | 72.049 | -6.153 | 1.00 | 25.35 |
| 598 | C | LEU | 192 | 46.798 | 73.872 | -10.049 | 1.00 | 19.90 |
| 599 | O | LEU | 192 | 47.871 | 74.187 | -10.546 | 1.00 | 19.35 |
| 600 | N | LEU | 193 | 46.115 | 72.857 | -10.554 | 1.00 | 20.99 |
| 601 | H | LEU | 193 | 45.208 | 72.654 | -10.237 | 1.00 | 0.00 |
| 602 | CA | LEU | 193 | 46.743 | 72.049 | -11.571 | 1.00 | 21.52 |
| 603 | CB | LEU | 193 | 45.920 | 70.802 | -11.849 | 1.00 | 21.31 |
| 604 | CG | LEU | 193 | 46.081 | 69.749 | -10.749 | 1.00 | 23.69 |
| 605 | CD1 | LEU | 193 | 45.125 | 68.587 | -11.000 | 1.00 | 26.09 |
| 606 | CD2 | LEU | 193 | 47.509 | 69.236 | -10.751 | 1.00 | 24.27 |
| 607 | C | LEU | 193 | 46.921 | 72.815 | -12.844 | 1.00 | 25.18 |
| 608 | O | LEU | 193 | 47.962 | 72.768 | -13.484 | 1.00 | 25.97 |

FIG. 5V

| Atom | Atom Type | Residue | # | X | Y | Z | OCC | B |
|---|---|---|---|---|---|---|---|---|
| 609 | N | GLN | 194 | 45.909 | 73.565 | -13.262 | 1.00 | 27.74 |
| 610 | H | GLN | 194 | 45.038 | 73.515 | -12.809 | 1.00 | 0.00 |
| 611 | CA | GLN | 194 | 46.071 | 74.455 | -14.391 | 1.00 | 29.82 |
| 612 | CB | GLN | 194 | 44.769 | 75.244 | -14.530 | 1.00 | 28.29 |
| 613 | CG | GLN | 194 | 44.400 | 75.460 | -15.983 | 1.00 | 33.28 |
| 614 | CD | GLN | 194 | 42.994 | 75.954 | -16.101 | 1.00 | 34.79 |
| 615 | OE1 | GLN | 194 | 42.085 | 75.270 | -16.546 | 1.00 | 33.62 |
| 616 | NE2 | GLN | 194 | 42.733 | 77.202 | -15.779 | 1.00 | 36.58 |
| 617 | HE21 | GLN | 194 | 43.468 | 77.783 | -15.495 | 1.00 | 0.00 |
| 618 | HE22 | GLN | 194 | 41.799 | 77.487 | -15.861 | 1.00 | 0.00 |
| 619 | C | GLN | 194 | 47.281 | 75.347 | -14.146 | 1.00 | 31.33 |
| 620 | O | GLN | 194 | 48.177 | 75.481 | -14.964 | 1.00 | 31.54 |
| 621 | N | ASN | 195 | 47.356 | 75.986 | -12.990 | 1.00 | 33.01 |
| 622 | H | ASN | 195 | 46.613 | 75.928 | -12.354 | 1.00 | 0.00 |
| 623 | CA | ASN | 195 | 48.530 | 76.762 | -12.606 | 1.00 | 30.77 |
| 624 | CB | ASN | 195 | 48.460 | 77.239 | -11.151 | 1.00 | 34.88 |
| 625 | CG | ASN | 195 | 47.691 | 78.525 | -10.957 | 1.00 | 38.35 |
| 626 | OD1 | ASN | 195 | 47.679 | 79.452 | -11.753 | 1.00 | 43.57 |
| 627 | ND2 | ASN | 195 | 47.015 | 78.668 | -9.836 | 1.00 | 36.28 |
| 628 | HD21 | ASN | 195 | 47.044 | 77.925 | -9.206 | 1.00 | 0.00 |
| 629 | HD22 | ASN | 195 | 46.506 | 79.497 | -9.715 | 1.00 | 0.00 |
| 630 | C | ASN | 195 | 49.860 | 76.066 | -12.719 | 1.00 | 28.51 |
| 631 | O | ASN | 195 | 50.871 | 76.696 | -12.949 | 1.00 | 26.10 |
| 632 | N | LEU | 196 | 49.928 | 74.758 | -12.542 | 1.00 | 27.38 |
| 633 | H | LEU | 196 | 49.112 | 74.264 | -12.313 | 1.00 | 0.00 |
| 634 | CA | LEU | 196 | 51.193 | 74.051 | -12.683 | 1.00 | 25.33 |
| 635 | CB | LEU | 196 | 51.179 | 72.795 | -11.806 | 1.00 | 24.19 |
| 636 | CG | LEU | 196 | 51.188 | 73.150 | -10.326 | 1.00 | 23.30 |
| 637 | CD1 | LEU | 196 | 50.972 | 71.914 | -9.481 | 1.00 | 24.60 |

FIG. 5W

| Atom | Atom Type | Residue | # | X | Y | Z | OCC | B |
|---|---|---|---|---|---|---|---|---|
| 638 | CD2 | LEU | 196 | 52.519 | 73.794 | -9.985 | 1.00 | 31.63 |
| 639 | C | LEU | 196 | 51.433 | 73.661 | -14.123 | 1.00 | 26.23 |
| 640 | O | LEU | 196 | 52.442 | 73.078 | -14.503 | 1.00 | 24.03 |
| 641 | N | GLY | 197 | 50.478 | 73.970 | -14.993 | 1.00 | 27.17 |
| 642 | H | GLY | 197 | 49.631 | 74.363 | -14.695 | 1.00 | 0.00 |
| 643 | CA | GLY | 197 | 50.704 | 73.779 | -16.401 | 1.00 | 25.75 |
| 644 | C | GLY | 197 | 49.860 | 72.707 | -17.015 | 1.00 | 26.04 |
| 645 | O | GLY | 197 | 50.142 | 72.320 | -18.140 | 1.00 | 27.75 |
| 646 | N | TYR | 198 | 48.830 | 72.188 | -16.360 | 1.00 | 24.74 |
| 647 | H | TYR | 198 | 48.531 | 72.597 | -15.518 | 1.00 | 0.00 |
| 648 | CA | TYR | 198 | 48.125 | 71.016 | -16.872 | 1.00 | 24.17 |
| 649 | CB | TYR | 198 | 47.870 | 69.968 | -15.744 | 1.00 | 24.44 |
| 650 | CG | TYR | 198 | 49.145 | 69.319 | -15.195 | 1.00 | 17.56 |
| 651 | CD1 | TYR | 198 | 49.919 | 69.969 | -14.251 | 1.00 | 17.53 |
| 652 | CE1 | TYR | 198 | 51.123 | 69.433 | -13.835 | 1.00 | 19.28 |
| 653 | CD2 | TYR | 198 | 49.572 | 68.117 | -15.711 | 1.00 | 16.54 |
| 654 | CE2 | TYR | 198 | 50.771 | 67.572 | -15.298 | 1.00 | 17.99 |
| 655 | CZ | TYR | 198 | 51.567 | 68.265 | -14.399 | 1.00 | 22.77 |
| 656 | OH | TYR | 198 | 52.806 | 67.774 | -14.022 | 1.00 | 26.91 |
| 657 | HH | TYR | 198 | 53.179 | 68.383 | -13.376 | 1.00 | 0.00 |
| 658 | C | TYR | 198 | 46.794 | 71.385 | -17.465 | 1.00 | 25.30 |
| 659 | O | TYR | 198 | 46.136 | 72.288 | -16.959 | 1.00 | 28.39 |
| 660 | N | SER | 199 | 46.353 | 70.714 | -18.533 | 1.00 | 27.93 |
| 661 | H | SER | 199 | 46.951 | 70.163 | -19.092 | 1.00 | 0.00 |
| 662 | CA | SER | 199 | 44.953 | 70.775 | -18.924 | 1.00 | 29.13 |
| 663 | CB | SER | 199 | 44.776 | 70.400 | -20.402 | 1.00 | 31.52 |
| 664 | OG | SER | 199 | 45.617 | 71.216 | -21.197 | 1.00 | 44.44 |
| 665 | HG | SER | 199 | 45.356 | 72.131 | -21.040 | 1.00 | 0.00 |
| 666 | C | SER | 199 | 44.163 | 69.810 | -18.077 | 1.00 | 25.88 |

FIG. 5X

| Atom | Atom Type | Residue | # | X | Y | Z | OCC | B |
|---|---|---|---|---|---|---|---|---|
| 667 | O | SER | 199 | 44.489 | 68.636 | -17.967 | 1.00 | 28.99 |
| 668 | N | VAL | 200 | 43.095 | 70.325 | -17.471 | 1.00 | 22.17 |
| 669 | H | VAL | 200 | 42.823 | 71.240 | -17.708 | 1.00 | 0.00 |
| 670 | CA | VAL | 200 | 42.321 | 69.612 | -16.481 | 1.00 | 21.46 |
| 671 | CB | VAL | 200 | 42.090 | 70.526 | -15.284 | 1.00 | 17.18 |
| 672 | CG1 | VAL | 200 | 41.528 | 69.691 | -14.142 | 1.00 | 19.27 |
| 673 | CG2 | VAL | 200 | 43.399 | 71.222 | -14.885 | 1.00 | 17.36 |
| 674 | C | VAL | 200 | 40.978 | 69.116 | -16.979 | 1.00 | 25.60 |
| 675 | O | VAL | 200 | 40.073 | 69.889 | -17.248 | 1.00 | 26.95 |
| 676 | N | ASP | 201 | 40.787 | 67.815 | -17.115 | 1.00 | 25.10 |
| 677 | H | ASP | 201 | 41.548 | 67.209 | -17.020 | 1.00 | 0.00 |
| 678 | CA | ASP | 201 | 39.459 | 67.259 | -17.292 | 1.00 | 26.46 |
| 679 | CB | ASP | 201 | 39.501 | 65.852 | -17.808 | 1.00 | 32.29 |
| 680 | CG | ASP | 201 | 39.387 | 65.818 | -19.271 | 1.00 | 40.02 |
| 681 | OD1 | ASP | 201 | 38.413 | 65.246 | -19.737 | 1.00 | 53.36 |
| 682 | OD2 | ASP | 201 | 40.251 | 66.358 | -19.949 | 1.00 | 48.96 |
| 683 | C | ASP | 201 | 38.786 | 67.159 | -15.940 | 1.00 | 28.68 |
| 684 | O | ASP | 201 | 39.402 | 66.593 | -15.030 | 1.00 | 25.09 |
| 685 | N | VAL | 202 | 37.561 | 67.665 | -15.755 | 1.00 | 26.15 |
| 686 | H | VAL | 202 | 37.092 | 68.158 | -16.463 | 1.00 | 0.00 |
| 687 | CA | VAL | 202 | 36.820 | 67.390 | -14.543 | 1.00 | 29.60 |
| 688 | CB | VAL | 202 | 36.274 | 68.690 | -13.955 | 1.00 | 29.43 |
| 689 | CG1 | VAL | 202 | 35.461 | 68.387 | -12.696 | 1.00 | 26.97 |
| 690 | CG2 | VAL | 202 | 37.434 | 69.634 | -13.649 | 1.00 | 26.15 |
| 691 | C | VAL | 202 | 35.669 | 66.447 | -14.865 | 1.00 | 33.37 |
| 692 | O | VAL | 202 | 34.893 | 66.731 | -15.763 | 1.00 | 36.29 |
| 693 | N | LYS | 203 | 35.496 | 65.309 | -14.183 | 1.00 | 33.12 |
| 694 | H | LYS | 203 | 36.163 | 65.050 | -13.508 | 1.00 | 0.00 |
| 695 | CA | LYS | 203 | 34.334 | 64.448 | -14.372 | 1.00 | 28.52 |

FIG. 5Y

| Atom | Atom Type | Residue | # | X | Y | Z | OCC | B |
|---|---|---|---|---|---|---|---|---|
| 696 | CB | LYS | 203 | 34.749 | 63.050 | -14.826 | 1.00 | 28.62 |
| 697 | CG | LYS | 203 | 35.590 | 62.990 | -16.088 | 1.00 | 32.11 |
| 698 | CD | LYS | 203 | 34.746 | 63.437 | -17.266 | 1.00 | 40.39 |
| 699 | CE | LYS | 203 | 35.531 | 63.532 | -18.574 | 1.00 | 50.57 |
| 700 | NZ | LYS | 203 | 34.651 | 64.012 | -19.625 | 1.00 | 59.39 |
| 701 | HZ1 | LYS | 203 | 34.274 | 64.946 | -19.364 | 1.00 | 0.00 |
| 702 | HZ2 | LYS | 203 | 33.854 | 63.352 | -19.738 | 1.00 | 0.00 |
| 703 | HZ3 | LYS | 203 | 35.168 | 64.088 | -20.524 | 1.00 | 0.00 |
| 704 | C | LYS | 203 | 33.596 | 64.313 | -13.046 | 1.00 | 29.68 |
| 705 | O | LYS | 203 | 34.220 | 64.117 | -12.016 | 1.00 | 30.93 |
| 706 | N | LYS | 204 | 32.268 | 64.402 | -12.954 | 1.00 | 32.55 |
| 707 | H | LYS | 204 | 31.711 | 64.391 | -13.762 | 1.00 | 0.00 |
| 708 | CA | LYS | 204 | 31.610 | 64.417 | -11.655 | 1.00 | 34.17 |
| 709 | CB | LYS | 204 | 30.827 | 65.701 | -11.363 | 1.00 | 32.07 |
| 710 | CG | LYS | 204 | 31.646 | 66.950 | -11.553 | 1.00 | 37.18 |
| 711 | CD | LYS | 204 | 30.858 | 68.196 | -11.188 | 1.00 | 44.8 |
| 712 | CE | LYS | 204 | 31.660 | 69.462 | -11.544 | 1.00 | 54.50 |
| 713 | NZ | LYS | 204 | 30.997 | 70.674 | -11.086 | 1.00 | 60.66 |
| 714 | HZ1 | LYS | 204 | 30.884 | 70.631 | -10.052 | 1.00 | 0.00 |
| 715 | HZ2 | LYS | 204 | 30.058 | 70.742 | -11.528 | 1.00 | 0.00 |
| 716 | HZ3 | LYS | 204 | 31.568 | 71.505 | -11.339 | 1.00 | 0.00 |
| 717 | C | LYS | 204 | 30.603 | 63.311 | -11.602 | 1.00 | 32.66 |
| 718 | O | LYS | 204 | 30.073 | 62.894 | -12.625 | 1.00 | 33.79 |
| 719 | N | ASN | 205 | 30.378 | 62.866 | -10.365 | 1.00 | 31.17 |
| 720 | H | ASN | 205 | 30.983 | 63.186 | -9.659 | 1.00 | 0.00 |
| 721 | CA | ASN | 205 | 29.340 | 61.902 | -10.003 | 1.00 | 29.81 |
| 722 | CB | ASN | 205 | 27.956 | 62.531 | -10.122 | 1.00 | 25.29 |
| 723 | CG | ASN | 205 | 27.915 | 63.623 | -9.103 | 1.00 | 26.48 |
| 724 | OD1 | ASN | 205 | 28.416 | 63.536 | -7.988 | 1.00 | 29.97 |

FIG. 5Z

| Atom | Atom Type | Residue | # | X | Y | Z | OCC | B |
|---|---|---|---|---|---|---|---|---|
| 725 | ND2 | ASN | 205 | 27.363 | 64.768 | -9.456 | 1.00 | 29.11 |
| 726 | HD21 | ASN | 205 | 27.014 | 64.830 | -10.369 | 1.00 | 0.00 |
| 727 | HD22 | ASN | 205 | 27.318 | 65.493 | -8.798 | 1.00 | 0.00 |
| 728 | C | ASN | 205 | 29.323 | 60.626 | -10.792 | 1.00 | 30.34 |
| 729 | O | ASN | 205 | 28.356 | 60.317 | -11.453 | 1.00 | 32.35 |
| 730 | N | LEU | 206 | 30.354 | 59.799 | -10.793 | 1.00 | 31.19 |
| 731 | H | LEU | 206 | 31.092 | 59.947 | -10.163 | 1.00 | 0.00 |
| 732 | CA | LEU | 206 | 30.352 | 58.667 | -11.698 | 1.00 | 28.61 |
| 733 | CB | LEU | 206 | 31.657 | 58.587 | -12.498 | 1.00 | 29.20 |
| 734 | CG | LEU | 206 | 32.070 | 59.852 | -13.281 | 1.00 | 29.46 |
| 735 | CD1 | LEU | 206 | 33.375 | 59.557 | -14.009 | 1.00 | 30.38 |
| 736 | CD2 | LEU | 206 | 31.010 | 60.255 | -14.297 | 1.00 | 33.07 |
| 737 | C | LEU | 206 | 30.196 | 57.402 | -10.933 | 1.00 | 30.76 |
| 738 | O | LEU | 206 | 30.211 | 57.314 | -9.715 | 1.00 | 35.60 |
| 739 | N | THR | 207 | 30.043 | 56.331 | -11.664 | 1.00 | 32.87 |
| 740 | H | THR | 207 | 29.939 | 56.423 | -12.631 | 1.00 | 0.00 |
| 741 | CA | THR | 207 | 30.012 | 55.027 | -11.058 | 1.00 | 36.34 |
| 742 | CB | THR | 207 | 28.851 | 54.344 | -11.773 | 1.00 | 36.91 |
| 743 | OG1 | THR | 207 | 27.728 | 54.701 | -10.986 | 1.00 | 42.24 |
| 744 | HG1 | THR | 207 | 26.926 | 54.355 | -11.394 | 1.00 | 0.00 |
| 745 | CG2 | THR | 207 | 28.942 | 52.841 | -11.905 | 1.00 | 42.72 |
| 746 | C | THR | 207 | 31.381 | 54.358 | -11.219 | 1.00 | 36.64 |
| 747 | O | THR | 207 | 32.157 | 54.742 | -12.079 | 1.00 | 39.32 |
| 748 | N | ALA | 208 | 31.747 | 53.344 | -10.429 | 1.00 | 36.10 |
| 749 | H | ALA | 208 | 31.129 | 53.028 | -9.745 | 1.00 | 0.00 |
| 750 | CA | ALA | 208 | 33.047 | 52.699 | -10.537 | 1.00 | 34.66 |
| 751 | CB | ALA | 208 | 33.042 | 51.453 | -9.643 | 1.00 | 32.92 |
| 752 | C | ALA | 208 | 33.402 | 52.325 | -11.959 | 1.00 | 36.07 |
| 753 | O | ALA | 208 | 34.525 | 52.467 | -12.425 | 1.00 | 38.58 |

FIG. 5AA

| Atom | Atom Type | Residue | # | X | Y | Z | OCC | B |
|---|---|---|---|---|---|---|---|---|
| 754 | N | SER | 209 | 32.419 | 51.840 | -12.707 | 1.00 | 38.40 |
| 755 | H | SER | 209 | 31.516 | 51.718 | -12.349 | 1.00 | 0.00 |
| 756 | CA | SER | 209 | 32.623 | 51.470 | -14.096 | 1.00 | 38.81 |
| 757 | CB | SER | 209 | 31.471 | 50.593 | -14.573 | 1.00 | 45.07 |
| 758 | OG | SER | 209 | 30.259 | 51.040 | -13.965 | 1.00 | 56.06 |
| 759 | HG | SER | 209 | 29.534 | 50.500 | -14.307 | 1.00 | 0.00 |
| 760 | C | SER | 209 | 32.724 | 52.676 | -14.978 | 1.00 | 35.05 |
| 761 | O | SER | 209 | 33.571 | 52.733 | -15.857 | 1.00 | 36.86 |
| 762 | N | ASP | 210 | 31.877 | 53.687 | -14.779 | 1.00 | 33.45 |
| 763 | H | ASP | 210 | 31.138 | 53.563 | -14.150 | 1.00 | 0.00 |
| 764 | CA | ASP | 210 | 32.061 | 54.930 | -15.516 | 1.00 | 36.67 |
| 765 | CB | ASP | 210 | 31.103 | 56.049 | -15.088 | 1.00 | 43.07 |
| 766 | CG | ASP | 210 | 29.602 | 55.780 | -15.228 | 1.00 | 51.26 |
| 767 | OD1 | ASP | 210 | 29.209 | 54.945 | -16.060 | 1.00 | 52.07 |
| 768 | OD2 | ASP | 210 | 28.830 | 56.441 | -14.507 | 1.00 | 50.26 |
| 769 | C | ASP | 210 | 33.469 | 55.432 | -15.219 | 1.00 | 36.66 |
| 770 | O | ASP | 210 | 34.155 | 55.935 | -16.096 | 1.00 | 34.14 |
| 771 | N | MET | 211 | 33.944 | 55.299 | -13.965 | 1.00 | 36.25 |
| 772 | H | MET | 211 | 33.371 | 54.919 | -13.268 | 1.00 | 0.00 |
| 773 | CA | MET | 211 | 35.310 | 55.693 | -13.629 | 1.00 | 36.30 |
| 774 | CB | MET | 211 | 35.574 | 55.528 | -12.130 | 1.00 | 32.55 |
| 775 | CG | MET | 211 | 34.914 | 56.611 | -11.271 | 1.00 | 31.33 |
| 776 | SD | MET | 211 | 35.182 | 56.360 | -9.493 | 1.00 | 38.31 |
| 777 | CE | MET | 211 | 34.219 | 57.715 | -8.954 | 1.00 | 38.56 |
| 778 | C | MET | 211 | 36.310 | 54.866 | -14.404 | 1.00 | 33.55 |
| 779 | O | MET | 211 | 37.247 | 55.382 | -14.999 | 1.00 | 35.45 |
| 780 | N | THR | 212 | 36.140 | 53.551 | -14.436 | 1.00 | 30.54 |
| 781 | H | THR | 212 | 35.445 | 53.118 | -13.893 | 1.00 | 0.00 |
| 782 | CA | THR | 212 | 36.997 | 52.704 | -15.242 | 1.00 | 31.66 |

FIG. 5BB

| Atom | Atom Type | Residue | # | X | Y | Z | OCC | B |
|---|---|---|---|---|---|---|---|---|
| 783 | CB | THR | 212 | 36.443 | 51.289 | -15.170 | 1.00 | 30.49 |
| 784 | OG1 | THR | 212 | 36.580 | 50.901 | -13.805 | 1.00 | 36.43 |
| 785 | HG1 | THR | 212 | 37.491 | 50.999 | -13.515 | 1.00 | 0.00 |
| 786 | CG2 | THR | 212 | 37.128 | 50.325 | -16.127 | 1.00 | 30.70 |
| 787 | C | THR | 212 | 37.122 | 53.142 | -16.681 | 1.00 | 30.78 |
| 788 | O | THR | 212 | 38.195 | 53.275 | -17.241 | 1.00 | 30.06 |
| 789 | N | THR | 213 | 35.973 | 53.375 | -17.297 | 1.00 | 34.48 |
| 790 | H | THR | 213 | 35.126 | 53.245 | -16.813 | 1.00 | 0.00 |
| 791 | CA | THR | 213 | 35.869 | 53.796 | -18.681 | 1.00 | 33.70 |
| 792 | CB | THR | 213 | 34.354 | 53.892 | -19.044 | 1.00 | 38.71 |
| 793 | OG1 | THR | 213 | 33.818 | 52.581 | -18.856 | 1.00 | 42.49 |
| 794 | HG1 | THR | 213 | 34.273 | 51.966 | -19.436 | 1.00 | 0.00 |
| 795 | CG2 | THR | 213 | 34.086 | 54.420 | -20.467 | 1.00 | 40.74 |
| 796 | C | THR | 213 | 36.571 | 55.122 | -18.900 | 1.00 | 31.43 |
| 797 | O | THR | 213 | 37.304 | 55.298 | -19.865 | 1.00 | 30.44 |
| 798 | N | GLU | 214 | 36.356 | 56.097 | -18.006 | 1.00 | 29.82 |
| 799 | H | GLU | 214 | 35.706 | 55.963 | -17.279 | 1.00 | 0.00 |
| 800 | CA | GLU | 214 | 37.082 | 57.351 | -18.103 | 1.00 | 29.65 |
| 801 | CB | GLU | 214 | 36.673 | 58.355 | -17.025 | 1.00 | 33.21 |
| 802 | CG | GLU | 214 | 35.275 | 58.972 | -17.161 | 1.00 | 39.44 |
| 803 | CD | GLU | 214 | 34.998 | 59.508 | -18.559 | 1.00 | 44.47 |
| 804 | OE1 | GLU | 214 | 35.754 | 60.353 | -19.052 | 1.00 | 46.83 |
| 805 | OE2 | GLU | 214 | 34.015 | 59.057 | -19.154 | 1.00 | 48.55 |
| 806 | C | GLU | 214 | 38.561 | 57.147 | -17.960 | 1.00 | 26.00 |
| 807 | O | GLU | 214 | 39.348 | 57.759 | -18.665 | 1.00 | 23.58 |
| 808 | N | LEU | 215 | 38.976 | 56.276 | -17.045 | 1.00 | 26.22 |
| 809 | H | LEU | 215 | 38.327 | 55.881 | -16.422 | 1.00 | 0.00 |
| 810 | CA | LEU | 215 | 40.392 | 55.922 | -16.942 | 1.00 | 30.25 |
| 811 | CB | LEU | 215 | 40.670 | 54.929 | -15.786 | 1.00 | 28.64 |

FIG. 5CC

| Atom | Atom Type | Residue | # | X | Y | Z | OCC | B |
|---|---|---|---|---|---|---|---|---|
| 812 | CG | LEU | 215 | 40.608 | 55.547 | -14.386 | 1.00 | 31.22 |
| 813 | CD1 | LEU | 215 | 40.822 | 54.470 | -13.329 | 1.00 | 30.89 |
| 814 | CD2 | LEU | 215 | 41.648 | 56.656 | -14.292 | 1.00 | 24.41 |
| 815 | C | LEU | 215 | 40.966 | 55.300 | -18.190 | 1.00 | 29.50 |
| 816 | O | LEU | 215 | 41.998 | 55.738 | -18.686 | 1.00 | 32.89 |
| 817 | N | GLU | 216 | 40.334 | 54.261 | -18.740 | 1.00 | 27.46 |
| 818 | H | GLU | 216 | 39.555 | 53.884 | -18.282 | 1.00 | 0.00 |
| 819 | CA | GLU | 216 | 40.802 | 53.695 | -19.991 | 1.00 | 30.27 |
| 820 | CB | GLU | 216 | 39.922 | 52.537 | -20.463 | 1.00 | 38.22 |
| 821 | CG | GLU | 216 | 39.940 | 51.319 | -19.517 | 1.00 | 54.67 |
| 822 | CD | GLU | 216 | 39.089 | 50.173 | -20.064 | 1.00 | 60.29 |
| 823 | OE1 | GLU | 216 | 39.535 | 49.546 | -21.027 | 1.00 | 63.24 |
| 824 | OE2 | GLU | 216 | 38.003 | 49.907 | -19.525 | 1.00 | 60.46 |
| 825 | C | GLU | 216 | 40.823 | 54.724 | -21.094 | 1.00 | 29.88 |
| 826 | O | GLU | 216 | 41.722 | 54.757 | -21.926 | 1.00 | 27.84 |
| 827 | N | ALA | 217 | 39.836 | 55.617 | -21.144 | 1.00 | 27.72 |
| 828 | H | ALA | 217 | 39.086 | 55.550 | -20.516 | 1.00 | 0.00 |
| 829 | CA | ALA | 217 | 39.851 | 56.698 | -22.121 | 1.00 | 27.12 |
| 830 | CB | ALA | 217 | 38.530 | 57.477 | -22.045 | 1.00 | 27.01 |
| 831 | C | ALA | 217 | 41.008 | 57.620 | -21.855 | 1.00 | 26.62 |
| 832 | O | ALA | 217 | 41.791 | 57.934 | -22.740 | 1.00 | 26.18 |
| 833 | N | PHE | 218 | 41.179 | 58.083 | -20.624 | 1.00 | 25.15 |
| 834 | H | PHE | 218 | 40.554 | 57.809 | -19.917 | 1.00 | 0.00 |
| 835 | CA | PHE | 218 | 42.258 | 58.999 | -20.319 | 1.00 | 23.19 |
| 836 | CB | PHE | 218 | 42.185 | 59.322 | -18.828 | 1.00 | 20.84 |
| 837 | CG | PHE | 218 | 43.236 | 60.340 | -18.445 | 1.00 | 25.38 |
| 838 | CD1 | PHE | 218 | 44.361 | 59.929 | -17.742 | 1.00 | 24.12 |
| 839 | CD2 | PHE | 218 | 43.036 | 61.686 | -18.721 | 1.00 | 23.15 |
| 840 | CE1 | PHE | 218 | 45.234 | 60.889 | -17.262 | 1.00 | 23.97 |

FIG. 5DD

| Atom | Atom Type | Residue | # | X | Y | Z | OCC | B |
|---|---|---|---|---|---|---|---|---|
| 841 | CE2 | PHE | 218 | 43.920 | 62.634 | -18.228 | 1.00 | 23.08 |
| 842 | CZ | PHE | 218 | 45.005 | 62.234 | -17.484 | 1.00 | 21.26 |
| 843 | C | PHE | 218 | 43.603 | 58.427 | -20.701 | 1.00 | 25.14 |
| 844 | O | PHE | 218 | 44.495 | 59.110 | -21.209 | 1.00 | 29.00 |
| 845 | N | ALA | 219 | 43.772 | 57.138 | -20.456 | 1.00 | 23.61 |
| 846 | H | ALA | 219 | 43.083 | 56.655 | -19.953 | 1.00 | 0.00 |
| 847 | CA | ALA | 219 | 44.971 | 56.429 | -20.858 | 1.00 | 24.15 |
| 848 | CB | ALA | 219 | 44.884 | 54.979 | -20.375 | 1.00 | 24.62 |
| 849 | C | ALA | 219 | 45.224 | 56.436 | -22.351 | 1.00 | 30.25 |
| 850 | O | ALA | 219 | 46.335 | 56.291 | -22.834 | 1.00 | 30.75 |
| 851 | N | HIS | 220 | 44.155 | 56.608 | -23.131 | 1.00 | 31.80 |
| 852 | H | HIS | 220 | 43.276 | 56.759 | -22.722 | 1.00 | 0.00 |
| 853 | CA | HIS | 220 | 44.260 | 56.691 | -24.578 | 1.00 | 32.54 |
| 854 | CB | HIS | 220 | 43.030 | 56.108 | -25.287 | 1.00 | 33.65 |
| 855 | CG | HIS | 220 | 43.153 | 54.627 | -25.144 | 1.00 | 38.22 |
| 856 | CD2 | HIS | 220 | 43.712 | 53.790 | -26.069 | 1.00 | 40.87 |
| 857 | ND1 | HIS | 220 | 42.884 | 53.894 | -24.069 | 1.00 | 2.77 |
| 858 | HD1 | HIS | 220 | 42.460 | 54.202 | -23.244 | 1.00 | 0.00 |
| 859 | CE1 | HIS | 220 | 43.283 | 52.673 | -24.281 | 1.00 | 41.06 |
| 860 | NE2 | HIS | 220 | 43.788 | 52.624 | -25.483 | 1.00 | 39.69 |
| 861 | HE2 | HIS | 220 | 44.189 | 51.815 | -25.855 | 1.00 | 0.00 |
| 862 | C | HIS | 220 | 44.431 | 58.066 | -25.139 | 1.00 | 31.27 |
| 863 | O | HIS | 220 | 44.482 | 58.222 | -26.346 | 1.00 | 34.54 |
| 864 | N | ARG | 221 | 44.519 | 59.129 | -24.354 | 1.00 | 31.23 |
| 865 | H | ARG | 221 | 44.453 | 59.018 | -23.381 | 1.00 | 0.00 |
| 866 | CA | ARG | 221 | 44.684 | 60.441 | -24.935 | 1.00 | 25.20 |
| 867 | CB | ARG | 221 | 44.496 | 61.460 | -23.847 | 1.00 | 23.87 |
| 868 | CG | ARG | 221 | 43.089 | 61.433 | -23.298 | 1.00 | 24.28 |
| 869 | CD | ARG | 221 | 42.164 | 62.262 | -24.150 | 1.00 | 24.77 |

FIG. 5EE

| Atom | Atom Type | Residue | # | X | Y | Z | OCC | B |
|---|---|---|---|---|---|---|---|---|
| 870 | NE | ARG | 221 | 42.527 | 63.666 | -24.117 | 1.00 | 30.34 |
| 871 | HE | ARG | 221 | 43.163 | 64.003 | -24.780 | 1.00 | 0.00 |
| 872 | CZ | ARG | 221 | 42.025 | 64.537 | -23.214 | 1.00 | 36.39 |
| 873 | NH1 | ARG | 221 | 41.323 | 64.137 | -22.120 | 1.00 | 37.62 |
| 874 | HH11 | ARG | 221 | 41.185 | 63.163 | -21.950 | 1.00 | 0.00 |
| 875 | HH12 | ARG | 221 | 40.981 | 64.814 | -21.467 | 1.00 | 0.00 |
| 876 | NH2 | ARG | 221 | 42.162 | 65.884 | -23.412 | 1.00 | 36.36 |
| 877 | HH21 | ARG | 221 | 42.631 | 66.223 | -24.228 | 1.00 | 0.00 |
| 878 | HH22 | ARG | 221 | 41.797 | 66.529 | -22.740 | 1.00 | 0.00 |
| 879 | C | ARG | 221 | 46.030 | 60.643 | -25.605 | 1.00 | 27.94 |
| 880 | O | ARG | 221 | 47.097 | 60.475 | -25.015 | 1.00 | 27.32 |
| 881 | N | PRO | 222 | 46.015 | 61.030 | -26.842 | 1.00 | 30.14 |
| 882 | CD | PRO | 222 | 44.795 | 61.277 | -27.621 | 1.00 | 28.66 |
| 883 | CA | PRO | 222 | 47.204 | 61.317 | -27.635 | 1.00 | 26.80 |
| 884 | CB | PRO | 222 | 46.670 | 61.799 | -28.976 | 1.00 | 27.03 |
| 885 | CG | PRO | 222 | 45.279 | 62.298 | -28.634 | 1.00 | 26.07 |
| 886 | C | PRO | 222 | 48.125 | 62.326 | -26.990 | 1.00 | 28.33 |
| 887 | O | PRO | 222 | 49.329 | 62.305 | -27.184 | 1.00 | 34.07 |
| 888 | N | GLU | 223 | 47.627 | 63.254 | -26.189 | 1.00 | 25.34 |
| 889 | H | GLU | 223 | 46.669 | 63.259 | -26.005 | 1.00 | 0.00 |
| 890 | CA | GLU | 223 | 48.500 | 64.265 | -25.620 | 1.00 | 28.40 |
| 891 | CB | GLU | 223 | 47.671 | 65.306 | -24.887 | 1.00 | 27.51 |
| 892 | CG | GLU | 223 | 46.658 | 66.030 | -25.769 | 1.00 | 32.04 |
| 893 | CD | GLU | 223 | 45.293 | 65.381 | -25.726 | 1.00 | 34.72 |
| 894 | OE1 | GLU | 223 | 44.328 | 66.114 | -25.534 | 1.00 | 35.25 |
| 895 | OE2 | GLU | 223 | 45.177 | 64.168 | -25.880 | 1.00 | 38.35 |
| 896 | C | GLU | 223 | 49.569 | 63.758 | -24.663 | 1.00 | 28.17 |
| 897 | O | GLU | 223 | 50.606 | 64.371 | -24.461 | 1.00 | 28.18 |
| 898 | N | HIS | 224 | 49.343 | 62.599 | -24.034 | 1.00 | 26.29 |

FIG. 5FF

| Atom | Atom Type | Residue | # | X | Y | Z | OCC | B |
|---|---|---|---|---|---|---|---|---|
| 899 | H | HIS | 224 | 48.522 | 62.108 | -24.230 | 1.00 | 0.00 |
| 900 | CA | HIS | 224 | 50.346 | 62.037 | -23.139 | 1.00 | 25.11 |
| 901 | CB | HIS | 224 | 49.960 | 60.670 | -22.601 | 1.00 | 21.67 |
| 902 | CG | HIS | 224 | 48.774 | 60.779 | -21.676 | 1.00 | 28.93 |
| 903 | CD2 | HIS | 224 | 47.721 | 59.901 | -21.673 | 1.00 | 29.23 |
| 904 | ND1 | HIS | 224 | 48.546 | 61.704 | -20.722 | 1.00 | 26.59 |
| 905 | HD1 | HIS | 224 | 49.236 | 62.337 | -20.408 | 1.00 | 0.00 |
| 906 | CE1 | HIS | 224 | 47.382 | 61.423 | -20.177 | 1.00 | 31.44 |
| 907 | NE2 | HIS | 224 | 46.889 | 60.352 | -20.773 | 1.00 | 33.43 |
| 908 | HE2 | HIS | 224 | 46.004 | 59.939 | -20.625 | 1.00 | 0.00 |
| 909 | C | HIS | 224 | 51.646 | 61.845 | -23.859 | 1.00 | 26.89 |
| 910 | O | HIS | 224 | 52.700 | 62.029 | -23.281 | 1.00 | 30.62 |
| 911 | N | LYS | 225 | 51.608 | 61.474 | -25.138 | 1.00 | 30.81 |
| 912 | H | LYS | 225 | 50.750 | 61.290 | -25.584 | 1.00 | 0.00 |
| 913 | CA | LYS | 225 | 52.826 | 61.359 | -25.937 | 1.00 | 32.77 |
| 914 | CB | LYS | 225 | 52.503 | 60.985 | -27.373 | 1.00 | 39.91 |
| 915 | CG | LYS | 225 | 52.645 | 59.492 | -27.564 | 1.00 | 55.31 |
| 916 | CD | LYS | 225 | 52.548 | 59.057 | -29.024 | 1.00 | 67.66 |
| 917 | CE | LYS | 225 | 52.571 | 57.524 | -29.181 | 1.00 | 75.00 |
| 918 | NZ | LYS | 225 | 51.337 | 56.917 | -28.699 | 1.00 | 78.51 |
| 919 | HZ1 | LYS | 225 | 50.529 | 57.292 | -29.236 | 1.00 | 0.00 |
| 920 | HZ2 | LYS | 225 | 51.211 | 57.140 | -27.691 | 1.00 | 0.00 |
| 921 | HZ3 | LYS | 225 | 51.387 | 55.887 | -28.827 | 1.00 | 0.00 |
| 922 | C | LYS | 225 | 53.638 | 62.627 | -25.985 | 1.00 | 30.17 |
| 923 | O | LYS | 225 | 54.854 | 62.599 | -26.051 | 1.00 | 32.06 |
| 924 | N | THR | 226 | 53.015 | 63.792 | -25.975 | 1.00 | 29.27 |
| 925 | H | THR | 226 | 52.045 | 63.869 | -26.061 | 1.00 | 0.00 |
| 926 | CA | THR | 226 | 53.803 | 64.992 | -25.854 | 1.00 | 29.35 |
| 927 | CB | THR | 226 | 53.293 | 66.018 | -26.896 | 1.00 | 28.73 |

FIG. 5GG

| Atom | Atom Type | Residue | # | X | Y | Z | OCC | B |
|---|---|---|---|---|---|---|---|---|
| 991 | CB | VAL | 233 | 42.519 | 64.812 | -8.180 | 1.00 | 21.39 |
| 992 | CG1 | VAL | 233 | 42.185 | 65.090 | -6.706 | 1.00 | 20.83 |
| 993 | CG2 | VAL | 233 | 43.826 | 65.525 | -8.539 | 1.00 | 27.21 |
| 994 | C | VAL | 233 | 41.291 | 62.645 | -8.264 | 1.00 | 27.10 |
| 995 | O | VAL | 233 | 40.429 | 62.803 | -9.122 | 1.00 | 24.87 |
| 996 | N | PHE | 234 | 41.049 | 61.906 | -7.176 | 1.00 | 24.72 |
| 997 | H | PHE | 234 | 41.749 | 61.801 | -6.495 | 1.00 | 0.00 |
| 998 | CA | PHE | 234 | 39.764 | 61.286 | -6.938 | 1.00 | 23.25 |
| 999 | CB | PHE | 234 | 39.870 | 59.773 | -6.767 | 1.00 | 20.01 |
| 1000 | CG | PHE | 234 | 40.400 | 59.110 | -8.005 | 1.00 | 21.08 |
| 1001 | CD1 | PHE | 234 | 39.525 | 58.555 | -8.904 | 1.00 | 26.42 |
| 1002 | CD2 | PHE | 234 | 41.768 | 59.045 | -8.222 | 1.00 | 25.79 |
| 1003 | CE1 | PHE | 234 | 40.019 | 57.951 | -10.046 | 1.00 | 29.30 |
| 1004 | CE2 | PHE | 234 | 42.262 | 58.445 | -9.353 | 1.00 | 23.33 |
| 1005 | CZ | PHE | 234 | 41.379 | 57.910 | -10.266 | 1.00 | 31.52 |
| 1006 | C | PHE | 234 | 39.259 | 61.858 | -5.650 | 1.00 | 25.38 |
| 1007 | O | PHE | 234 | 39.990 | 61.926 | -4.664 | 1.00 | 27.17 |
| 1008 | N | MET | 235 | 38.006 | 62.298 | -5.583 | 1.00 | 26.22 |
| 1009 | H | MET | 235 | 37.441 | 62.301 | -6.384 | 1.00 | 0.00 |
| 1010 | CA | MET | 235 | 37.451 | 62.780 | -4.326 | 1.00 | 25.64 |
| 1011 | CB | MET | 235 | 37.276 | 64.294 | -4.345 | 1.00 | 24.45 |
| 1012 | CG | MET | 235 | 38.619 | 64.946 | -4.681 | 1.00 | 30.66 |
| 1013 | SD | MET | 235 | 38.601 | 66.742 | -4.848 | 1.00 | 37.65 |
| 1014 | CE | MET | 235 | 38.003 | 66.982 | -6.481 | 1.00 | 33.32 |
| 1015 | C | MET | 235 | 36.120 | 62.112 | -4.236 | 1.00 | 29.15 |
| 1016 | O | MET | 235 | 35.339 | 62.186 | -5.175 | 1.00 | 29.75 |
| 1017 | N | SER | 236 | 35.808 | 61.432 | -3.138 | 1.00 | 31.99 |
| 1018 | H | SER | 236 | 36.441 | 61.364 | -2.382 | 1.00 | 0.00 |
| 1019 | CA | SER | 236 | 34.531 | 60.769 | -2.995 | 1.00 | 32.91 |
| 1020 | CB | SER | 236 | 34.412 | 59.596 | -3.971 | 1.00 | 31.29 |
| 1021 | OG | SER | 236 | 33.125 | 58.996 | -3.885 | 1.00 | 32.86 |

FIG. 5HH

| Atom | Atom Type | Residue | # | X | Y | Z | OCC | B |
|---|---|---|---|---|---|---|---|---|
| 957 | O | SER | 229 | 51.900 | 64.273 | -17.423 | 1.00 | 23.18 |
| 958 | N | THR | 230 | 51.720 | 63.201 | -15.435 | 1.00 | 24.93 |
| 959 | H | THR | 230 | 52.164 | 62.618 | -14.780 | 1.00 | 0.00 |
| 960 | CA | THR | 230 | 50.303 | 63.473 | -15.239 | 1.00 | 22.17 |
| 961 | CB | THR | 230 | 49.501 | 62.410 | -16.052 | 1.00 | 18.90 |
| 962 | OG1 | THR | 230 | 48.158 | 62.903 | -16.198 | 1.00 | 23.08 |
| 963 | HG1 | THR | 230 | 48.158 | 63.784 | -16.611 | 1.00 | 0.00 |
| 964 | CG2 | THR | 230 | 49.485 | 61.030 | -15.391 | 1.00 | 17.19 |
| 965 | C | THR | 230 | 49.933 | 63.471 | -13.739 | 1.00 | 22.19 |
| 966 | O | THR | 230 | 50.683 | 63.015 | -12.887 | 1.00 | 19.95 |
| 967 | N | PHE | 231 | 48.751 | 63.999 | -13.412 | 1.00 | 23.01 |
| 968 | H | PHE | 231 | 48.196 | 64.345 | -14.142 | 1.00 | 0.00 |
| 969 | CA | PHE | 231 | 48.168 | 64.022 | -12.081 | 1.00 | 22.98 |
| 970 | CB | PHE | 231 | 47.955 | 65.441 | -11.549 | 1.00 | 22.01 |
| 971 | CG | PHE | 231 | 49.190 | 65.978 | -10.873 | 1.00 | 23.66 |
| 972 | CD1 | PHE | 231 | 49.220 | 66.071 | -9.486 | 1.00 | 22.17 |
| 973 | CD2 | PHE | 231 | 50.273 | 66.392 | -11.635 | 1.00 | 21.19 |
| 974 | CE1 | PHE | 231 | 50.361 | 66.561 | -8.861 | 1.00 | 23.83 |
| 975 | CE2 | PHE | 231 | 51.391 | 66.900 | -11.010 | 1.00 | 18.70 |
| 976 | CZ | PHE | 231 | 51.442 | 66.965 | -9.620 | 1.00 | 22.93 |
| 977 | C | PHE | 231 | 46.792 | 63.409 | -12.160 | 1.00 | 21.75 |
| 978 | O | PHE | 231 | 46.067 | 63.809 | -13.062 | 1.00 | 21.91 |
| 979 | N | LEU | 232 | 46.343 | 62.479 | -11.312 | 1.00 | 20.85 |
| 980 | H | LEU | 232 | 46.949 | 62.069 | -10.654 | 1.00 | 0.00 |
| 981 | CA | LEU | 232 | 44.915 | 62.139 | -11.293 | 1.00 | 19.87 |
| 982 | CB | LEU | 232 | 44.627 | 60.672 | -11.588 | 1.00 | 23.90 |
| 983 | CG | LEU | 232 | 45.050 | 60.289 | -12.995 | 1.00 | 30.22 |
| 984 | CD1 | LEU | 232 | 46.486 | 59.760 | -12.956 | 1.00 | 32.80 |
| 985 | CD2 | LEU | 232 | 44.089 | 59.240 | -13.555 | 1.00 | 32.58 |

FIG. 5II

| Atom | Atom Type | Residue | # | X | Y | Z | OCC | B |
|---|---|---|---|---|---|---|---|---|
| 986 | C | LEU | 232 | 44.338 | 62.387 | -9.941 | 1.00 | 18.92 |
| 987 | O | LEU | 232 | 44.980 | 62.002 | -8.979 | 1.00 | 22.64 |
| 988 | N | VAL | 233 | 43.174 | 62.998 | -9.754 | 1.00 | 20.69 |
| 989 | H | VAL | 233 | 42.629 | 63.238 | -10.535 | 1.00 | 0.00 |
| 990 | CA | VAL | 233 | 42.664 | 63.290 | -8.423 | 1.00 | 22.20 |
| 991 | CB | VAL | 233 | 42.519 | 64.812 | -8.180 | 1.00 | 21.39 |
| 992 | CG1 | VAL | 233 | 42.185 | 65.090 | -6.706 | 1.00 | 20.83 |
| 993 | CG2 | VAL | 233 | 43.826 | 65.525 | -8.539 | 1.00 | 27.21 |
| 994 | C | VAL | 233 | 41.291 | 62.645 | -8.264 | 1.00 | 27.10 |
| 995 | O | VAL | 233 | 40.429 | 62.803 | -9.122 | 1.00 | 24.87 |
| 996 | N | PHE | 234 | 41.049 | 61.906 | -7.176 | 1.00 | 24.72 |
| 997 | H | PHE | 234 | 41.749 | 61.801 | -6.495 | 1.00 | 0.00 |
| 998 | CA | PHE | 234 | 39.764 | 61.286 | -6.938 | 1.00 | 23.25 |
| 999 | CB | PHE | 234 | 39.870 | 59.773 | -6.767 | 1.00 | 20.01 |
| 1000 | CG | PHE | 234 | 40.400 | 59.110 | -8.005 | 1.00 | 21.08 |
| 1001 | CD1 | PHE | 234 | 39.525 | 58.555 | -8.904 | 1.00 | 26.42 |
| 1002 | CD2 | PHE | 234 | 41.768 | 59.045 | -8.222 | 1.00 | 25.79 |
| 1003 | CE1 | PHE | 234 | 40.019 | 57.951 | -10.046 | 1.00 | 29.30 |
| 1004 | CE2 | PHE | 234 | 42.262 | 58.445 | -9.353 | 1.00 | 23.33 |
| 1005 | CZ | PHE | 234 | 41.379 | 57.910 | -10.266 | 1.00 | 31.52 |
| 1006 | C | PHE | 234 | 39.259 | 61.858 | -5.650 | 1.00 | 25.38 |
| 1007 | O | PHE | 234 | 39.990 | 61.926 | -4.664 | 1.00 | 27.17 |
| 1008 | N | MET | 235 | 38.006 | 62.298 | -5.583 | 1.00 | 26.22 |
| 1009 | H | MET | 235 | 37.441 | 62.301 | -6.384 | 1.00 | 0.00 |
| 1010 | CA | MET | 235 | 37.451 | 62.780 | -4.326 | 1.00 | 25.64 |
| 1011 | CB | MET | 235 | 37.276 | 64.294 | -4.345 | 1.00 | 24.45 |
| 1012 | CG | MET | 235 | 38.619 | 64.946 | -4.681 | 1.00 | 30.66 |
| 1013 | SD | MET | 235 | 38.601 | 66.742 | -4.848 | 1.00 | 37.65 |
| 1014 | CE | MET | 235 | 38.003 | 66.982 | -6.481 | 1.00 | 33.32 |

FIG. 5JJ

| Atom | Atom Type | Residue | # | X | Y | Z | OCC | B |
|---|---|---|---|---|---|---|---|---|
| 1015 | C | MET | 235 | 36.120 | 62.112 | -4.236 | 1.00 | 29.15 |
| 1016 | O | MET | 235 | 35.339 | 62.186 | -5.175 | 1.00 | 29.75 |
| 1017 | N | SER | 236 | 35.808 | 61.432 | -3.138 | 1.00 | 31.99 |
| 1018 | H | SER | 236 | 36.441 | 61.364 | -2.382 | 1.00 | 0.00 |
| 1019 | CA | SER | 236 | 34.531 | 60.769 | -2.995 | 1.00 | 32.91 |
| 1020 | CB | SER | 236 | 34.412 | 59.596 | -3.971 | 1.00 | 31.29 |
| 1021 | OG | SER | 236 | 33.125 | 58.996 | -3.885 | 1.00 | 32.86 |
| 1022 | HG | SER | 236 | 32.463 | 59.641 | -4.143 | 1.00 | 0.00 |
| 1023 | C | SER | 236 | 34.462 | 60.246 | -1.573 | 1.00 | 32.69 |
| 1024 | O | SER | 236 | 35.389 | 60.340 | -0.778 | 1.00 | 33.35 |
| 1025 | N | HIS | 237 | 33.329 | 59.661 | -1.203 | 1.00 | 33.10 |
| 1026 | H | HIS | 237 | 32.551 | 59.730 | -1.783 | 1.00 | 0.00 |
| 1027 | CA | HIS | 237 | 33.332 | 58.809 | -0.016 | 1.00 | 34.12 |
| 1028 | CB | HIS | 237 | 31.882 | 58.331 | 0.377 | 1.00 | 37.00 |
| 1029 | CG | HIS | 237 | 31.079 | 59.375 | 1.141 | 1.00 | 42.87 |
| 1030 | CD2 | HIS | 237 | 29.798 | 59.740 | 0.816 | 1.00 | 40.88 |
| 1031 | ND1 | HIS | 237 | 31.457 | 60.128 | 2.188 | 1.00 | 41.19 |
| 1032 | HD1 | HIS | 237 | 32.325 | 60.120 | 2.661 | 1.00 | 0.00 |
| 1033 | CE1 | HIS | 237 | 30.460 | 60.934 | 2.446 | 1.00 | 43.14 |
| 1034 | NE2 | HIS | 237 | 29.466 | 60.721 | 1.609 | 1.00 | 42.94 |
| 1035 | HE2 | HIS | 237 | 28.639 | 61.252 | 1.540 | 1.00 | 0.00 |
| 1036 | C | HIS | 237 | 34.194 | 57.577 | -0.321 | 1.00 | 33.55 |
| 1037 | O | HIS | 237 | 34.520 | 57.234 | -1.462 | 1.00 | 32.97 |
| 1038 | N | GLY | 238 | 34.606 | 56.852 | 0.702 | 1.00 | 32.27 |
| 1039 | H | GLY | 238 | 34.429 | 57.073 | 1.646 | 1.00 | 0.00 |
| 1040 | CA | GLY | 238 | 35.369 | 55.668 | 0.428 | 1.00 | 31.94 |
| 1041 | C | GLY | 238 | 35.217 | 54.774 | 1.609 | 1.00 | 31.47 |
| 1042 | O | GLY | 238 | 34.874 | 55.189 | 2.707 | 1.00 | 29.62 |
| 1043 | N | ILE | 239 | 35.475 | 53.512 | 1.370 | 1.00 | 30.61 |

FIG. 5KK

| Atom | Atom Type | Residue | # | X | Y | Z | OCC | B |
|---|---|---|---|---|---|---|---|---|
| 1115 | HZ3 | LYS | 246 | 23.112 | 59.670 | -10.742 | 1.00 | 0.00 |
| 1116 | C | LYS | 246 | 26.477 | 56.209 | -6.574 | 1.00 | 48.40 |
| 1117 | O | LYS | 246 | 25.597 | 56.538 | -5.778 | 1.00 | 42.25 |
| 1118 | N | LYS | 247 | 26.479 | 54.982 | -7.079 | 1.00 | 45.29 |
| 1119 | H | LYS | 247 | 27.176 | 54.727 | -7.713 | 1.00 | 0.00 |
| 1120 | CA | LYS | 247 | 25.465 | 54.045 | -6.685 | 1.00 | 49.00 |
| 1121 | CB | LYS | 247 | 25.209 | 53.130 | -7.875 | 1.00 | 54.11 |
| 1122 | CG | LYS | 247 | 24.508 | 53.886 | -9.004 | 1.00 | 62.74 |
| 1123 | CD | LYS | 247 | 24.243 | 53.001 | -10.220 | 1.00 | 72.81 |
| 1124 | CE | LYS | 247 | 23.531 | 53.721 | -11.379 | 1.00 | 81.38 |
| 1125 | NZ | LYS | 247 | 23.373 | 52.835 | -12.526 | 1.00 | 86.55 |
| 1126 | HZ1 | LYS | 247 | 22.808 | 52.005 | -12.261 | 1.00 | 0.00 |
| 1127 | HZ2 | LYS | 247 | 24.310 | 52.525 | -12.854 | 1.00 | 0.00 |
| 1128 | HZ3 | LYS | 247 | 22.899 | 53.347 | -13.297 | 1.00 | 0.00 |
| 1129 | C | LYS | 247 | 25.856 | 53.257 | -5.450 | 1.00 | 49.50 |
| 1130 | O | LYS | 247 | 25.319 | 52.203 | -5.182 | 1.00 | 51.73 |
| 1131 | N | HIS | 248 | 26.793 | 53.661 | -4.603 | 1.00 | 50.46 |
| 1132 | H | HIS | 248 | 27.235 | 54.526 | -4.728 | 1.00 | 0.00 |
| 1133 | CA | HIS | 248 | 27.155 | 52.799 | -3.498 | 1.00 | 45.73 |
| 1134 | CB | HIS | 248 | 28.438 | 53.305 | -2.813 | 1.00 | 40.60 |
| 1135 | CG | HIS | 248 | 28.924 | 52.330 | -1.737 | 1.00 | 36.78 |
| 1136 | CD2 | HIS | 248 | 29.411 | 51.071 | -1.973 | 1.00 | 33.70 |
| 1137 | ND1 | HIS | 248 | 28.983 | 52.505 | -0.416 | 1.00 | 38.30 |
| 1138 | HD1 | HIS | 248 | 28.728 | 53.315 | 0.070 | 1.00 | 0.00 |
| 1139 | CE1 | HIS | 248 | 29.467 | 51.412 | 0.129 | 1.00 | 34.58 |
| 1140 | NE2 | HIS | 248 | 29.720 | 50.547 | -0.817 | 1.00 | 33.39 |
| 1141 | HE2 | HIS | 248 | 30.051 | 49.640 | -0.658 | 1.00 | 0.00 |
| 1142 | C | HIS | 248 | 26.055 | 52.703 | -2.473 | 1.00 | 48.32 |
| 1143 | O | HIS | 248 | 25.591 | 53.685 | -1.918 | 1.00 | 44.66 |
| 1144 | N | SER | 249 | 25.626 | 51.478 | -2.198 | 1.00 | 53.23 |
| 1145 | H | SER | 249 | 25.852 | 50.711 | -2.770 | 1.00 | 0.00 |

FIG. 5LL

| Atom | Atom Type | Residue | # | X | Y | Z | OCC | B |
|---|---|---|---|---|---|---|---|---|
| 1073 | CG | GLU | 241 | 37.559 | 46.447 | -1.379 | 1.00 | 76.02 |
| 1074 | CD | GLU | 241 | 36.387 | 45.686 | -2.058 | 1.00 | 84.57 |
| 1075 | OE1 | GLU | 241 | 35.539 | 46.310 | -2.712 | 1.00 | 86.53 |
| 1076 | OE2 | GLU | 241 | 36.350 | 44.449 | -1.970 | 1.00 | 90.34 |
| 1077 | C | GLU | 241 | 38.559 | 49.403 | -1.009 | 1.00 | 45.34 |
| 1078 | O | GLU | 241 | 39.236 | 49.102 | -1.985 | 1.00 | 45.76 |
| 1079 | N | GLY | 242 | 38.015 | 50.628 | -0.966 | 1.00 | 40.75 |
| 1080 | H | GLY | 242 | 37.428 | 50.949 | -0.241 | 1.00 | 0.00 |
| 1081 | CA | GLY | 242 | 38.362 | 51.556 | -2.014 | 1.00 | 35.23 |
| 1082 | C | GLY | 242 | 37.375 | 52.679 | -2.047 | 1.00 | 33.55 |
| 1083 | O | GLY | 242 | 36.694 | 52.955 | -1.071 | 1.00 | 32.49 |
| 1084 | N | ILE | 243 | 37.290 | 53.311 | -3.213 | 1.00 | 31.51 |
| 1085 | H | ILE | 243 | 37.707 | 52.888 | -3.992 | 1.00 | 0.00 |
| 1086 | CA | ILE | 243 | 36.590 | 54.576 | -3.407 | 1.00 | 30.20 |
| 1087 | CB | ILE | 243 | 37.364 | 55.376 | -4.511 | 1.00 | 31.68 |
| 1088 | CG2 | ILE | 243 | 36.739 | 56.740 | -4.856 | 1.00 | 28.31 |
| 1089 | CG1 | ILE | 243 | 38.749 | 55.674 | -3.963 | 1.00 | 31.33 |
| 1090 | CD1 | ILE | 243 | 39.643 | 56.077 | -5.135 | 1.00 | 35.46 |
| 1091 | C | ILE | 243 | 35.148 | 54.304 | -3.806 | 1.00 | 30.26 |
| 1092 | O | ILE | 243 | 34.920 | 53.418 | -4.618 | 1.00 | 30.91 |
| 1093 | N | CYS | 244 | 34.151 | 55.017 | -3.276 | 1.00 | 29.95 |
| 1094 | H | CYS | 244 | 34.337 | 55.767 | -2.666 | 1.00 | 0.00 |
| 1095 | CA | CYS | 244 | 32.774 | 54.760 | -3.652 | 1.00 | 31.93 |
| 1096 | CB | CYS | 244 | 31.855 | 55.223 | -2.553 | 1.00 | 29.44 |
| 1097 | SG | CYS | 244 | 32.093 | 54.318 | -1.030 | 1.00 | 36.45 |
| 1098 | C | CYS | 244 | 32.291 | 55.415 | -4.945 | 1.00 | 35.60 |
| 1099 | O | CYS | 244 | 32.427 | 56.619 | -5.169 | 1.00 | 34.97 |
| 1100 | N | GLY | 245 | 31.695 | 54.653 | -5.863 | 1.00 | 34.56 |
| 1101 | H | GLY | 245 | 31.752 | 53.680 | -5.763 | 1.00 | 0.00 |

FIG. 5MM

| Atom | Atom Type | Residue | # | X | Y | Z | OCC | B |
|---|---|---|---|---|---|---|---|---|
| 1102 | CA | GLY | 245 | 30.973 | 55.279 | -6.962 | 1.00 | 37.28 |
| 1103 | C | GLY | 245 | 29.574 | 55.745 | -6.552 | 1.00 | 42.13 |
| 1104 | O | GLY | 245 | 29.085 | 55.433 | -5.470 | 1.00 | 41.53 |
| 1105 | N | LYS | 246 | 28.868 | 56.501 | -7.415 | 1.00 | 44.81 |
| 1106 | H | LYS | 246 | 29.231 | 56.669 | -8.312 | 1.00 | 0.00 |
| 1107 | CA | LYS | 246 | 27.604 | 57.140 | -7.033 | 1.00 | 47.47 |
| 1108 | CB | LYS | 246 | 27.040 | 57.989 | -8.186 | 1.00 | 46.88 |
| 1109 | CG | LYS | 246 | 26.636 | 57.098 | -9.348 | 1.00 | 51.88 |
| 1110 | CD | LYS | 246 | 25.882 | 57.806 | -10.459 | 1.00 | 62.88 |
| 1111 | CE | LYS | 246 | 24.560 | 58.422 | -10.000 | 1.00 | 69.93 |
| 1112 | NZ | LYS | 246 | 24.007 | 59.246 | -11.063 | 1.00 | 76.93 |
| 1113 | HZ1 | LYS | 246 | 23.833 | 58.663 | -11.905 | 1.00 | 0.00 |
| 1114 | HZ2 | LYS | 246 | 24.678 | 60.006 | -11.295 | 1.00 | 0.00 |
| 1115 | HZ3 | LYS | 246 | 23.112 | 59.670 | -10.742 | 1.00 | 0.00 |
| 1116 | C | LYS | 246 | 26.477 | 56.209 | -6.574 | 1.00 | 48.40 |
| 1117 | O | LYS | 246 | 25.597 | 56.538 | -5.778 | 1.00 | 42.25 |
| 1118 | N | LYS | 247 | 26.479 | 54.982 | -7.079 | 1.00 | 45.29 |
| 1119 | H | LYS | 247 | 27.176 | 54.727 | -7.713 | 1.00 | 0.00 |
| 1120 | CA | LYS | 247 | 25.465 | 54.045 | -6.685 | 1.00 | 49.00 |
| 1121 | CB | LYS | 247 | 25.209 | 53.130 | -7.875 | 1.00 | 54.11 |
| 1122 | CG | LYS | 247 | 24.508 | 53.886 | -9.004 | 1.00 | 62.74 |
| 1123 | CD | LYS | 247 | 24.243 | 53.001 | -10.220 | 1.00 | 72.81 |
| 1124 | CE | LYS | 247 | 23.531 | 53.721 | -11.379 | 1.00 | 81.38 |
| 1125 | NZ | LYS | 247 | 23.373 | 52.835 | -12.526 | 1.00 | 86.55 |
| 1126 | HZ1 | LYS | 247 | 22.808 | 52.005 | -12.261 | 1.00 | 0.00 |
| 1127 | HZ2 | LYS | 247 | 24.310 | 52.525 | -12.854 | 1.00 | 0.00 |
| 1128 | HZ3 | LYS | 247 | 22.899 | 53.347 | -13.297 | 1.00 | 0.00 |
| 1129 | C | LYS | 247 | 25.856 | 53.257 | -5.450 | 1.00 | 49.50 |
| 1130 | O | LYS | 247 | 25.319 | 52.203 | -5.182 | 1.00 | 51.73 |

FIG. 5NN

| Atom | Atom Type | Residue | # | X | Y | Z | OCC | B |
|---|---|---|---|---|---|---|---|---|
| 1131 | N | HIS | 248 | 26.793 | 53.661 | -4.603 | 1.00 | 50.46 |
| 1132 | H | HIS | 248 | 27.235 | 54.526 | -4.728 | 1.00 | 0.00 |
| 1133 | CA | HIS | 248 | 27.155 | 52.799 | -3.498 | 1.00 | 45.73 |
| 1134 | CB | HIS | 248 | 28.438 | 53.305 | -2.813 | 1.00 | 40.60 |
| 1135 | CG | HIS | 248 | 28.924 | 52.330 | -1.737 | 1.00 | 36.78 |
| 1136 | CD2 | HIS | 248 | 29.411 | 51.071 | -1.973 | 1.00 | 33.70 |
| 1137 | ND1 | HIS | 248 | 28.983 | 52.505 | -0.416 | 1.00 | 38.30 |
| 1138 | HD1 | HIS | 248 | 28.728 | 53.315 | 0.070 | 1.00 | 0.00 |
| 1139 | CE1 | HIS | 248 | 29.467 | 51.412 | 0.129 | 1.00 | 34.58 |
| 1140 | NE2 | HIS | 248 | 29.720 | 50.547 | -0.817 | 1.00 | 33.39 |
| 1141 | HE2 | HIS | 248 | 30.051 | 49.640 | -0.658 | 1.00 | 0.00 |
| 1142 | C | HIS | 248 | 26.055 | 52.703 | -2.473 | 1.00 | 48.32 |
| 1143 | O | HIS | 248 | 25.591 | 53.685 | -1.918 | 1.00 | 44.66 |
| 1144 | N | SER | 249 | 25.626 | 51.478 | -2.198 | 1.00 | 53.23 |
| 1145 | H | SER | 249 | 25.852 | 50.711 | -2.770 | 1.00 | 0.00 |
| 1146 | CA | SER | 249 | 24.798 | 51.233 | -1.040 | 1.00 | 57.14 |
| 1147 | CB | SER | 249 | 23.445 | 50.596 | -1.432 | 1.00 | 56.80 |
| 1148 | OG | SER | 249 | 23.488 | 49.267 | -1.938 | 1.00 | 58.69 |
| 1149 | HG | SER | 249 | 23.996 | 49.345 | -2.757 | 1.00 | 0.00 |
| 1150 | C | SER | 249 | 25.626 | 50.270 | -0.262 | 1.00 | 59.00 |
| 1151 | O | SER | 249 | 26.610 | 49.741 | -0.760 | 1.00 | 55.94 |
| 1152 | N | GLU | 250 | 25.285 | 50.003 | 0.982 | 1.00 | 68.05 |
| 1153 | H | GLU | 250 | 24.519 | 50.460 | 1.391 | 1.00 | 0.00 |
| 1154 | CA | GLU | 250 | 25.982 | 48.958 | 1.710 | 1.00 | 77.66 |
| 1155 | CB | GLU | 250 | 25.518 | 48.929 | 3.169 | 1.00 | 85.81 |
| 1156 | CG | GLU | 250 | 25.746 | 50.253 | 3.922 | 1.00 | 96.97 |
| 1157 | CD | GLU | 250 | 25.505 | 50.056 | 5.411 | 1.00 | 103.17 |
| 1158 | OE1 | GLU | 250 | 25.196 | 51.045 | 6.085 | 1.00 | 108.23 |
| 1159 | OE2 | GLU | 250 | 25.633 | 48.922 | 5.895 | 1.00 | 105.30 |

FIG. 500

| Atom | Atom Type | Residue | # | X | Y | Z | OCC | B |
|---|---|---|---|---|---|---|---|---|
| 1160 | C | GLU | 250 | 25.778 | 47.573 | 1.115 | 1.00 | 77.89 |
| 1161 | O | GLU | 250 | 26.649 | 46.720 | 1.119 | 1.00 | 78.08 |
| 1162 | N | GLN | 251 | 24.574 | 47.369 | 0.595 | 1.00 | 77.62 |
| 1163 | H | GLN | 251 | 23.971 | 48.135 | 0.546 | 1.00 | 0.00 |
| 1164 | CA | GLN | 251 | 24.155 | 46.078 | 0.085 | 1.00 | 77.63 |
| 1165 | CB | GLN | 251 | 22.616 | 45.902 | 0.224 | 1.00 | 86.21 |
| 1166 | CG | GLN | 251 | 21.677 | 47.096 | 0.015 | 1.00 | 97.44 |
| 1167 | CD | GLN | 251 | 21.754 | 48.076 | 1.182 | 1.00 | 106.14 |
| 1168 | OE1 | GLN | 251 | 22.556 | 49.005 | 1.219 | 1.00 | 112.85 |
| 1169 | NE2 | GLN | 251 | 20.940 | 47.965 | 2.214 | 1.00 | 108.86 |
| 1170 | HE21 | GLN | 251 | 20.288 | 47.236 | 2.234 | 1.00 | 0.00 |
| 1171 | HE22 | GLN | 251 | 21.031 | 48.635 | 2.926 | 1.00 | 0.00 |
| 1172 | C | GLN | 251 | 24.544 | 45.830 | -1.356 | 1.00 | 74.59 |
| 1173 | O | GLN | 251 | 24.771 | 44.704 | -1.778 | 1.00 | 73.25 |
| 1174 | N | VAL | 252 | 24.636 | 46.863 | -2.185 | 1.00 | 70.06 |
| 1175 | H | VAL | 252 | 24.241 | 47.718 | -1.911 | 1.00 | 0.00 |
| 1176 | CA | VAL | 252 | 25.375 | 46.711 | -3.425 | 1.00 | 66.24 |
| 1177 | CB | VAL | 252 | 24.482 | 46.902 | -4.657 | 1.00 | 68.01 |
| 1178 | CG1 | VAL | 252 | 25.271 | 47.177 | -5.941 | 1.00 | 67.58 |
| 1179 | CG2 | VAL | 252 | 23.711 | 45.600 | -4.832 | 1.00 | 71.77 |
| 1180 | C | VAL | 252 | 26.466 | 47.745 | -3.424 | 1.00 | 60.42 |
| 1181 | O | VAL | 252 | 26.282 | 48.961 | -3.409 | 1.00 | 57.54 |
| 1182 | N | PRO | 253 | 27.648 | 47.275 | -3.427 | 1.00 | 57.04 |
| 1183 | CD | PRO | 253 | 28.022 | 45.875 | -3.278 | 1.00 | 57.51 |
| 1184 | CA | PRO | 253 | 28.812 | 48.113 | -3.455 | 1.00 | 53.11 |
| 1185 | CB | PRO | 253 | 29.905 | 47.251 | -2.798 | 1.00 | 57.01 |
| 1186 | CG | PRO | 253 | 29.165 | 46.035 | -2.272 | 1.00 | 57.83 |
| 1187 | C | PRO | 253 | 29.113 | 48.551 | -4.866 | 1.00 | 47.52 |
| 1188 | O | PRO | 253 | 28.988 | 47.837 | -5.853 | 1.00 | 45.85 |

FIG. 5PP

| Atom | Atom Type | Residue | # | X | Y | Z | OCC | B |
|---|---|---|---|---|---|---|---|---|
| 1189 | N | ASP | 254 | 29.533 | 49.808 | -4.931 | 1.00 | 42.76 |
| 1190 | H | ASP | 254 | 29.509 | 50.376 | -4.143 | 1.00 | 0.00 |
| 1191 | CA | ASP | 254 | 30.038 | 50.374 | -6.156 | 1.00 | 38.48 |
| 1192 | CB | ASP | 254 | 29.051 | 51.461 | -6.580 | 1.00 | 36.32 |
| 1193 | CG | ASP | 254 | 29.341 | 51.949 | -7.979 | 1.00 | 36.27 |
| 1194 | OD1 | ASP | 254 | 28.990 | 53.090 | -8.264 | 1.00 | 39.87 |
| 1195 | OD2 | ASP | 254 | 29.903 | 51.204 | -8.786 | 1.00 | 36.65 |
| 1196 | C | ASP | 254 | 31.400 | 50.909 | -5.739 | 1.00 | 35.50 |
| 1197 | O | ASP | 254 | 31.506 | 52.050 | -5.321 | 1.00 | 34.98 |
| 1198 | N | ILE | 255 | 32.448 | 50.092 | -5.837 | 1.00 | 33.54 |
| 1199 | H | ILE | 255 | 32.350 | 49.250 | -6.329 | 1.00 | 0.00 |
| 1200 | CA | ILE | 255 | 33.761 | 50.400 | -5.307 | 1.00 | 35.65 |
| 1201 | CB | ILE | 255 | 34.181 | 49.317 | -4.295 | 1.00 | 39.66 |
| 1202 | CG2 | ILE | 255 | 35.615 | 49.605 | -3.797 | 1.00 | 40.81 |
| 1203 | CG1 | ILE | 255 | 33.157 | 49.254 | -3.144 | 1.00 | 39.28 |
| 1204 | CD1 | ILE | 255 | 32.955 | 50.590 | -2.435 | 1.00 | 40.52 |
| 1205 | C | ILE | 255 | 34.790 | 50.453 | -6.428 | 1.00 | 39.99 |
| 1206 | O | ILE | 255 | 34.826 | 49.556 | -7.258 | 1.00 | 40.26 |
| 1207 | N | LEU | 256 | 35.642 | 51.480 | -6.503 | 1.00 | 39.89 |
| 1208 | H | LEU | 256 | 35.471 | 52.284 | -5.964 | 1.00 | 0.00 |
| 1209 | CA | LEU | 256 | 36.831 | 51.410 | -7.340 | 1.00 | 39.66 |
| 1210 | CB | LEU | 256 | 37.066 | 52.755 | -8.074 | 1.00 | 38.42 |
| 1211 | CG | LEU | 256 | 38.298 | 52.842 | -8.988 | 1.00 | 37.25 |
| 1212 | CD1 | LEU | 256 | 38.214 | 51.825 | -10.115 | 1.00 | 36.68 |
| 1213 | CD2 | LEU | 256 | 38.377 | 54.245 | -9.571 | 1.00 | 39.39 |
| 1214 | C | LEU | 256 | 38.022 | 51.095 | -6.407 | 1.00 | 38.52 |
| 1215 | O | LEU | 256 | 38.368 | 51.793 | -5.455 | 1.00 | 40.24 |
| 1216 | N | GLN | 257 | 38.658 | 49.977 | -6.715 | 1.00 | 39.82 |
| 1217 | H | GLN | 257 | 38.308 | 49.468 | -7.488 | 1.00 | 0.00 |

FIG. 5QQ

| Atom | Atom Type | Residue | # | X | Y | Z | OCC | B |
|---|---|---|---|---|---|---|---|---|
| 1218 | CA | GLN | 257 | 39.795 | 49.436 | -5.992 | 1.00 | 42.81 |
| 1219 | CB | GLN | 257 | 40.050 | 48.020 | -6.455 | 1.00 | 49.86 |
| 1220 | CG | GLN | 257 | 40.720 | 47.077 | -5.487 | 1.00 | 62.03 |
| 1221 | CD | GLN | 257 | 39.707 | 46.054 | -5.046 | 1.00 | 66.77 |
| 1222 | OE1 | GLN | 257 | 38.568 | 46.361 | -4.726 | 1.00 | 70.03 |
| 1223 | NE2 | GLN | 257 | 40.013 | 44.767 | -5.063 | 1.00 | 67.84 |
| 1224 | HE21 | GLN | 257 | 40.897 | 44.483 | -5.369 | 1.00 | 0.00 |
| 1225 | HE22 | GLN | 257 | 39.295 | 44.174 | -4.752 | 1.00 | 0.00 |
| 1226 | C | GLN | 257 | 40.991 | 50.253 | -6.300 | 1.00 | 43.83 |
| 1227 | O | GLN | 257 | 41.296 | 50.526 | -7.457 | 1.00 | 44.09 |
| 1228 | N | LEU | 258 | 41.747 | 50.678 | -5.315 | 1.00 | 45.79 |
| 1229 | H | LEU | 258 | 41.461 | 50.433 | -4.414 | 1.00 | 0.00 |
| 1230 | CA | LEU | 258 | 42.951 | 51.468 | -5.556 | 1.00 | 48.19 |
| 1231 | CB | LEU | 258 | 43.638 | 51.714 | -4.187 | 1.00 | 62.23 |
| 1232 | CG | LEU | 258 | 45.178 | 51.726 | -4.015 | 1.00 | 71.72 |
| 1233 | CD1 | LEU | 258 | 45.742 | 53.135 | -3.795 | 1.00 | 65.86 |
| 1234 | CD2 | LEU | 258 | 45.495 | 50.830 | -2.809 | 1.00 | 80.83 |
| 1235 | C | LEU | 258 | 43.958 | 50.864 | -6.564 | 1.00 | 46.26 |
| 1236 | O | LEU | 258 | 44.583 | 51.564 | -7.368 | 1.00 | 43.62 |
| 1237 | N | ASN | 259 | 44.214 | 49.561 | -6.654 | 1.00 | 41.70 |
| 1238 | H | ASN | 259 | 43.687 | 48.856 | -6.205 | 1.00 | 0.00 |
| 1239 | CA | ASN | 259 | 45.197 | 49.203 | -7.648 | 1.00 | 41.88 |
| 1240 | CB | ASN | 259 | 46.029 | 48.071 | -7.151 | 1.00 | 46.19 |
| 1241 | CG | ASN | 259 | 45.376 | 46.750 | -7.280 | 1.00 | 49.87 |
| 1242 | OD1 | ASN | 259 | 44.187 | 46.674 | -7.008 | 1.00 | 56.41 |
| 1243 | ND2 | ASN | 259 | 46.115 | 45.710 | -7.644 | 1.00 | 50.33 |
| 1244 | HD21 | ASN | 259 | 47.075 | 45.857 | -7.810 | 1.00 | 0.00 |
| 1245 | HD22 | ASN | 259 | 45.682 | 44.830 | -7.714 | 1.00 | 0.00 |
| 1246 | C | ASN | 259 | 44.636 | 48.900 | -9.007 | 1.00 | 38.03 |

FIG. 5RR

| Atom | Atom Type | Residue | # | X | Y | Z | OCC | B |
|---|---|---|---|---|---|---|---|---|
| 1332 | HZ1 | LYS | 268 | 48.737 | 43.066 | -17.022 | 1.00 | 0.00 |
| 1333 | HZ2 | LYS | 268 | 47.453 | 42.877 | -18.122 | 1.00 | 0.00 |
| 1334 | HZ3 | LYS | 268 | 47.263 | 43.878 | -16.766 | 1.00 | 0.00 |
| 1335 | C | LYS | 268 | 50.013 | 48.367 | -20.803 | 1.00 | 34.09 |
| 1336 | O | LYS | 268 | 49.735 | 48.325 | -21.979 | 1.00 | 34.97 |
| 1337 | N | ASN | 269 | 49.267 | 49.054 | -19.948 | 1.00 | 29.59 |
| 1338 | H | ASN | 269 | 49.577 | 49.149 | -19.020 | 1.00 | 0.00 |
| 1339 | CA | ASN | 269 | 48.012 | 49.651 | -20.366 | 1.00 | 24.54 |
| 1340 | CB | ASN | 269 | 46.995 | 49.607 | -19.263 | 1.00 | 26.50 |
| 1341 | CG | ASN | 269 | 46.685 | 48.179 | -19.067 | 1.00 | 32.19 |
| 1342 | OD1 | ASN | 269 | 46.295 | 47.488 | -19.988 | 1.00 | 35.32 |
| 1343 | ND2 | ASN | 269 | 46.896 | 47.620 | -17.892 | 1.00 | 35.76 |
| 1344 | HD21 | ASN | 269 | 47.263 | 48.175 | -17.168 | 1.00 | 0.00 |
| 1345 | HD22 | ASN | 269 | 46.674 | 46.672 | -17.821 | 1.00 | 0.00 |
| 1346 | C | ASN | 269 | 48.130 | 51.078 | -20.767 | 1.00 | 27.02 |
| 1347 | O | ASN | 269 | 47.253 | 51.677 | -21.370 | 1.00 | 27.85 |
| 1348 | N | CYS | 270 | 49.228 | 51.744 | -20.458 | 1.00 | 26.07 |
| 1349 | H | CYS | 270 | 49.948 | 51.324 | -19.931 | 1.00 | 0.00 |
| 1350 | CA | CYS | 270 | 49.351 | 53.133 | -20.848 | 1.00 | 23.70 |
| 1351 | CB | CYS | 270 | 49.028 | 54.048 | -19.676 | 1.00 | 22.29 |
| 1352 | SG | CYS | 270 | 48.971 | 55.800 | -20.133 | 1.00 | 27.75 |
| 1353 | C | CYS | 270 | 50.770 | 53.374 | -21.287 | 1.00 | 26.34 |
| 1354 | O | CYS | 270 | 51.515 | 54.159 | -20.711 | 1.00 | 24.34 |
| 1355 | N | PRO | 271 | 51.237 | 52.761 | -22.313 | 1.00 | 26.04 |
| 1356 | CD | PRO | 271 | 50.428 | 52.006 | -23.263 | 1.00 | 26.80 |
| 1357 | CA | PRO | 271 | 52.628 | 52.860 | -22.730 | 1.00 | 26.32 |
| 1358 | CB | PRO | 271 | 52.694 | 51.997 | -23.974 | 1.00 | 25.30 |
| 1359 | CG | PRO | 271 | 51.292 | 52.036 | -24.514 | 1.00 | 24.28 |
| 1360 | C | PRO | 271 | 53.104 | 54.281 | -22.955 | 1.00 | 29.26 |
| 1361 | O | PRO | 271 | 54.259 | 54.644 | -22.776 | 1.00 | 31.29 |
| 1362 | N | SER | 272 | 52.220 | 55.180 | -23.365 | 1.00 | 30.94 |

FIG. 5SS

| Atom | Atom Type | Residue | # | X | Y | Z | OCC | B |
|---|---|---|---|---|---|---|---|---|
| 1276 | H | ASN | 263 | 46.219 | 49.470 | -11.496 | 1.00 | 0.00 |
| 1277 | CA | ASN | 263 | 46.827 | 48.683 | -13.372 | 1.00 | 32.07 |
| 1278 | CB | ASN | 263 | 45.872 | 47.495 | -13.119 | 1.00 | 36.54 |
| 1279 | CG | ASN | 263 | 46.483 | 46.467 | -12.141 | 1.00 | 48.06 |
| 1280 | OD1 | ASN | 263 | 47.677 | 46.416 | -11.842 | 1.00 | 52.97 |
| 1281 | ND2 | ASN | 263 | 45.694 | 45.600 | -11.517 | 1.00 | 50.97 |
| 1282 | HD21 | ASN | 263 | 44.728 | 45.639 | -11.681 | 1.00 | 0.00 |
| 1283 | HD22 | ASN | 263 | 46.129 | 44.947 | -10.928 | 1.00 | 0.00 |
| 1284 | C | ASN | 263 | 46.450 | 49.332 | -14.673 | 1.00 | 31.78 |
| 1285 | O | ASN | 263 | 47.043 | 49.081 | -15.715 | 1.00 | 30.44 |
| 1286 | N | MET | 264 | 45.443 | 50.203 | -14.640 | 1.00 | 30.71 |
| 1287 | H | MET | 264 | 44.940 | 50.348 | -13.807 | 1.00 | 0.00 |
| 1288 | CA | MET | 264 | 45.054 | 50.956 | -15.817 | 1.00 | 31.45 |
| 1289 | CB | MET | 264 | 43.742 | 51.698 | -15.565 | 1.00 | 36.38 |
| 1290 | CG | MET | 264 | 42.552 | 50.779 | -15.835 | 1.00 | 44.27 |
| 1291 | SD | MET | 264 | 40.953 | 51.627 | -15.768 | 1.00 | 51.17 |
| 1292 | CE | MET | 264 | 40.447 | 51.015 | -14.191 | 1.00 | 51.48 |
| 1293 | C | MET | 264 | 46.036 | 51.979 | -16.362 | 1.00 | 30.63 |
| 1294 | O | MET | 264 | 45.903 | 52.396 | -17.500 | 1.00 | 25.16 |
| 1295 | N | LEU | 265 | 47.044 | 52.435 | -15.617 | 1.00 | 27.60 |
| 1296 | H | LEU | 265 | 47.167 | 52.116 | -14.695 | 1.00 | 0.00 |
| 1297 | CA | LEU | 265 | 47.941 | 53.456 | -16.133 | 1.00 | 23.27 |
| 1298 | CB | LEU | 265 | 47.844 | 54.709 | -15.272 | 1.00 | 24.95 |
| 1299 | CG | LEU | 265 | 46.508 | 55.432 | -15.452 | 1.00 | 30.77 |
| 1300 | CD1 | LEU | 265 | 45.942 | 55.833 | -14.099 | 1.00 | 35.13 |
| 1301 | CD2 | LEU | 265 | 46.722 | 56.641 | -16.339 | 1.00 | 30.86 |
| 1302 | C | LEU | 265 | 49.365 | 52.980 | -16.157 | 1.00 | 21.55 |
| 1303 | O | LEU | 265 | 50.309 | 53.724 | -16.327 | 1.00 | 21.21 |
| 1304 | N | ASN | 266 | 49.583 | 51.696 | -15.972 | 1.00 | 20.49 |

FIG. 5TT

| Atom | Atom Type | Residue | # | X | Y | Z | OCC | B |
|---|---|---|---|---|---|---|---|---|
| 1305 | H | ASN | 266 | 48.832 | 51.117 | -15.737 | 1.00 | 0.00 |
| 1306 | CA | ASN | 266 | 50.918 | 51.154 | -16.072 | 1.00 | 21.68 |
| 1307 | CB | ASN | 266 | 50.905 | 49.810 | -15.355 | 1.00 | 20.66 |
| 1308 | CG | ASN | 266 | 50.208 | 48.692 | -16.103 | 1.00 | 26.15 |
| 1309 | OD1 | ASN | 266 | 50.004 | 48.725 | -17.302 | 1.00 | 30.13 |
| 1310 | ND2 | ASN | 266 | 49.889 | 47.599 | -15.435 | 1.00 | 26.18 |
| 1311 | HD21 | ASN | 266 | 50.148 | 47.527 | -14.492 | 1.00 | 0.00 |
| 1312 | HD22 | ASN | 266 | 49.389 | 46.885 | -15.880 | 1.00 | 0.00 |
| 1313 | C | ASN | 266 | 51.463 | 51.028 | -17.496 | 1.00 | 27.52 |
| 1314 | O | ASN | 266 | 50.834 | 51.391 | -18.480 | 1.00 | 25.25 |
| 1315 | N | THR | 267 | 52.671 | 50.496 | -17.668 | 1.00 | 29.62 |
| 1316 | H | THR | 267 | 53.155 | 50.095 | -16.911 | 1.00 | 0.00 |
| 1317 | CA | THR | 267 | 53.325 | 50.491 | -18.965 | 1.00 | 31.01 |
| 1318 | CB | THR | 267 | 54.807 | 50.073 | -18.787 | 1.00 | 31.03 |
| 1319 | OG1 | THR | 267 | 55.330 | 51.030 | -17.858 | 1.00 | 36.10 |
| 1320 | HG1 | THR | 267 | 54.960 | 50.998 | -16.964 | 1.00 | 0.00 |
| 1321 | CG2 | THR | 267 | 55.686 | 50.139 | -20.052 | 1.00 | 28.06 |
| 1322 | C | THR | 267 | 52.618 | 49.591 | -19.933 | 1.00 | 31.70 |
| 1323 | O | THR | 267 | 52.606 | 49.803 | -21.128 | 1.00 | 31.87 |
| 1324 | N | LYS | 268 | 51.988 | 48.543 | -19.427 | 1.00 | 34.40 |
| 1325 | H | LYS | 268 | 52.010 | 48.391 | -18.464 | 1.00 | 0.00 |
| 1326 | CA | LYS | 268 | 51.228 | 47.643 | -20.275 | 1.00 | 34.41 |
| 1327 | CB | LYS | 268 | 50.800 | 46.427 | -19.458 | 1.00 | 38.03 |
| 1328 | CG | LYS | 268 | 49.912 | 45.417 | -20.194 | 1.00 | 46.78 |
| 1329 | CD | LYS | 268 | 49.406 | 44.239 | -19.341 | 1.00 | 51.28 |
| 1330 | CE | LYS | 268 | 48.410 | 44.674 | -18.258 | 1.00 | 59.23 |
| 1331 | NZ | LYS | 268 | 47.936 | 43.541 | -17.483 | 1.00 | 63.39 |
| 1332 | HZ1 | LYS | 268 | 48.737 | 43.066 | -17.022 | 1.00 | 0.00 |
| 1333 | HZ2 | LYS | 268 | 47.453 | 42.877 | -18.122 | 1.00 | 0.00 |

FIG. 5UU

| Atom | Atom Type | Residue | # | X | Y | Z | OCC | B |
|---|---|---|---|---|---|---|---|---|
| 1334 | HZ3 | LYS | 268 | 47.263 | 43.878 | -16.766 | 1.00 | 0.00 |
| 1335 | C | LYS | 268 | 50.013 | 48.367 | -20.803 | 1.00 | 34.09 |
| 1336 | O | LYS | 268 | 49.735 | 48.325 | -21.979 | 1.00 | 34.97 |
| 1337 | N | ASN | 269 | 49.267 | 49.054 | -19.948 | 1.00 | 29.59 |
| 1338 | H | ASN | 269 | 49.577 | 49.149 | -19.020 | 1.00 | 0.00 |
| 1339 | CA | ASN | 269 | 48.012 | 49.651 | -20.366 | 1.00 | 24.54 |
| 1340 | CB | ASN | 269 | 46.995 | 49.607 | -19.263 | 1.00 | 26.50 |
| 1341 | CG | ASN | 269 | 46.685 | 48.179 | -19.067 | 1.00 | 32.19 |
| 1342 | OD1 | ASN | 269 | 46.295 | 47.488 | -19.988 | 1.00 | 35.32 |
| 1343 | ND2 | ASN | 269 | 46.896 | 47.620 | -17.892 | 1.00 | 35.76 |
| 1344 | HD21 | ASN | 269 | 47.263 | 48.175 | -17.168 | 1.00 | 0.00 |
| 1345 | HD22 | ASN | 269 | 46.674 | 46.672 | -17.821 | 1.00 | 0.00 |
| 1346 | C | ASN | 269 | 48.130 | 51.078 | -20.767 | 1.00 | 27.02 |
| 1347 | O | ASN | 269 | 47.253 | 51.677 | -21.370 | 1.00 | 27.85 |
| 1348 | N | CYS | 270 | 49.228 | 51.744 | -20.458 | 1.00 | 26.07 |
| 1349 | H | CYS | 270 | 49.948 | 51.324 | -19.931 | 1.00 | 0.00 |
| 1350 | CA | CYS | 270 | 49.351 | 53.133 | -20.848 | 1.00 | 23.70 |
| 1351 | CB | CYS | 270 | 49.028 | 54.048 | -19.676 | 1.00 | 22.29 |
| 1352 | SG | CYS | 270 | 48.971 | 55.800 | -20.133 | 1.00 | 27.75 |
| 1353 | C | CYS | 270 | 50.770 | 53.374 | -21.287 | 1.00 | 26.34 |
| 1354 | O | CYS | 270 | 51.515 | 54.159 | -20.711 | 1.00 | 24.34 |
| 1355 | N | PRO | 271 | 51.237 | 52.761 | -22.313 | 1.00 | 26.04 |
| 1356 | CD | PRO | 271 | 50.428 | 52.006 | -23.263 | 1.00 | 26.80 |
| 1357 | CA | PRO | 271 | 52.628 | 52.860 | -22.730 | 1.00 | 26.32 |
| 1358 | CB | PRO | 271 | 52.694 | 51.997 | -23.974 | 1.00 | 25.30 |
| 1359 | CG | PRO | 271 | 51.292 | 52.036 | -24.514 | 1.00 | 24.28 |
| 1360 | C | PRO | 271 | 53.104 | 54.281 | -22.955 | 1.00 | 29.26 |
| 1361 | O | PRO | 271 | 54.259 | 54.644 | -22.776 | 1.00 | 31.29 |
| 1362 | N | SER | 272 | 52.220 | 55.180 | -23.365 | 1.00 | 30.94 |

FIG. 5VV

| Atom | Atom Type | Residue | # | X | Y | Z | OCC | B |
|---|---|---|---|---|---|---|---|---|
| 1363 | H | SER | 272 | 51.287 | 54.942 | -23.574 | 1.00 | 0.00 |
| 1364 | CA | SER | 272 | 52.617 | 56.555 | -23.545 | 1.00 | 31.44 |
| 1365 | CB | SER | 272 | 51.440 | 57.305 | -24.135 | 1.00 | 37.05 |
| 1366 | OG | SER | 272 | 50.225 | 56.635 | -23.790 | 1.00 | 53.17 |
| 1367 | HG | SER | 272 | 50.053 | 56.659 | -22.840 | 1.00 | 0.00 |
| 1368 | C | SER | 272 | 53.068 | 57.208 | -22.269 | 1.00 | 30.10 |
| 1369 | O | SER | 272 | 53.666 | 58.259 | -22.345 | 1.00 | 30.70 |
| 1370 | N | LEU | 273 | 52.826 | 56.687 | -21.064 | 1.00 | 29.16 |
| 1371 | H | LEU | 273 | 52.343 | 55.839 | -20.921 | 1.00 | 0.00 |
| 1372 | CA | LEU | 273 | 53.350 | 57.384 | -19.910 | 1.00 | 26.90 |
| 1373 | CB | LEU | 273 | 52.250 | 57.567 | -18.851 | 1.00 | 23.25 |
| 1374 | CG | LEU | 273 | 51.343 | 58.788 | -19.139 | 1.00 | 24.56 |
| 1375 | CD1 | LEU | 273 | 50.112 | 58.798 | -18.225 | 1.00 | 20.80 |
| 1376 | CD2 | LEU | 273 | 52.168 | 60.056 | -18.965 | 1.00 | 20.75 |
| 1377 | C | LEU | 273 | 54.519 | 56.632 | -19.336 | 1.00 | 28.09 |
| 1378 | O | LEU | 273 | 54.948 | 56.803 | -18.205 | 1.00 | 24.97 |
| 1379 | N | LYS | 274 | 55.108 | 55.731 | -20.112 | 1.00 | 28.29 |
| 1380 | H | LYS | 274 | 54.753 | 55.544 | -21.008 | 1.00 | 0.00 |
| 1381 | CA | LYS | 274 | 56.314 | 55.053 | -19.684 | 1.00 | 27.08 |
| 1382 | CB | LYS | 274 | 56.853 | 54.212 | -20.819 | 1.00 | 28.08 |
| 1383 | CG | LYS | 274 | 58.111 | 53.417 | -20.485 | 1.00 | 32.44 |
| 1384 | CD | LYS | 274 | 58.619 | 52.783 | -21.777 | 1.00 | 40.58 |
| 1385 | CE | LYS | 274 | 59.960 | 52.073 | -21.658 | 1.00 | 45.30 |
| 1386 | NZ | LYS | 274 | 61.040 | 53.035 | -21.669 | 1.00 | 47.25 |
| 1387 | HZ1 | LYS | 274 | 60.925 | 53.685 | -20.867 | 1.00 | 0.00 |
| 1388 | HZ2 | LYS | 274 | 61.021 | 53.571 | -22.560 | 1.00 | 0.00 |
| 1389 | HZ3 | LYS | 274 | 61.949 | 52.537 | -21.580 | 1.00 | 0.00 |
| 1390 | C | LYS | 274 | 57.348 | 56.087 | -19.285 | 1.00 | 27.81 |
| 1391 | O | LYS | 274 | 57.594 | 57.057 | -19.983 | 1.00 | 27.52 |

FIG. 5WW

| Atom | Atom Type | Residue | # | X | Y | Z | OCC | B |
|---|---|---|---|---|---|---|---|---|
| 1392 | N | ASP | 275 | 57.942 | 55.858 | -18.123 | 1.00 | 26.78 |
| 1393 | H | ASP | 275 | 57.514 | 55.152 | -17.599 | 1.00 | 0.00 |
| 1394 | CA | ASP | 275 | 59.007 | 56.689 | -17.546 | 1.00 | 24.40 |
| 1395 | CB | ASP | 275 | 60.222 | 56.827 | -18.507 | 1.00 | 24.70 |
| 1396 | CG | ASP | 275 | 60.849 | 55.482 | -18.831 | 1.00 | 28.62 |
| 1397 | OD1 | ASP | 275 | 61.282 | 55.358 | -19.970 | 1.00 | 35.31 |
| 1398 | OD2 | ASP | 275 | 60.919 | 54.577 | -17.980 | 1.00 | 31.34 |
| 1399 | C | ASP | 275 | 58.618 | 58.090 | -17.114 | 1.00 | 21.07 |
| 1400 | O | ASP | 275 | 59.450 | 58.931 | -16.787 | 1.00 | 22.30 |
| 1401 | N | LYS | 276 | 57.332 | 58.409 | -17.087 | 1.00 | 20.11 |
| 1402 | H | LYS | 276 | 56.635 | 57.754 | -17.318 | 1.00 | 0.00 |
| 1403 | CA | LYS | 276 | 56.918 | 59.738 | -16.690 | 1.00 | 20.03 |
| 1404 | CB | LYS | 276 | 55.977 | 60.268 | -17.772 | 1.00 | 15.62 |
| 1405 | CG | LYS | 276 | 56.700 | 60.352 | -19.129 | 1.00 | 20.79 |
| 1406 | CD | LYS | 276 | 55.762 | 60.741 | -20.275 | 1.00 | 25.10 |
| 1407 | CE | LYS | 276 | 56.341 | 60.584 | -21.682 | 1.00 | 24.43 |
| 1408 | NZ | LYS | 276 | 55.317 | 60.858 | -22.677 | 1.00 | 26.93 |
| 1409 | HZ1 | LYS | 276 | 54.962 | 61.828 | -22.562 | 1.00 | 0.00 |
| 1410 | HZ2 | LYS | 276 | 54.528 | 60.192 | -22.550 | 1.00 | 0.00 |
| 1411 | HZ3 | LYS | 276 | 55.716 | 60.744 | -23.630 | 1.00 | 0.00 |
| 1412 | C | LYS | 276 | 56.238 | 59.664 | -15.339 | 1.00 | 21.33 |
| 1413 | O | LYS | 276 | 55.549 | 58.696 | -15.080 | 1.00 | 23.74 |
| 1414 | N | PRO | 277 | 56.342 | 60.565 | -14.432 | 1.00 | 18.25 |
| 1415 | CD | PRO | 277 | 57.125 | 61.779 | -14.555 | 1.00 | 20.11 |
| 1416 | CA | PRO | 277 | 55.658 | 60.491 | -13.158 | 1.00 | 19.61 |
| 1417 | CB | PRO | 277 | 56.178 | 61.665 | -12.348 | 1.00 | 19.47 |
| 1418 | CG | PRO | 277 | 57.365 | 62.160 | -13.113 | 1.00 | 17.30 |
| 1419 | C | PRO | 277 | 54.146 | 60.506 | -13.252 | 1.00 | 21.46 |
| 1420 | O | PRO | 277 | 53.522 | 61.268 | -13.988 | 1.00 | 24.07 |

FIG. 5XX

| Atom | Atom Type | Residue | # | X | Y | Z | OCC | B |
|---|---|---|---|---|---|---|---|---|
| 1421 | N | LYS | 278 | 53.531 | 59.642 | -12.473 | 1.00 | 19.22 |
| 1422 | H | LYS | 278 | 54.049 | 58.986 | -11.955 | 1.00 | 0.00 |
| 1423 | CA | LYS | 278 | 52.093 | 59.598 | -12.436 | 1.00 | 18.47 |
| 1424 | CB | LYS | 278 | 51.654 | 58.233 | -12.953 | 1.00 | 16.94 |
| 1425 | CG | LYS | 278 | 52.074 | 58.090 | -14.435 | 1.00 | 15.20 |
| 1426 | CD | LYS | 278 | 51.919 | 56.673 | -14.945 | 1.00 | 16.03 |
| 1427 | CE | LYS | 278 | 53.057 | 55.723 | -14.550 | 1.00 | 18.36 |
| 1428 | NZ | LYS | 278 | 54.258 | 55.975 | -15.318 | 1.00 | 19.84 |
| 1429 | HZ1 | LYS | 278 | 54.573 | 56.952 | -15.158 | 1.00 | 0.00 |
| 1430 | HZ2 | LYS | 278 | 54.052 | 55.841 | -16.328 | 1.00 | 0.00 |
| 1431 | HZ3 | LYS | 278 | 55.008 | 55.317 | -15.025 | 1.00 | 0.00 |
| 1432 | C | LYS | 278 | 51.698 | 59.807 | -11.016 | 1.00 | 21.76 |
| 1433 | O | LYS | 278 | 51.903 | 58.916 | -10.202 | 1.00 | 23.16 |
| 1434 | N | VAL | 279 | 51.133 | 60.956 | -10.655 | 1.00 | 18.92 |
| 1435 | H | VAL | 279 | 50.893 | 61.619 | -11.338 | 1.00 | 0.00 |
| 1436 | CA | VAL | 279 | 50.830 | 61.249 | -9.270 | 1.00 | 16.68 |
| 1437 | CB | VAL | 279 | 51.262 | 62.707 | -8.960 | 1.00 | 15.16 |
| 1438 | CG1 | VAL | 279 | 51.042 | 63.041 | -7.484 | 1.00 | 12.89 |
| 1439 | CG2 | VAL | 279 | 52.737 | 62.882 | -9.318 | 1.00 | 13.20 |
| 1440 | C | VAL | 279 | 49.340 | 61.054 | -9.066 | 1.00 | 20.13 |
| 1441 | O | VAL | 279 | 48.520 | 61.647 | -9.770 | 1.00 | 20.96 |
| 1442 | N | ILE | 280 | 48.946 | 60.212 | -8.099 | 1.00 | 20.07 |
| 1443 | H | ILE | 280 | 49.628 | 59.772 | -7.543 | 1.00 | 0.00 |
| 1444 | CA | ILE | 280 | 47.535 | 59.939 | -7.830 | 1.00 | 20.53 |
| 1445 | CB | ILE | 280 | 47.306 | 58.401 | -7.914 | 1.00 | 25.21 |
| 1446 | CG2 | ILE | 280 | 45.900 | 58.000 | -7.454 | 1.00 | 17.77 |
| 1447 | CG1 | ILE | 280 | 47.519 | 57.977 | -9.377 | 1.00 | 24.13 |
| 1448 | CD1 | ILE | 280 | 48.045 | 56.562 | -9.513 | 1.00 | 30.13 |
| 1449 | C | ILE | 280 | 47.150 | 60.496 | -6.467 | 1.00 | 21.62 |

FIG. 5YY

| Atom | Atom Type | Residue | # | X | Y | Z | OCC | B |
|---|---|---|---|---|---|---|---|---|
| 1450 | O | ILE | 280 | 47.789 | 60.204 | -5.464 | 1.00 | 22.51 |
| 1451 | N | ILE | 281 | 46.108 | 61.318 | -6.363 | 1.00 | 20.14 |
| 1452 | H | ILE | 281 | 45.542 | 61.495 | -7.148 | 1.00 | 0.00 |
| 1453 | CA | ILE | 281 | 45.770 | 61.940 | -5.109 | 1.00 | 19.43 |
| 1454 | CB | ILE | 281 | 45.858 | 63.465 | -5.300 | 1.00 | 19.82 |
| 1455 | CG2 | ILE | 281 | 45.338 | 64.229 | -4.081 | 1.00 | 16.34 |
| 1456 | CG1 | ILE | 281 | 47.333 | 63.810 | -5.516 | 1.00 | 24.03 |
| 1457 | CD1 | ILE | 281 | 47.627 | 65.269 | -5.781 | 1.00 | 26.46 |
| 1458 | C | ILE | 281 | 44.389 | 61.476 | -4.737 | 1.00 | 22.29 |
| 1459 | O | ILE | 281 | 43.495 | 61.498 | -5.568 | 1.00 | 21.67 |
| 1460 | N | ILE | 282 | 44.128 | 61.032 | -3.509 | 1.00 | 23.39 |
| 1461 | H | ILE | 282 | 44.833 | 61.012 | -2.823 | 1.00 | 0.00 |
| 1462 | CA | ILE | 282 | 42.781 | 60.593 | -3.163 | 1.00 | 24.32 |
| 1463 | CB | ILE | 282 | 42.761 | 59.050 | -3.045 | 1.00 | 21.45 |
| 1464 | CG2 | ILE | 282 | 41.368 | 58.517 | -2.706 | 1.00 | 22.39 |
| 1465 | CG1 | ILE | 282 | 43.224 | 58.492 | -4.387 | 1.00 | 17.29 |
| 1466 | CD1 | ILE | 282 | 43.645 | 57.044 | -4.387 | 1.00 | 18.62 |
| 1467 | C | ILE | 282 | 42.275 | 61.214 | -1.878 | 1.00 | 24.17 |
| 1468 | O | ILE | 282 | 42.837 | 61.022 | -0.802 | 1.00 | 23.02 |
| 1469 | N | GLN | 283 | 41.195 | 61.985 | -1.981 | 1.00 | 24.17 |
| 1470 | H | GLN | 283 | 40.880 | 62.229 | -2.879 | 1.00 | 0.00 |
| 1471 | CA | GLN | 283 | 40.417 | 62.361 | -0.807 | 1.00 | 26.94 |
| 1472 | CB | GLN | 283 | 39.916 | 63.809 | -0.951 | 1.00 | 29.78 |
| 1473 | CG | GLN | 283 | 38.790 | 64.295 | -0.003 | 1.00 | 30.76 |
| 1474 | CD | GLN | 283 | 39.213 | 64.338 | 1.454 | 1.00 | 31.96 |
| 1475 | OE1 | GLN | 283 | 40.263 | 64.820 | 1.835 | 1.00 | 26.84 |
| 1476 | NE2 | GLN | 283 | 38.367 | 63.923 | 2.370 | 1.00 | 32.78 |
| 1477 | HE21 | GLN | 283 | 37.468 | 63.628 | 2.058 | 1.00 | 0.00 |
| 1478 | HE22 | GLN | 283 | 38.632 | 63.911 | 3.299 | 1.00 | 0.00 |

FIG. 5ZZ

| Atom | Atom Type | Residue | # | X | Y | Z | OCC | B |
|---|---|---|---|---|---|---|---|---|
| 1479 | C | GLN | 283 | 39.227 | 61.397 | -0.673 | 1.00 | 27.75 |
| 1480 | O | GLN | 283 | 38.396 | 61.282 | -1.580 | 1.00 | 27.45 |
| 1481 | N | ALA | 284 | 39.127 | 60.692 | 0.460 | 1.00 | 24.57 |
| 1482 | H | ALA | 284 | 39.827 | 60.742 | 1.148 | 1.00 | 0.00 |
| 1483 | CA | ALA | 284 | 38.115 | 59.682 | 0.688 | 1.00 | 22.92 |
| 1484 | CB | ALA | 284 | 38.196 | 58.595 | -0.383 | 1.00 | 15.36 |
| 1485 | C | ALA | 284 | 38.438 | 59.060 | 2.029 | 1.00 | 25.81 |
| 1486 | O | ALA | 284 | 39.598 | 58.871 | 2.387 | 1.00 | 29.97 |
| 1487 | N | ALD | 285 | 37.396 | 58.754 | 2.795 | 1.00 | 27.43 |
| 1488 | CA | ALD | 285 | 37.538 | 58.081 | 4.104 | 1.00 | 26.59 |
| 1489 | C | ALD | 285 | 38.038 | 56.689 | 3.860 | 1.00 | 26.61 |
| 1490 | O | ALD | 285 | 37.779 | 56.155 | 2.790 | 1.00 | 30.02 |
| 1491 | CB | ALD | 285 | 36.215 | 57.908 | 4.846 | 1.00 | 26.43 |
| 1492 | SG | ALD | 285 | 35.603 | 59.475 | 5.487 | 1.00 | 34.69 |
| 1493 | N1 | ALD | 285 | 32.516 | 69.905 | 10.851 | 1.00 | 58.66 |
| 1494 | C1 | ALD | 285 | 33.306 | 68.911 | 10.160 | 1.00 | 48.23 |
| 1495 | C5 | ALD | 285 | 32.529 | 67.649 | 10.069 | 1.00 | 45.89 |
| 1496 | O2 | ALD | 285 | 31.833 | 67.247 | 10.983 | 1.00 | 47.20 |
| 1497 | C9 | ALD | 285 | 34.623 | 68.691 | 10.902 | 1.00 | 46.18 |
| 1498 | CG | ALD | 285 | 35.549 | 69.731 | 10.350 | 1.00 | 50.40 |
| 1499 | CD1 | ALD | 285 | 35.586 | 71.002 | 10.923 | 1.00 | 53.28 |
| 1500 | CD2 | ALD | 285 | 36.268 | 69.456 | 9.185 | 1.00 | 53.34 |
| 1501 | CE1 | ALD | 285 | 36.376 | 71.984 | 10.326 | 1.00 | 55.15 |
| 1502 | CE2 | ALD | 285 | 37.056 | 70.446 | 8.595 | 1.00 | 52.67 |
| 1503 | CZ | ALD | 285 | 37.109 | 71.725 | 9.163 | 1.00 | 57.31 |
| 1504 | OH | ALD | 285 | 37.756 | 72.792 | 8.546 | 1.00 | 63.58 |
| 1505 | N2 | ALD | 285 | 32.657 | 67.034 | 8.925 | 1.00 | 38.70 |
| 1506 | C2 | ALD | 285 | 31.932 | 65.809 | 8.702 | 1.00 | 34.11 |
| 1507 | C6 | ALD | 285 | 33.033 | 64.915 | 8.206 | 1.00 | 33.25 |

FIG. 5AAA

| Atom | Atom Type | Residue | # | X | Y | Z | OCC | B |
|---|---|---|---|---|---|---|---|---|
| 1508 | O3 | ALD | 285 | 34.021 | 65.383 | 7.657 | 1.00 | 27.84 |
| 1509 | C10 | ALD | 285 | 30.819 | 66.116 | 7.661 | 1.00 | 39.67 |
| 1510 | CG1 | ALD | 285 | 30.399 | 64.915 | 6.822 | 1.00 | 44.49 |
| 1511 | CG2 | ALD | 285 | 29.588 | 66.547 | 8.453 | 1.00 | 40.46 |
| 1512 | N3 | ALD | 285 | 32.851 | 63.630 | 8.422 | 1.00 | 31.01 |
| 1513 | C3 | ALD | 285 | 33.824 | 62.646 | 7.997 | 1.00 | 33.50 |
| 1514 | C7 | ALD | 285 | 33.316 | 62.147 | 6.681 | 1.00 | 37.64 |
| 1515 | O4 | ALD | 285 | 32.114 | 62.219 | 6.432 | 1.00 | 44.05 |
| 1516 | C11 | ALD | 285 | 33.899 | 61.464 | 8.952 | 1.00 | 31.45 |
| 1517 | N4 | ALD | 285 | 34.265 | 61.650 | 5.908 | 1.00 | 35.48 |
| 1518 | C4 | ALD | 285 | 34.210 | 61.553 | 4.464 | 1.00 | 33.98 |
| 1519 | C8 | ALD | 285 | 34.763 | 60.203 | 4.008 | 1.00 | 36.52 |
| 1520 | C12 | ALD | 285 | 35.030 | 62.710 | 3.971 | 1.00 | 35.04 |
| 1521 | C13 | ALD | 285 | 34.835 | 62.936 | 2.510 | 1.00 | 37.05 |
| 1522 | OD1 | ALD | 285 | 35.766 | 63.453 | 1.898 | 1.00 | 37.30 |
| 1523 | OD2 | ALD | 285 | 33.772 | 62.594 | 1.993 | 1.00 | 34.87 |
| 1524 | O5 | ALD | 285 | 33.751 | 59.337 | 3.478 | 1.00 | 42.82 |
| 1525 | H1 | ALD | 285 | 36.497 | 58.977 | 2.418 | 1.00 | 0.00 |
| 1526 | C14 | ALD | 285 | 31.983 | 70.803 | 10.042 | 1.00 | 65.26 |
| 1527 | H5 | ALD | 285 | 32.384 | 69.885 | 11.844 | 1.00 | 0.00 |
| 1528 | H6 | ALD | 285 | 37.739 | 72.711 | 7.587 | 1.00 | 0.00 |
| 1529 | H7 | ALD | 285 | 33.249 | 67.364 | 8.179 | 1.00 | 0.00 |
| 1530 | H8 | ALD | 285 | 32.004 | 63.310 | 8.842 | 1.00 | 0.00 |
| 1531 | H9 | ALD | 285 | 35.098 | 61.322 | 6.347 | 1.00 | 0.00 |
| 1532 | C15 | ALD | 285 | 30.476 | 70.799 | 10.002 | 1.00 | 65.03 |
| 1533 | O1 | ALD | 285 | 32.684 | 71.569 | 9.386 | 1.00 | 73.24 |
| 1534 | H2 | ALD | 285 | 35.481 | 60.411 | 3.215 | 1.00 | 0.00 |
| 1535 | N | ARG | 286 | 38.740 | 56.061 | 4.793 | 1.00 | 26.38 |
| 1536 | H | ARG | 286 | 38.960 | 56.493 | 5.651 | 1.00 | 0.00 |

FIG. 5BBB

| Atom | Atom Type | Residue | # | X | Y | Z | OCC | B |
|---|---|---|---|---|---|---|---|---|
| 1537 | CA | ARG | 286 | 39.231 | 54.719 | 4.550 | 1.00 | 25.85 |
| 1538 | CB | ARG | 286 | 40.747 | 54.692 | 4.682 | 1.00 | 24.02 |
| 1539 | CG | ARG | 286 | 41.387 | 55.701 | 3.739 | 1.00 | 23.75 |
| 1540 | CD | ARG | 286 | 42.430 | 54.961 | 2.926 | 1.00 | 27.07 |
| 1541 | NE | ARG | 286 | 43.768 | 55.251 | 3.356 | 1.00 | 29.64 |
| 1542 | HE | ARG | 286 | 43.926 | 55.944 | 4.031 | 1.00 | 0.00 |
| 1543 | CZ | ARG | 286 | 44.798 | 54.588 | 2.845 | 1.00 | 26.29 |
| 1544 | NH1 | ARG | 286 | 46.050 | 55.018 | 3.144 | 1.00 | 25.89 |
| 1545 | HH11 | ARG | 286 | 46.181 | 55.814 | 3.735 | 1.00 | 0.00 |
| 1546 | HH12 | ARG | 286 | 46.845 | 54.538 | 2.774 | 1.00 | 0.00 |
| 1547 | NH2 | ARG | 286 | 44.621 | 53.491 | 2.058 | 1.00 | 19.53 |
| 1548 | HH21 | ARG | 286 | 43.700 | 53.161 | 1.851 | 1.00 | 0.00 |
| 1549 | HH22 | ARG | 286 | 45.416 | 53.010 | 1.689 | 1.00 | 0.00 |
| 1550 | C | ARG | 286 | 38.629 | 53.755 | 5.538 | 1.00 | 26.43 |
| 1551 | O | ARG | 286 | 39.160 | 52.683 | 5.803 | 1.00 | 27.12 |
| 1552 | N | GLY | 287 | 37.495 | 54.113 | 6.133 | 1.00 | 26.73 |
| 1553 | H | GLY | 287 | 37.021 | 54.925 | 5.843 | 1.00 | 0.00 |
| 1554 | CA | GLY | 287 | 36.905 | 53.350 | 7.208 | 1.00 | 27.46 |
| 1555 | C | GLY | 287 | 36.162 | 54.330 | 8.100 | 1.00 | 30.03 |
| 1556 | O | GLY | 287 | 35.932 | 55.475 | 7.728 | 1.00 | 32.06 |
| 1557 | N | ASP | 288 | 35.804 | 53.848 | 9.292 | 1.00 | 33.55 |
| 1558 | H | ASP | 288 | 36.263 | 53.019 | 9.545 | 1.00 | 0.00 |
| 1559 | CA | ASP | 288 | 34.941 | 54.525 | 10.273 | 1.00 | 32.84 |
| 1560 | CB | ASP | 288 | 33.839 | 53.609 | 10.820 | 1.00 | 40.57 |
| 1561 | CG | ASP | 288 | 33.043 | 52.985 | 9.706 | 1.00 | 48.86 |
| 1562 | OD1 | ASP | 288 | 33.051 | 51.752 | 9.612 | 1.00 | 53.99 |
| 1563 | OD2 | ASP | 288 | 32.413 | 53.731 | 8.944 | 1.00 | 51.26 |
| 1564 | C | ASP | 288 | 35.710 | 55.003 | 11.500 | 1.00 | 31.98 |
| 1565 | O | ASP | 288 | 35.283 | 55.884 | 12.250 | 1.00 | 32.42 |

FIG. 5CCC

| Atom | Atom Type | Residue | # | X | Y | Z | OCC | B |
|---|---|---|---|---|---|---|---|---|
| 1566 | N | SER | 289 | 36.884 | 54.437 | 11.775 | 1.00 | 28.78 |
| 1567 | H | SER | 289 | 37.321 | 53.757 | 11.200 | 1.00 | 0.00 |
| 1568 | CA | SER | 289 | 37.596 | 54.805 | 12.969 | 1.00 | 24.44 |
| 1569 | CB | SER | 289 | 38.704 | 53.801 | 13.071 | 1.00 | 22.45 |
| 1570 | OG | SER | 289 | 38.083 | 52.535 | 13.042 | 1.00 | 33.26 |
| 1571 | HG | SER | 289 | 38.773 | 51.861 | 13.003 | 1.00 | 0.00 |
| 1572 | C | SER | 289 | 38.069 | 56.239 | 12.940 | 1.00 | 24.99 |
| 1573 | O | SER | 289 | 38.394 | 56.809 | 11.907 | 1.00 | 26.10 |
| 1574 | N | PRO | 290 | 38.143 | 56.885 | 14.041 | 1.00 | 27.20 |
| 1575 | CD | PRO | 290 | 37.408 | 56.497 | 15.249 | 1.00 | 22.52 |
| 1576 | CA | PRO | 290 | 38.631 | 58.270 | 14.136 | 1.00 | 25.66 |
| 1577 | CB | PRO | 290 | 38.051 | 58.769 | 15.454 | 1.00 | 27.04 |
| 1578 | CG | PRO | 290 | 37.920 | 57.494 | 16.266 | 1.00 | 21.06 |
| 1579 | C | PRO | 290 | 40.138 | 58.521 | 14.026 | 1.00 | 28.40 |
| 1580 | O | PRO | 290 | 40.637 | 59.638 | 13.939 | 1.00 | 26.84 |
| 1581 | N | GLY | 291 | 40.904 | 57.441 | 14.034 | 1.00 | 24.70 |
| 1582 | H | GLY | 291 | 40.473 | 56.576 | 14.160 | 1.00 | 0.00 |
| 1583 | CA | GLY | 291 | 42.342 | 57.513 | 13.835 | 1.00 | 27.48 |
| 1584 | C | GLY | 291 | 43.153 | 57.845 | 15.056 | 1.00 | 26.97 |
| 1585 | O | GLY | 291 | 44.292 | 58.236 | 14.877 | 1.00 | 24.56 |
| 1586 | N | VAL | 292 | 42.646 | 57.715 | 16.287 | 1.00 | 24.36 |
| 1587 | H | VAL | 292 | 41.794 | 57.243 | 16.414 | 1.00 | 0.00 |
| 1588 | CA | VAL | 292 | 43.348 | 58.171 | 17.491 | 1.00 | 26.77 |
| 1589 | CB | VAL | 292 | 42.800 | 59.510 | 18.102 | 1.00 | 24.74 |
| 1590 | CG1 | VAL | 292 | 43.027 | 60.664 | 17.151 | 1.00 | 28.54 |
| 1591 | CG2 | VAL | 292 | 41.311 | 59.404 | 18.371 | 1.00 | 25.92 |
| 1592 | C | VAL | 292 | 43.273 | 57.168 | 18.641 | 1.00 | 26.43 |
| 1593 | O | VAL | 292 | 42.441 | 56.276 | 18.749 | 1.00 | 28.53 |
| 1594 | N | VAL | 293 | 44.199 | 57.326 | 19.569 | 1.00 | 27.36 |

FIG. 5DDD

| Atom | Atom Type | Residue | # | X | Y | Z | OCC | B |
|---|---|---|---|---|---|---|---|---|
| 1595 | H | VAL | 293 | 44.833 | 58.079 | 19.525 | 1.00 | 0.00 |
| 1596 | CA | VAL | 293 | 44.287 | 56.466 | 20.719 | 1.00 | 28.84 |
| 1597 | CB | VAL | 293 | 45.426 | 55.456 | 20.369 | 1.00 | 27.36 |
| 1598 | CG1 | VAL | 293 | 46.801 | 55.914 | 20.801 | 1.00 | 23.55 |
| 1599 | CG2 | VAL | 293 | 45.069 | 54.152 | 21.025 | 1.00 | 28.81 |
| 1600 | C | VAL | 293 | 44.564 | 57.485 | 21.845 | 1.00 | 30.19 |
| 1601 | O | VAL | 293 | 45.149 | 58.538 | 21.595 | 1.00 | 30.10 |
| 1602 | N | TRP | 294 | 44.153 | 57.245 | 23.098 | 1.00 | 27.38 |
| 1603 | H | TRP | 294 | 43.657 | 56.424 | 23.290 | 1.00 | 0.00 |
| 1604 | CA | TRP | 294 | 44.490 | 58.156 | 24.193 | 1.00 | 26.27 |
| 1605 | CB | TRP | 294 | 43.553 | 58.075 | 25.389 | 1.00 | 24.27 |
| 1606 | CG | TRP | 294 | 42.160 | 58.474 | 25.030 | 1.00 | 26.12 |
| 1607 | CD2 | TRP | 294 | 41.796 | 59.897 | 24.914 | 1.00 | 27.34 |
| 1608 | CE2 | TRP | 294 | 40.345 | 59.680 | 24.556 | 1.00 | 25.56 |
| 1609 | CE3 | TRP | 294 | 42.296 | 61.171 | 25.019 | 1.00 | 28.09 |
| 1610 | CD1 | TRP | 294 | 41.128 | 57.603 | 24.792 | 1.00 | 25.19 |
| 1611 | NE1 | TRP | 294 | 40.077 | 58.356 | 24.518 | 1.00 | 28.67 |
| 1612 | HE1 | TRP | 294 | 39.189 | 57.990 | 24.324 | 1.00 | 0.00 |
| 1613 | CZ2 | TRP | 294 | 39.526 | 60.761 | 24.347 | 1.00 | 21.74 |
| 1614 | CZ3 | TRP | 294 | 41.421 | 62.218 | 24.795 | 1.00 | 27.80 |
| 1615 | CH2 | TRP | 294 | 40.084 | 62.017 | 24.478 | 1.00 | 25.43 |
| 1616 | C | TRP | 294 | 45.823 | 57.790 | 24.766 | 1.00 | 27.42 |
| 1617 | O | TRP | 294 | 46.217 | 56.632 | 24.801 | 1.00 | 26.36 |
| 1618 | N | PHE | 295 | 46.574 | 58.751 | 25.251 | 1.00 | 32.18 |
| 1619 | H | PHE | 295 | 46.375 | 59.702 | 25.116 | 1.00 | 0.00 |
| 1620 | CA | PHE | 295 | 47.704 | 58.370 | 26.063 | 1.00 | 41.42 |
| 1621 | CB | PHE | 295 | 49.007 | 58.377 | 25.207 | 1.00 | 40.27 |
| 1622 | CG | PHE | 295 | 49.439 | 59.770 | 24.852 | 1.00 | 44.54 |
| 1623 | CD1 | PHE | 295 | 50.325 | 60.433 | 25.679 | 1.00 | 45.58 |

FIG. 5EEE

| Atom | Atom Type | Residue | # | X | Y | Z | OCC | B |
|---|---|---|---|---|---|---|---|---|
| 1624 | CD2 | PHE | 295 | 48.853 | 60.419 | 23.779 | 1.00 | 48.03 |
| 1625 | CE1 | PHE | 295 | 50.559 | 61.777 | 25.480 | 1.00 | 49.71 |
| 1626 | CE2 | PHE | 295 | 49.086 | 61.764 | 23.583 | 1.00 | 47.03 |
| 1627 | CZ | PHE | 295 | 49.928 | 62.441 | 24.444 | 1.00 | 52.74 |
| 1628 | C | PHE | 295 | 47.765 | 59.359 | 27.208 | 1.00 | 46.22 |
| 1629 | O | PHE | 295 | 47.343 | 60.503 | 27.145 | 1.00 | 42.87 |
| 1630 | N | LYS | 296 | 48.314 | 58.905 | 28.316 | 1.00 | 57.30 |
| 1631 | H | LYS | 296 | 48.708 | 58.012 | 28.341 | 1.00 | 0.00 |
| 1632 | CA | LYS | 296 | 48.421 | 59.737 | 29.496 | 1.00 | 64.18 |
| 1633 | CB | LYS | 296 | 48.497 | 58.862 | 30.739 | 1.00 | 65.20 |
| 1634 | CG | LYS | 296 | 48.184 | 59.668 | 31.988 | 1.00 | 68.41 |
| 1635 | CD | LYS | 296 | 47.966 | 58.760 | 33.189 | 1.00 | 72.60 |
| 1636 | CE | LYS | 296 | 49.201 | 57.947 | 33.534 | 1.00 | 75.23 |
| 1637 | NZ | LYS | 296 | 50.320 | 58.836 | 33.780 | 1.00 | 81.49 |
| 1638 | HZ | LYS | 296 | 50.088 | 59.472 | 34.569 | 1.00 | 0.00 |
| 1639 | HZ2 | LYS | 296 | 50.511 | 59.398 | 32.925 | 1.00 | 0.00 |
| 1640 | HZ3 | LYS | 296 | 51.159 | 58.270 | 34.015 | 1.00 | 0.00 |
| 1641 | C | LYS | 296 | 49.684 | 60.547 | 29.397 | 1.00 | 68.26 |
| 1642 | O | LYS | 296 | 50.729 | 59.951 | 29.161 | 1.00 | 72.09 |
| 1643 | N | ASP | 297 | 49.591 | 61.860 | 29.569 | 1.00 | 72.66 |
| 1644 | H | ASP | 297 | 49.170 | 62.489 | 28.934 | 1.00 | 0.00 |
| 1645 | CA | ASP | 297 | 50.160 | 62.460 | 30.750 | 1.00 | 82.26 |
| 1646 | CB | ASP | 297 | 51.698 | 62.430 | 30.748 | 1.00 | 88.06 |
| 1647 | CG | ASP | 297 | 52.196 | 61.867 | 32.082 | 1.00 | 92.95 |
| 1648 | OD1 | ASP | 297 | 51.766 | 62.345 | 33.140 | 1.00 | 94.73 |
| 1649 | OD2 | ASP | 297 | 53.019 | 60.945 | 32.067 | 1.00 | 96.27 |
| 1650 | C | ASP | 297 | 49.705 | 63.893 | 30.706 | 1.00 | 84.91 |
| 1651 | O | ASP | 297 | 49.463 | 64.419 | 29.608 | 1.00 | 87.39 |
| 1652 | OT | ASP | 297 | 49.571 | 64.477 | 31.777 | 1.00 | 84.32 |

FIG. 5FFF

| Atom | Atom Type | Residue | # | X | Y | Z | OCC | B |
|---|---|---|---|---|---|---|---|---|
| 1653 | CB | ALA | 317 | 65.517 | 45.642 | -31.211 | 1.00 | 60.98 |
| 1654 | C | ALA | 317 | 63.053 | 45.718 | -30.743 | 1.00 | 55.95 |
| 1655 | O | ALA | 317 | 62.644 | 46.858 | -30.593 | 1.00 | 55.33 |
| 1656 | HT1 | ALA | 317 | 63.898 | 47.390 | -32.203 | 1.00 | 0.00 |
| 1657 | HT2 | ALA | 317 | 62.879 | 46.419 | -33.062 | 1.00 | 0.00 |
| 1658 | N | ALA | 317 | 63.865 | 46.499 | -32.753 | 1.00 | 63.55 |
| 1659 | HT3 | ALA | 317 | 64.541 | 46.464 | -33.540 | 1.00 | 0.00 |
| 1660 | CA | ALA | 317 | 64.124 | 45.449 | -31.790 | 1.00 | 59.35 |
| 1661 | N | ILE | 318 | 62.584 | 44.702 | -30.035 | 1.00 | 52.67 |
| 1662 | H | ILE | 318 | 62.850 | 43.777 | -30.235 | 1.00 | 0.00 |
| 1663 | CA | ILE | 318 | 61.755 | 44.926 | -28.863 | 1.00 | 48.35 |
| 1664 | CB | ILE | 318 | 60.789 | 43.749 | -28.729 | 1.00 | 43.28 |
| 1665 | CG2 | ILE | 318 | 59.718 | 43.915 | -29.796 | 1.00 | 39.84 |
| 1666 | CG1 | ILE | 318 | 61.523 | 42.407 | -28.849 | 1.00 | 35.21 |
| 1667 | CD1 | ILE | 318 | 60.596 | 41.194 | -28.946 | 1.00 | 36.89 |
| 1668 | C | ILE | 318 | 62.702 | 45.020 | -27.656 | 1.00 | 48.70 |
| 1669 | O | ILE | 318 | 63.754 | 44.390 | -27.651 | 1.00 | 46.83 |
| 1670 | N | LYS | 319 | 62.351 | 45.808 | -26.630 | 1.00 | 47.06 |
| 1671 | H | LYS | 319 | 61.527 | 46.341 | -26.691 | 1.00 | 0.00 |
| 1672 | CA | LYS | 319 | 63.102 | 45.893 | -25.383 | 1.00 | 42.30 |
| 1673 | CB | LYS | 319 | 63.641 | 47.280 | -25.184 | 1.00 | 46.07 |
| 1674 | CG | LYS | 319 | 65.100 | 47.492 | -25.528 | 1.00 | 59.38 |
| 1675 | CD | LYS | 319 | 65.488 | 48.878 | -24.982 | 1.00 | 73.60 |
| 1676 | CE | LYS | 319 | 66.995 | 49.115 | -24.757 | 1.00 | 83.83 |
| 1677 | NZ | LYS | 319 | 67.263 | 50.131 | -23.739 | 1.00 | 85.82 |
| 1678 | HZ1 | LYS | 319 | 66.878 | 49.820 | -22.825 | 1.00 | 0.00 |
| 1679 | HZ2 | LYS | 319 | 66.840 | 51.037 | -24.022 | 1.00 | 0.00 |
| 1680 | HZ3 | LYS | 319 | 68.294 | 50.246 | -23.654 | 1.00 | 0.00 |
| 1681 | C | LYS | 319 | 62.157 | 45.597 | -24.229 | 1.00 | 36.54 |

FIG. 5GGG

| Atom | Atom Type | Residue | # | X | Y | Z | OCC | B |
|---|---|---|---|---|---|---|---|---|
| 1682 | O | LYS | 319 | 60.960 | 45.806 | -24.324 | 1.00 | 36.02 |
| 1683 | N | LYS | 320 | 62.635 | 45.096 | -23.105 | 1.00 | 34.11 |
| 1684 | H | LYS | 320 | 63.577 | 44.830 | -23.064 | 1.00 | 0.00 |
| 1685 | CA | LYS | 320 | 61.823 | 44.993 | -21.894 | 1.00 | 35.41 |
| 1686 | CB | LYS | 320 | 62.389 | 43.928 | -20.978 | 1.00 | 36.15 |
| 1687 | CG | LYS | 320 | 62.391 | 42.526 | -21.549 | 1.00 | 40.56 |
| 1688 | CD | LYS | 320 | 63.120 | 41.594 | -20.583 | 1.00 | 40.42 |
| 1689 | CE | LYS | 320 | 63.108 | 40.150 | -21.065 | 1.00 | 43.28 |
| 1690 | NZ | LYS | 320 | 64.002 | 39.368 | -20.235 | 1.00 | 52.04 |
| 1691 | HZ1 | LYS | 320 | 63.689 | 39.403 | -19.245 | 1.00 | 0.00 |
| 1692 | HZ2 | LYS | 320 | 64.966 | 39.751 | -20.319 | 1.00 | 0.00 |
| 1693 | HZ3 | LYS | 320 | 63.995 | 38.382 | -20.571 | 1.00 | 0.00 |
| 1694 | C | LYS | 320 | 61.701 | 46.280 | -21.053 | 1.00 | 33.67 |
| 1695 | O | LYS | 320 | 62.635 | 47.066 | -20.917 | 1.00 | 31.28 |
| 1696 | N | ALA | 321 | 60.521 | 46.503 | -20.461 | 1.00 | 28.86 |
| 1697 | H | ALA | 321 | 59.777 | 45.870 | -20.580 | 1.00 | 0.00 |
| 1698 | CA | ALA | 321 | 60.307 | 47.641 | -19.592 | 1.00 | 26.84 |
| 1699 | CB | ALA | 321 | 59.387 | 48.636 | -20.288 | 1.00 | 26.05 |
| 1700 | C | ALA | 321 | 59.653 | 47.109 | -18.320 | 1.00 | 25.85 |
| 1701 | O | ALA | 321 | 58.914 | 46.143 | -18.310 | 1.00 | 29.15 |
| 1702 | N | HIS | 322 | 59.889 | 47.690 | -17.150 | 1.00 | 25.43 |
| 1703 | H | HIS | 322 | 60.599 | 48.347 | -17.216 | 1.00 | 0.00 |
| 1704 | CA | HIS | 322 | 59.185 | 47.349 | -15.904 | 1.00 | 20.62 |
| 1705 | CB | HIS | 322 | 59.573 | 48.206 | -14.672 | 1.00 | 18.17 |
| 1706 | CG | HIS | 322 | 61.001 | 48.032 | -14.197 | 1.00 | 16.95 |
| 1707 | CD2 | HIS | 322 | 61.504 | 46.919 | -13.586 | 1.00 | 13.40 |
| 1708 | ND1 | HIS | 322 | 62.036 | 48.845 | -14.409 | 1.00 | 20.74 |
| 1709 | HD1 | HIS | 322 | 61.980 | 49.784 | -14.696 | 1.00 | 0.00 |
| 1710 | CE1 | HIS | 322 | 63.132 | 48.250 | -14.001 | 1.00 | 17.22 |

FIG. 5HHH

| Atom | Atom Type | Residue | # | X | Y | Z | OCC | B |
|---|---|---|---|---|---|---|---|---|
| 1711 | NE2 | HIS | 322 | 62.800 | 47.082 | -13.515 | 1.00 | 19.50 |
| 1712 | HE2 | HIS | 322 | 63.431 | 46.421 | -13.150 | 1.00 | 0.00 |
| 1713 | C | HIS | 322 | 57.741 | 47.676 | -16.169 | 1.00 | 23.43 |
| 1714 | O | HIS | 322 | 57.445 | 48.725 | -16.715 | 1.00 | 21.27 |
| 1715 | N | ILE | 323 | 56.837 | 46.786 | -15.797 | 1.00 | 27.07 |
| 1716 | H | ILE | 323 | 57.138 | 45.908 | -15.473 | 1.00 | 0.00 |
| 1717 | CA | ILE | 323 | 55.418 | 47.059 | -15.946 | 1.00 | 25.91 |
| 1718 | CB | ILE | 323 | 54.711 | 45.714 | -15.710 | 1.00 | 23.73 |
| 1719 | CG2 | ILE | 323 | 54.531 | 45.378 | -14.233 | 1.00 | 19.80 |
| 1720 | CG1 | ILE | 323 | 53.411 | 45.795 | -16.461 | 1.00 | 17.37 |
| 1721 | CD1 | ILE | 323 | 52.688 | 44.478 | -16.349 | 1.00 | 24.35 |
| 1722 | C | ILE | 323 | 54.891 | 48.183 | -15.046 | 1.00 | 27.83 |
| 1723 | O | ILE | 323 | 53.998 | 48.930 | -15.420 | 1.00 | 26.39 |
| 1724 | N | GLU | 324 | 55.418 | 48.357 | -13.843 | 1.00 | 27.46 |
| 1725 | H | GLU | 324 | 56.140 | 47.768 | -13.556 | 1.00 | 0.00 |
| 1726 | CA | GLU | 324 | 54.973 | 49.441 | -12.974 | 1.00 | 26.27 |
| 1727 | CB | GLU | 324 | 54.186 | 48.824 | -11.821 | 1.00 | 25.82 |
| 1728 | CG | GLU | 324 | 53.692 | 49.837 | -10.816 | 1.00 | 23.38 |
| 1729 | CD | GLU | 324 | 52.881 | 49.122 | -9.775 | 1.00 | 24.43 |
| 1730 | OE1 | GLU | 324 | 52.275 | 48.099 | -10.071 | 1.00 | 25.59 |
| 1731 | OE2 | GLU | 324 | 52.858 | 49.586 | -8.649 | 1.00 | 25.24 |
| 1732 | C | GLU | 324 | 56.191 | 50.205 | -12.459 | 1.00 | 29.36 |
| 1733 | O | GLU | 324 | 57.106 | 49.587 | -11.922 | 1.00 | 26.17 |
| 1734 | N | LYS | 325 | 56.245 | 51.531 | -12.604 | 1.00 | 26.30 |
| 1735 | H | LYS | 325 | 55.526 | 52.005 | -13.083 | 1.00 | 0.00 |
| 1736 | CA | LYS | 325 | 57.371 | 52.335 | -12.203 | 1.00 | 24.24 |
| 1737 | CB | LYS | 325 | 58.571 | 52.036 | -13.135 | 1.00 | 19.60 |
| 1738 | CG | LYS | 325 | 59.855 | 52.715 | -12.663 | 1.00 | 14.81 |
| 1739 | CD | LYS | 325 | 61.087 | 52.259 | -13.405 | 1.00 | 11.93 |

FIG. 5III

| Atom | Atom Type | Residue | # | X | Y | Z | OCC | B |
|---|---|---|---|---|---|---|---|---|
| 1740 | CE | LYS | 325 | 61.101 | 52.703 | -14.851 | 1.00 | 20.28 |
| 1741 | NZ | LYS | 325 | 61.146 | 54.143 | -14.983 | 1.00 | 21.10 |
| 1742 | HZ1 | LYS | 325 | 62.010 | 54.507 | -14.531 | 1.00 | 0.00 |
| 1743 | HZ2 | LYS | 325 | 60.311 | 54.557 | -14.522 | 1.00 | 0.00 |
| 1744 | HZ3 | LYS | 325 | 61.145 | 54.397 | -15.993 | 1.00 | 0.00 |
| 1745 | C | LYS | 325 | 56.861 | 53.774 | -12.340 | 1.00 | 26.70 |
| 1746 | O | LYS | 325 | 55.928 | 54.033 | -13.094 | 1.00 | 25.97 |
| 1747 | N | ASP | 326 | 57.480 | 54.700 | -11.589 | 1.00 | 26.25 |
| 1748 | H | ASP | 326 | 58.191 | 54.415 | -10.974 | 1.00 | 0.00 |
| 1749 | CA | ASP | 326 | 57.214 | 56.136 | -11.610 | 1.00 | 23.30 |
| 1750 | CB | ASP | 326 | 57.422 | 56.737 | -13.034 | 1.00 | 23.42 |
| 1751 | CG | ASP | 326 | 58.721 | 56.273 | -13.707 | 1.00 | 24.74 |
| 1752 | OD1 | ASP | 326 | 59.806 | 56.575 | -13.224 | 1.00 | 24.42 |
| 1753 | OD2 | ASP | 326 | 58.646 | 55.579 | -14.711 | 1.00 | 21.44 |
| 1754 | C | ASP | 326 | 55.835 | 56.529 | -11.122 | 1.00 | 20.53 |
| 1755 | O | ASP | 326 | 55.284 | 57.559 | -11.488 | 1.00 | 24.45 |
| 1756 | N | PHE | 327 | 55.222 | 55.721 | -10.264 | 1.00 | 19.21 |
| 1757 | H | PHE | 327 | 55.626 | 54.862 | -10.024 | 1.00 | 0.00 |
| 1758 | CA | PHE | 327 | 53.972 | 56.107 | -9.608 | 1.00 | 18.83 |
| 1759 | CB | PHE | 327 | 53.008 | 54.938 | -9.410 | 1.00 | 16.54 |
| 1760 | CG | PHE | 327 | 52.290 | 54.444 | -10.658 | 1.00 | 20.45 |
| 1761 | CD1 | PHE | 327 | 51.070 | 55.004 | -11.016 | 1.00 | 17.51 |
| 1762 | CD2 | PHE | 327 | 52.772 | 53.338 | -11.361 | 1.00 | 21.65 |
| 1763 | CE1 | PHE | 327 | 50.334 | 54.424 | -12.043 | 1.00 | 20.17 |
| 1764 | CE2 | PHE | 327 | 52.022 | 52.752 | -12.380 | 1.00 | 18.97 |
| 1765 | CZ | PHE | 327 | 50.801 | 53.298 | -12.718 | 1.00 | 20.53 |
| 1766 | C | PHE | 327 | 54.219 | 56.643 | -8.201 | 1.00 | 18.93 |
| 1767 | O | PHE | 327 | 55.237 | 56.323 | -7.588 | 1.00 | 17.66 |
| 1768 | N | ILE | 328 | 53.302 | 57.460 | -7.673 | 1.00 | 18.15 |

FIG. 5JJJ

| Atom | Atom Type | Residue | # | X | Y | Z | OCC | B |
|---|---|---|---|---|---|---|---|---|
| 1769 | H | ILE | 328 | 52.602 | 57.853 | -8.243 | 1.00 | 0.00 |
| 1770 | CA | ILE | 328 | 53.255 | 57.771 | -6.266 | 1.00 | 16.96 |
| 1771 | CB | ILE | 328 | 54.123 | 59.032 | -5.914 | 1.00 | 17.42 |
| 1772 | CG2 | ILE | 328 | 53.663 | 60.311 | -6.612 | 1.00 | 19.49 |
| 1773 | CG1 | ILE | 328 | 54.026 | 59.244 | -4.395 | 1.00 | 15.51 |
| 1774 | CD1 | ILE | 328 | 55.177 | 60.055 | -3.780 | 1.00 | 15.10 |
| 1775 | C | ILE | 328 | 51.802 | 58.030 | -5.976 | 1.00 | 18.38 |
| 1776 | O | ILE | 328 | 51.153 | 58.692 | -6.769 | 1.00 | 18.62 |
| 1777 | N | ALA | 329 | 51.225 | 57.543 | -4.873 | 1.00 | 20.05 |
| 1778 | H | ALA | 329 | 51.716 | 56.924 | -4.289 | 1.00 | 0.00 |
| 1779 | CA | ALA | 329 | 49.867 | 57.908 | -4.507 | 1.00 | 20.56 |
| 1780 | CB | ALA | 329 | 48.985 | 56.671 | -4.395 | 1.00 | 17.55 |
| 1781 | C | ALA | 329 | 49.854 | 58.614 | -3.168 | 1.00 | 24.14 |
| 1782 | O | ALA | 329 | 50.648 | 58.289 | -2.296 | 1.00 | 22.82 |
| 1783 | N | PHE | 330 | 48.969 | 59.584 | -2.967 | 1.00 | 22.84 |
| 1784 | H | PHE | 330 | 48.352 | 59.823 | -3.694 | 1.00 | 0.00 |
| 1785 | CA | PHE | 330 | 48.869 | 60.291 | -1.709 | 1.00 | 18.35 |
| 1786 | CB | PHE | 330 | 49.268 | 61.745 | -1.937 | 1.00 | 18.09 |
| 1787 | CG | PHE | 330 | 49.659 | 62.459 | -0.647 | 1.00 | 22.46 |
| 1788 | CD1 | PHE | 330 | 49.771 | 63.841 | -0.652 | 1.00 | 21.17 |
| 1789 | CD2 | PHE | 330 | 49.931 | 61.760 | 0.521 | 1.00 | 20.68 |
| 1790 | CE1 | PHE | 330 | 50.147 | 64.514 | 0.490 | 1.00 | 22.56 |
| 1791 | CE2 | PHE | 330 | 50.309 | 62.438 | 1.665 | 1.00 | 20.88 |
| 1792 | CZ | PHE | 330 | 50.409 | 63.815 | 1.653 | 1.00 | 23.44 |
| 1793 | C | PHE | 330 | 47.425 | 60.183 | -1.260 | 1.00 | 20.07 |
| 1794 | O | PHE | 330 | 46.536 | 60.673 | -1.956 | 1.00 | 16.75 |
| 1795 | N | CYS | 331 | 47.169 | 59.539 | -0.117 | 1.00 | 20.04 |
| 1796 | H | CYS | 331 | 47.914 | 59.170 | 0.402 | 1.00 | 0.00 |
| 1797 | CA | CYS | 331 | 45.831 | 59.362 | 0.402 | 1.00 | 17.86 |

FIG. 5KKK

| Atom | Atom Type | Residue | # | X | Y | Z | OCC | B |
|---|---|---|---|---|---|---|---|---|
| 1798 | CB | CYS | 331 | 45.584 | 57.950 | 0.841 | 1.00 | 16.56 |
| 1799 | SG | CYS | 331 | 45.613 | 56.747 | -0.490 | 1.00 | 23.49 |
| 1800 | C | CYS | 331 | 45.649 | 60.235 | 1.609 | 1.00 | 21.19 |
| 1801 | O | CYS | 331 | 46.586 | 60.508 | 2.342 | 1.00 | 20.65 |
| 1802 | N | SER | 332 | 44.421 | 60.692 | 1.836 | 1.00 | 22.22 |
| 1803 | H | SER | 332 | 43.659 | 60.414 | 1.268 | 1.00 | 0.00 |
| 1804 | CA | SER | 332 | 44.084 | 61.598 | 2.928 | 1.00 | 21.44 |
| 1805 | CB | SER | 332 | 42.690 | 62.162 | 2.616 | 1.00 | 19.68 |
| 1806 | OG | SER | 332 | 41.835 | 61.127 | 2.164 | 1.00 | 24.42 |
| 1807 | HG | SER | 332 | 40.977 | 61.499 | 2.030 | 1.00 | 0.00 |
| 1808 | C | SER | 332 | 44.120 | 61.144 | 4.389 | 1.00 | 21.99 |
| 1809 | O | SER | 332 | 44.290 | 61.947 | 5.302 | 1.00 | 20.58 |
| 1810 | N | SER | 333 | 43.945 | 59.844 | 4.657 | 1.00 | 23.27 |
| 1811 | H | SER | 333 | 43.779 | 59.215 | 3.918 | 1.00 | 0.00 |
| 1812 | CA | SER | 333 | 43.971 | 59.274 | 5.984 | 1.00 | 20.50 |
| 1813 | CB | SER | 333 | 42.580 | 58.895 | 6.523 | 1.00 | 21.15 |
| 1814 | OG | SER | 333 | 41.566 | 58.641 | 5.556 | 1.00 | 23.77 |
| 1815 | HG | SER | 333 | 40.748 | 58.468 | 6.021 | 1.00 | 0.00 |
| 1816 | C | SER | 333 | 44.745 | 57.979 | 5.819 | 1.00 | 23.49 |
| 1817 | O | SER | 333 | 45.104 | 57.510 | 4.736 | 1.00 | 19.23 |
| 1818 | N | THR | 334 | 45.003 | 57.359 | 6.951 | 1.00 | 23.40 |
| 1819 | H | THR | 334 | 44.646 | 57.711 | 7.788 | 1.00 | 0.00 |
| 1820 | CA | THR | 334 | 45.720 | 56.099 | 6.997 | 1.00 | 24.09 |
| 1821 | CB | THR | 334 | 46.501 | 56.407 | 8.296 | 1.00 | 28.30 |
| 1822 | OG1 | THR | 334 | 47.797 | 55.855 | 8.169 | 1.00 | 34.11 |
| 1823 | HG1 | THR | 334 | 48.191 | 56.183 | 7.351 | 1.00 | 0.00 |
| 1824 | CG2 | THR | 334 | 45.753 | 55.956 | 9.519 | 1.00 | 14.09 |
| 1825 | C | THR | 334 | 44.639 | 54.990 | 6.904 | 1.00 | 22.20 |
| 1826 | O | THR | 334 | 43.459 | 55.273 | 7.098 | 1.00 | 23.69 |

FIG. 5LLL

| Atom | Atom Type | Residue | # | X | Y | Z | OCC | B |
|---|---|---|---|---|---|---|---|---|
| 1827 | N | PRO | 335 | 44.853 | 53.756 | 6.619 | 1.00 | 20.97 |
| 1828 | CD | PRO | 335 | 46.175 | 53.207 | 6.414 | 1.00 | 15.82 |
| 1829 | CA | PRO | 335 | 43.804 | 52.736 | 6.469 | 1.00 | 19.65 |
| 1830 | CB | PRO | 335 | 44.565 | 51.473 | 6.155 | 1.00 | 20.20 |
| 1831 | CG | PRO | 335 | 45.823 | 52.030 | 5.529 | 1.00 | 20.66 |
| 1832 | C | PRO | 335 | 42.850 | 52.545 | 7.636 | 1.00 | 25.53 |
| 1833 | O | PRO | 335 | 43.309 | 52.608 | 8.769 | 1.00 | 29.15 |
| 1834 | N | ASP | 336 | 41.545 | 52.314 | 7.406 | 1.00 | 24.20 |
| 1835 | H | ASP | 336 | 41.220 | 52.278 | 6.479 | 1.00 | 0.00 |
| 1836 | CA | ASP | 336 | 40.529 | 52.137 | 8.449 | 1.00 | 28.39 |
| 1837 | CB | ASP | 336 | 40.940 | 51.344 | 9.710 | 1.00 | 32.12 |
| 1838 | CG | ASP | 336 | 41.344 | 49.933 | 9.397 | 1.00 | 43.11 |
| 1839 | OD1 | ASP | 336 | 42.285 | 49.465 | 10.040 | 1.00 | 52.99 |
| 1840 | OD2 | ASP | 336 | 40.725 | 49.302 | 8.531 | 1.00 | 51.49 |
| 1841 | C | ASP | 336 | 40.046 | 53.423 | 9.046 | 1.00 | 29.38 |
| 1842 | O | ASP | 336 | 39.121 | 53.427 | 9.849 | 1.00 | 34.19 |
| 1843 | N | ASN | 337 | 40.623 | 54.569 | 8.686 | 1.00 | 25.69 |
| 1844 | H | ASN | 337 | 41.271 | 54.602 | 7.951 | 1.00 | 0.00 |
| 1845 | CA | ASN | 337 | 40.284 | 55.789 | 9.372 | 1.00 | 23.68 |
| 1846 | CB | ASN | 337 | 41.565 | 56.352 | 9.973 | 1.00 | 22.73 |
| 1847 | CG | ASN | 337 | 42.065 | 55.421 | 11.068 | 1.00 | 22.82 |
| 1848 | OD1 | ASN | 337 | 41.379 | 54.991 | 11.987 | 1.00 | 25.91 |
| 1849 | ND2 | ASN | 337 | 43.293 | 54.940 | 10.989 | 1.00 | 18.06 |
| 1850 | HD21 | ASN | 337 | 43.822 | 55.204 | 10.218 | 1.00 | 0.00 |
| 1851 | HD22 | ASN | 337 | 43.604 | 54.320 | 11.691 | 1.00 | 0.00 |
| 1852 | C | ASN | 337 | 39.600 | 56.812 | 8.496 | 1.00 | 25.85 |
| 1853 | O | ASN | 337 | 39.737 | 56.860 | 7.283 | 1.00 | 29.96 |
| 1854 | N | VAL | 338 | 38.815 | 57.691 | 9.095 | 1.00 | 27.31 |
| 1855 | H | VAL | 338 | 38.760 | 57.662 | 10.072 | 1.00 | 0.00 |

FIG. 5MMM

| Atom | Atom Type | Residue | # | X | Y | Z | OCC | B |
|---|---|---|---|---|---|---|---|---|
| 1856 | CA | VAL | 338 | 38.117 | 58.722 | 8.361 | 1.00 | 24.45 |
| 1857 | CB | VAL | 338 | 36.902 | 59.297 | 9.168 | 1.00 | 24.69 |
| 1858 | CG1 | VAL | 338 | 35.901 | 58.187 | 9.486 | 1.00 | 25.15 |
| 1859 | CG2 | VAL | 338 | 37.369 | 59.946 | 10.467 | 1.00 | 25.43 |
| 1860 | C | VAL | 338 | 39.045 | 59.870 | 8.024 | 1.00 | 25.97 |
| 1861 | O | VAL | 338 | 40.124 | 60.040 | 8.588 | 1.00 | 26.18 |
| 1862 | N | SER | 339 | 38.588 | 60.680 | 7.067 | 1.00 | 27.49 |
| 1863 | H | SER | 339 | 37.756 | 60.450 | 6.596 | 1.00 | 0.00 |
| 1864 | CA | SER | 339 | 39.231 | 61.948 | 6.743 | 1.00 | 32.77 |
| 1865 | CB | SER | 339 | 39.666 | 62.030 | 5.285 | 1.00 | 30.77 |
| 1866 | OG | SER | 339 | 39.874 | 60.771 | 4.672 | 1.00 | 38.35 |
| 1867 | HG | SER | 339 | 39.097 | 60.209 | 4.677 | 1.00 | 0.00 |
| 1868 | C | SER | 339 | 38.181 | 63.015 | 6.948 | 1.00 | 32.35 |
| 1869 | O | SER | 339 | 37.008 | 62.669 | 6.924 | 1.00 | 29.99 |
| 1870 | N | TRP | 340 | 38.549 | 64.280 | 7.130 | 1.00 | 31.11 |
| 1871 | H | TRP | 340 | 39.494 | 64.546 | 7.074 | 1.00 | 0.00 |
| 1872 | CA | TRP | 340 | 37.580 | 65.306 | 7.447 | 1.00 | 32.42 |
| 1873 | CB | TRP | 340 | 38.110 | 66.071 | 8.665 | 1.00 | 28.07 |
| 1874 | CG | TRP | 340 | 38.069 | 65.153 | 9.851 | 1.00 | 31.22 |
| 1875 | CD2 | TRP | 340 | 36.790 | 64.901 | 10.522 | 1.00 | 33.69 |
| 1876 | CE2 | TRP | 340 | 37.281 | 63.820 | 11.450 | 1.00 | 38.45 |
| 1877 | CE3 | TRP | 340 | 35.473 | 65.302 | 10.526 | 1.00 | 37.14 |
| 1878 | CD1 | TRP | 340 | 39.112 | 64.394 | 10.320 | 1.00 | 32.03 |
| 1879 | NE1 | TRP | 340 | 38.611 | 63.616 | 11.256 | 1.00 | 35.26 |
| 1880 | HE1 | TRP | 340 | 39.143 | 62.912 | 11.687 | 1.00 | 0.00 |
| 1881 | CZ2 | TRP | 340 | 36.364 | 63.217 | 12.277 | 1.00 | 43.31 |
| 1882 | CZ3 | TRP | 340 | 34.612 | 64.660 | 11.389 | 1.00 | 42.02 |
| 1883 | CH2 | TRP | 340 | 35.043 | 63.639 | 12.227 | 1.00 | 45.40 |
| 1884 | C | TRP | 340 | 37.260 | 66.265 | 6.311 | 1.00 | 35.22 |

FIG. 5NNN

| Atom | Atom Type | Residue | # | X | Y | Z | OCC | B |
|---|---|---|---|---|---|---|---|---|
| 1885 | O | TRP | 340 | 38.137 | 66.652 | 5.544 | 1.00 | 36.37 |
| 1886 | N | ARG | 341 | 35.989 | 66.670 | 6.210 | 1.00 | 37.03 |
| 1887 | H | ARG | 341 | 35.321 | 66.289 | 6.821 | 1.00 | 0.00 |
| 1888 | CA | ARG | 341 | 35.487 | 67.607 | 5.211 | 1.00 | 36.96 |
| 1889 | CB | ARG | 341 | 34.687 | 66.815 | 4.170 | 1.00 | 34.84 |
| 1890 | CG | ARG | 341 | 34.391 | 67.533 | 2.861 | 1.00 | 37.33 |
| 1891 | CD | ARG | 341 | 33.517 | 66.655 | 1.972 | 1.00 | 39.02 |
| 1892 | NE | ARG | 341 | 32.151 | 66.768 | 2.441 | 1.00 | 48.98 |
| 1893 | HE | ARG | 341 | 31.684 | 67.621 | 2.324 | 1.00 | 0.00 |
| 1894 | CZ | ARG | 341 | 31.501 | 65.767 | 3.031 | 1.00 | 51.01 |
| 1895 | NH1 | ARG | 341 | 32.089 | 64.556 | 3.232 | 1.00 | 56.13 |
| 1896 | HH11 | ARG | 341 | 33.030 | 64.400 | 2.934 | 1.00 | 0.00 |
| 1897 | HH12 | ARG | 341 | 31.577 | 63.821 | 3.676 | 1.00 | 0.00 |
| 1898 | NH2 | ARG | 341 | 30.219 | 65.962 | 3.440 | 1.00 | 58.28 |
| 1899 | HH21 | ARG | 341 | 29.777 | 66.848 | 3.294 | 1.00 | 0.00 |
| 1900 | HH22 | ARG | 341 | 29.720 | 65.218 | 3.884 | 1.00 | 0.00 |
| 1901 | C | ARG | 341 | 34.616 | 68.684 | 5.864 | 1.00 | 37.23 |
| 1902 | O | ARG | 341 | 33.969 | 68.486 | 6.883 | 1.00 | 38.61 |
| 1903 | N | HIS | 342 | 34.550 | 69.880 | 5.324 | 1.00 | 39.36 |
| 1904 | H | HIS | 342 | 35.002 | 70.055 | 4.471 | 1.00 | 0.00 |
| 1905 | CA | HIS | 342 | 33.820 | 70.966 | 5.934 | 1.00 | 43.08 |
| 1906 | CB | HIS | 342 | 34.885 | 71.921 | 6.463 | 1.00 | 41.90 |
| 1907 | CG | HIS | 342 | 34.284 | 73.095 | 7.199 | 1.00 | 45.95 |
| 1908 | CD2 | HIS | 342 | 33.508 | 74.035 | 6.600 | 1.00 | 46.70 |
| 1909 | ND1 | HIS | 342 | 34.247 | 73.368 | 8.511 | 1.00 | 48.38 |
| 1910 | HD1 | HIS | 342 | 34.661 | 72.884 | 9.248 | 1.00 | 0.00 |
| 1911 | CE1 | HIS | 342 | 33.458 | 74.387 | 8.703 | 1.00 | 48.44 |
| 1912 | NE2 | HIS | 342 | 33.020 | 74.776 | 7.542 | 1.00 | 49.68 |
| 1913 | HE2 | HIS | 342 | 32.497 | 75.591 | 7.407 | 1.00 | 0.00 |

FIG. 5000

| Atom | Atom Type | Residue | # | X | Y | Z | OCC | B |
|---|---|---|---|---|---|---|---|---|
| 1914 | C | HIS | 342 | 32.894 | 71.612 | 4.899 | 1.00 | 46.18 |
| 1915 | O | HIS | 342 | 33.367 | 71.960 | 3.826 | 1.00 | 43.57 |
| 1916 | N | PRO | 343 | 31.637 | 71.844 | 5.101 | 1.00 | 48.28 |
| 1917 | CD | PRO | 343 | 30.984 | 71.752 | 6.398 | 1.00 | 46.23 |
| 1918 | CA | PRO | 343 | 30.678 | 72.297 | 4.073 | 1.00 | 49.91 |
| 1919 | CB | PRO | 343 | 29.387 | 72.590 | 4.824 | 1.00 | 44.40 |
| 1920 | CG | PRO | 343 | 29.512 | 71.689 | 6.015 | 1.00 | 41.79 |
| 1921 | C | PRO | 343 | 31.068 | 73.489 | 3.199 | 1.00 | 53.27 |
| 1922 | O | PRO | 343 | 30.905 | 73.585 | 1.988 | 1.00 | 55.64 |
| 1923 | N | THR | 344 | 31.615 | 74.459 | 3.909 | 1.00 | 54.13 |
| 1924 | H | THR | 344 | 31.830 | 74.264 | 4.837 | 1.00 | 0.00 |
| 1925 | CA | THR | 344 | 31.911 | 75.771 | 3.354 | 1.00 | 53.54 |
| 1926 | CB | THR | 344 | 31.577 | 76.802 | 4.429 | 1.00 | 56.09 |
| 1927 | OG1 | THR | 344 | 31.901 | 76.175 | 5.672 | 1.00 | 63.15 |
| 1928 | HG1 | THR | 344 | 31.164 | 75.566 | 5.752 | 1.00 | 0.00 |
| 1929 | CG2 | THR | 344 | 30.088 | 77.164 | 4.490 | 1.00 | 57.44 |
| 1930 | C | THR | 344 | 33.367 | 75.826 | 2.944 | 1.00 | 53.06 |
| 1931 | O | THR | 344 | 33.802 | 76.516 | 2.046 | 1.00 | 53.90 |
| 1932 | N | MET | 345 | 34.192 | 75.055 | 3.632 | 1.00 | 51.25 |
| 1933 | H | MET | 345 | 33.844 | 74.348 | 4.202 | 1.00 | 0.00 |
| 1934 | CA | MET | 345 | 35.604 | 75.172 | 3.363 | 1.00 | 52.69 |
| 1935 | CB | MET | 345 | 36.357 | 75.229 | 4.662 | 1.00 | 60.31 |
| 1936 | CG | MET | 345 | 36.128 | 76.474 | 5.498 | 1.00 | 71.30 |
| 1937 | SD | MET | 345 | 36.752 | 76.178 | 7.176 | 1.00 | 86.57 |
| 1938 | CE | MET | 345 | 38.405 | 76.807 | 7.073 | 1.00 | 81.62 |
| 1939 | C | MET | 345 | 36.133 | 74.006 | 2.553 | 1.00 | 47.27 |
| 1940 | O | MET | 345 | 37.288 | 74.042 | 2.179 | 1.00 | 48.63 |
| 1941 | N | GLY | 346 | 35.383 | 72.947 | 2.236 | 1.00 | 40.77 |
| 1942 | H | GLY | 346 | 34.439 | 72.892 | 2.503 | 1.00 | 0.00 |

FIG. 5PPP

| Atom | Atom Type | Residue | # | X | Y | Z | OCC | B |
|---|---|---|---|---|---|---|---|---|
| 1943 | CA | GLY | 346 | 35.981 | 71.822 | 1.544 | 1.00 | 36.57 |
| 1944 | C | GLY | 346 | 36.764 | 70.915 | 2.495 | 1.00 | 35.51 |
| 1945 | O | GLY | 346 | 36.680 | 70.988 | 3.718 | 1.00 | 40.26 |
| 1946 | N | SER | 347 | 37.567 | 70.012 | 1.949 | 1.00 | 32.41 |
| 1947 | H | SER | 347 | 37.693 | 70.023 | 0.980 | 1.00 | 0.00 |
| 1948 | CA | SER | 347 | 38.274 | 68.999 | 2.698 | 1.00 | 28.45 |
| 1949 | CB | SER | 347 | 38.454 | 67.768 | 1.820 | 1.00 | 24.81 |
| 1950 | OG | SER | 347 | 37.262 | 67.491 | 1.098 | 1.00 | 30.64 |
| 1951 | HG | SER | 347 | 36.547 | 67.238 | 1.697 | 1.00 | 0.00 |
| 1952 | C | SER | 347 | 39.631 | 69.491 | 3.157 | 1.00 | 31.86 |
| 1953 | O | SER | 347 | 40.397 | 70.136 | 2.438 | 1.00 | 33.18 |
| 1954 | N | VAL | 348 | 39.920 | 69.144 | 4.411 | 1.00 | 29.14 |
| 1955 | H | VAL | 348 | 39.306 | 68.543 | 4.887 | 1.00 | 0.00 |
| 1956 | CA | VAL | 348 | 41.127 | 69.588 | 5.086 | 1.00 | 25.67 |
| 1957 | CB | VAL | 348 | 41.215 | 68.976 | 6.494 | 1.00 | 27.65 |
| 1958 | CG1 | VAL | 348 | 42.237 | 69.746 | 7.309 | 1.00 | 29.29 |
| 1959 | CG2 | VAL | 348 | 39.895 | 69.060 | 7.219 | 1.00 | 29.60 |
| 1960 | C | VAL | 348 | 42.345 | 69.177 | 4.305 | 1.00 | 25.79 |
| 1961 | O | VAL | 348 | 43.247 | 69.968 | 4.071 | 1.00 | 31.26 |
| 1962 | N | PHE | 349 | 42.425 | 67.917 | 3.862 | 1.00 | 23.67 |
| 1963 | H | PHE | 349 | 41.695 | 67.278 | 4.013 | 1.00 | 0.00 |
| 1964 | CA | PHE | 349 | 43.621 | 67.455 | 3.181 | 1.00 | 22.69 |
| 1965 | CB | PHE | 349 | 43.443 | 65.960 | 2.908 | 1.00 | 18.76 |
| 1966 | CG | PHE | 349 | 44.459 | 65.361 | 1.941 | 1.00 | 20.55 |
| 1967 | CD1 | PHE | 349 | 44.029 | 64.916 | 0.702 | 1.00 | 14.77 |
| 1968 | CD2 | PHE | 349 | 45.790 | 65.223 | 2.311 | 1.00 | 15.53 |
| 1969 | CE1 | PHE | 349 | 44.918 | 64.278 | -0.127 | 1.00 | 16.44 |
| 1970 | CE2 | PHE | 349 | 46.677 | 64.590 | 1.459 | 1.00 | 13.87 |
| 1971 | CZ | PHE | 349 | 46.232 | 64.101 | 0.252 | 1.00 | 12.07 |

FIG. 5QQQ

| Atom | Atom Type | Residue | # | X | Y | Z | OCC | B |
|---|---|---|---|---|---|---|---|---|
| 1972 | C | PHE | 349 | 43.848 | 68.243 | 1.898 | 1.00 | 23.64 |
| 1973 | O | PHE | 349 | 44.966 | 68.632 | 1.609 | 1.00 | 23.92 |
| 1974 | N | ILE | 350 | 42.799 | 68.499 | 1.097 | 1.00 | 23.51 |
| 1975 | H | ILE | 350 | 41.912 | 68.220 | 1.396 | 1.00 | 0.00 |
| 1976 | CA | ILE | 350 | 42.969 | 69.170 | -0.185 | 1.00 | 23.11 |
| 1977 | CB | ILE | 350 | 41.617 | 69.131 | -0.939 | 1.00 | 23.98 |
| 1978 | CG2 | ILE | 350 | 41.741 | 69.922 | -2.229 | 1.00 | 24.02 |
| 1979 | CG1 | ILE | 350 | 41.200 | 67.689 | -1.267 | 1.00 | 20.37 |
| 1980 | CD1 | ILE | 350 | 42.089 | 66.972 | -2.272 | 1.00 | 14.33 |
| 1981 | C | ILE | 350 | 43.451 | 70.600 | 0.073 | 1.00 | 23.87 |
| 1982 | O | ILE | 350 | 44.428 | 71.058 | -0.510 | 1.00 | 25.61 |
| 1983 | N | GLY | 351 | 42.813 | 71.359 | 0.962 | 1.00 | 21.19 |
| 1984 | H | GLY | 351 | 42.057 | 70.988 | 1.467 | 1.00 | 0.00 |
| 1985 | CA | GLY | 351 | 43.248 | 72.720 | 1.212 | 1.00 | 19.54 |
| 1986 | C | GLY | 351 | 44.702 | 72.800 | 1.640 | 1.00 | 26.25 |
| 1987 | O | GLY | 351 | 45.524 | 73.568 | 1.138 | 1.00 | 28.41 |
| 1988 | N | ARG | 352 | 45.064 | 71.963 | 2.614 | 1.00 | 28.53 |
| 1989 | H | ARG | 352 | 44.388 | 71.391 | 3.045 | 1.00 | 0.00 |
| 1990 | CA | ARG | 352 | 46.449 | 71.872 | 3.042 | 1.00 | 26.92 |
| 1991 | CB | ARG | 352 | 46.589 | 70.842 | 4.167 | 1.00 | 31.79 |
| 1992 | CG | ARG | 352 | 47.697 | 71.286 | 5.104 | 1.00 | 35.13 |
| 1993 | CD | ARG | 352 | 47.091 | 71.997 | 6.310 | 1.00 | 38.95 |
| 1994 | NE | ARG | 352 | 47.179 | 71.107 | 7.452 | 1.00 | 44.61 |
| 1995 | HE | ARG | 352 | 47.920 | 70.468 | 7.491 | 1.00 | 0.00 |
| 1996 | CZ | ARG | 352 | 46.307 | 71.116 | 8.449 | 1.00 | 41.51 |
| 1997 | NH1 | ARG | 352 | 46.502 | 70.272 | 9.494 | 1.00 | 48.56 |
| 1998 | HH11 | ARG | 352 | 47.294 | 69.660 | 9.507 | 1.00 | 0.00 |
| 1999 | HH12 | ARG | 352 | 45.849 | 70.267 | 10.251 | 1.00 | 0.00 |
| 2000 | NH2 | ARG | 352 | 45.227 | 71.943 | 8.435 | 1.00 | 44.65 |

FIG. 5RRR

| Atom | Atom Type | Residue | # | X | Y | Z | OCC | B |
|---|---|---|---|---|---|---|---|---|
| 2001 | HH21 | ARG | 352 | 45.080 | 72.554 | 7.657 | 1.00 | 0.00 |
| 2002 | HH22 | ARG | 352 | 44.570 | 71.936 | 9.187 | 1.00 | 0.00 |
| 2003 | C | ARG | 352 | 47.419 | 71.483 | 1.931 | 1.00 | 26.87 |
| 2004 | O | ARG | 352 | 48.535 | 71.995 | 1.866 | 1.00 | 26.27 |
| 2005 | N | LEU | 353 | 47.033 | 70.567 | 1.037 | 1.00 | 25.01 |
| 2006 | H | LEU | 353 | 46.156 | 70.135 | 1.143 | 1.00 | 0.00 |
| 2007 | CA | LEU | 353 | 47.866 | 70.154 | -0.070 | 1.00 | 23.26 |
| 2008 | CB | LEU | 353 | 47.222 | 68.947 | -0.778 | 1.00 | 25.55 |
| 2009 | CG | LEU | 353 | 47.975 | 68.452 | -2.020 | 1.00 | 23.59 |
| 2010 | CD1 | LEU | 353 | 49.420 | 68.121 | -1.696 | 1.00 | 25.86 |
| 2011 | CD2 | LEU | 353 | 47.258 | 67.230 | -2.552 | 1.00 | 29.54 |
| 2012 | C | LEU | 353 | 48.034 | 71.303 | -1.031 | 1.00 | 27.31 |
| 2013 | O | LEU | 353 | 49.142 | 71.600 | -1.485 | 1.00 | 24.83 |
| 2014 | N | ILE | 354 | 46.923 | 71.977 | -1.350 | 1.00 | 22.68 |
| 2015 | H | ILE | 354 | 46.049 | 71.660 | -1.035 | 1.00 | 0.00 |
| 2016 | CA | ILE | 354 | 47.019 | 73.174 | -2.168 | 1.00 | 24.25 |
| 2017 | CB | ILE | 354 | 45.595 | 73.782 | -2.327 | 1.00 | 21.11 |
| 2018 | CG2 | ILE | 354 | 45.652 | 75.176 | -2.940 | 1.00 | 21.96 |
| 2019 | CG1 | ILE | 354 | 44.769 | 72.893 | -3.248 | 1.00 | 17.07 |
| 2020 | CD1 | ILE | 354 | 43.279 | 73.267 | -3.187 | 1.00 | 18.04 |
| 2021 | C | ILE | 354 | 48.000 | 74.172 | -1.540 | 1.00 | 25.12 |
| 2022 | O | ILE | 354 | 48.967 | 74.616 | -2.165 | 1.00 | 27.26 |
| 2023 | N | GLU | 355 | 47.806 | 74.559 | -0.276 | 1.00 | 27.20 |
| 2024 | H | GLU | 355 | 47.040 | 74.212 | 0.235 | 1.00 | 0.00 |
| 2025 | CA | GLU | 355 | 48.719 | 75.507 | 0.341 | 1.00 | 25.06 |
| 2026 | CB | GLU | 355 | 48.501 | 75.685 | 1.803 | 1.00 | 32.73 |
| 2027 | CG | GLU | 355 | 47.165 | 76.212 | 2.282 | 1.00 | 45.70 |
| 2028 | CD | GLU | 355 | 47.053 | 75.777 | 3.746 | 1.00 | 58.26 |
| 2029 | OE1 | GLU | 355 | 45.921 | 75.683 | 4.245 | 1.00 | 61.90 |

FIG. 5SSS

| Atom | Atom Type | Residue | # | X | Y | Z | OCC | B |
|---|---|---|---|---|---|---|---|---|
| 2030 | OE2 | GLU | 355 | 48.092 | 75.513 | 4.385 | 1.00 | 61.89 |
| 2031 | C | GLU | 355 | 50.150 | 75.114 | 0.242 | 1.00 | 23.42 |
| 2032 | O | GLU | 355 | 51.029 | 75.893 | -0.054 | 1.00 | 25.26 |
| 2033 | N | HIS | 356 | 50.461 | 73.862 | 0.489 | 1.00 | 26.55 |
| 2034 | H | HIS | 356 | 49.739 | 73.225 | 0.663 | 1.00 | 0.00 |
| 2035 | CA | HIS | 356 | 51.855 | 73.438 | 0.432 | 1.00 | 26.58 |
| 2036 | CB | HIS | 356 | 51.997 | 72.019 | 1.041 | 1.00 | 27.11 |
| 2037 | CG | HIS | 356 | 51.846 | 72.065 | 2.551 | 1.00 | 23.74 |
| 2038 | CD2 | HIS | 356 | 52.890 | 72.264 | 3.421 | 1.00 | 22.80 |
| 2039 | ND1 | HIS | 356 | 50.728 | 72.044 | 3.288 | 1.00 | 25.98 |
| 2040 | HD1 | HIS | 356 | 49.819 | 71.907 | 2.953 | 1.00 | 0.00 |
| 2041 | CE1 | HIS | 356 | 51.036 | 72.231 | 4.550 | 1.00 | 19.00 |
| 2042 | NE2 | HIS | 356 | 52.333 | 72.360 | 4.608 | 1.00 | 22.63 |
| 2043 | HE2 | HIS | 356 | 52.814 | 72.450 | 5.460 | 1.00 | 0.00 |
| 2044 | C | HIS | 356 | 52.411 | 73.447 | -0.983 | 1.00 | 26.45 |
| 2045 | O | HIS | 356 | 53.560 | 73.809 | -1.239 | 1.00 | 20.78 |
| 2046 | N | MET | 357 | 51.586 | 73.039 | -1.948 | 1.00 | 17.38 |
| 2047 | H | MET | 357 | 50.672 | 72.732 | -1.747 | 1.00 | 0.00 |
| 2048 | CA | MET | 357 | 52.037 | 73.060 | -3.316 | 1.00 | 28.28 |
| 2049 | CB | MET | 357 | 50.995 | 72.413 | -4.239 | 1.00 | 30.75 |
| 2050 | CG | MET | 357 | 50.860 | 70.870 | -4.254 | 1.00 | 34.53 |
| 2051 | SD | MET | 357 | 52.182 | 69.919 | -5.054 | 1.00 | 43.28 |
| 2052 | CE | MET | 357 | 51.449 | 69.433 | -6.584 | 1.00 | 37.66 |
| 2053 | C | MET | 357 | 52.249 | 74.503 | -3.704 | 1.00 | 29.20 |
| 2054 | O | MET | 357 | 53.237 | 74.846 | -4.338 | 1.00 | 31.64 |
| 2055 | N | GLN | 358 | 51.365 | 75.428 | -3.360 | 1.00 | 25.95 |
| 2056 | H | GLN | 358 | 50.539 | 75.168 | -2.897 | 1.00 | 0.00 |
| 2057 | CA | GLN | 358 | 51.650 | 76.808 | -3.709 | 1.00 | 27.58 |
| 2058 | CB | GLN | 358 | 50.505 | 77.693 | -3.214 | 1.00 | 24.97 |

FIG. 5TTT

| Atom | Atom Type | Residue | # | X | Y | Z | OCC | B |
|---|---|---|---|---|---|---|---|---|
| 2059 | CG | GLN | 358 | 49.262 | 77.438 | -4.067 | 1.00 | 26.18 |
| 2060 | CD | GLN | 358 | 48.063 | 78.234 | -3.596 | 1.00 | 28.54 |
| 2061 | OE1 | GLN | 358 | 47.170 | 78.570 | -4.362 | 1.00 | 30.13 |
| 2062 | NE2 | GLN | 358 | 47.919 | 78.558 | -2.329 | 1.00 | 31.54 |
| 2063 | HE21 | GLN | 358 | 48.611 | 78.285 | -1.693 | 1.00 | 0.00 |
| 2064 | HE22 | GLN | 358 | 47.124 | 79.077 | -2.095 | 1.00 | 0.00 |
| 2065 | C | GLN | 358 | 52.982 | 77.344 | -3.182 | 1.00 | 30.98 |
| 2066 | O | GLN | 358 | 53.783 | 77.971 | -3.869 | 1.00 | 31.45 |
| 2067 | N | GLU | 359 | 53.234 | 77.083 | -1.906 | 1.00 | 32.65 |
| 2068 | H | GLU | 359 | 52.581 | 76.563 | -1.386 | 1.00 | 0.00 |
| 2069 | CA | GLU | 359 | 54.425 | 77.558 | -1.243 | 1.00 | 32.96 |
| 2070 | CB | GLU | 359 | 54.178 | 77.382 | 0.251 | 1.00 | 37.33 |
| 2071 | CG | GLU | 359 | 55.215 | 77.874 | 1.245 | 1.00 | 51.69 |
| 2072 | CD | GLU | 359 | 55.241 | 79.379 | 1.308 | 1.00 | 63.61 |
| 2073 | OE1 | GLU | 359 | 54.197 | 79.992 | 1.550 | 1.00 | 70.65 |
| 2074 | OE2 | GLU | 359 | 56.320 | 79.940 | 1.132 | 1.00 | 69.55 |
| 2075 | C | GLU | 359 | 55.638 | 76.809 | -1.721 | 1.00 | 33.19 |
| 2076 | O | GLU | 359 | 56.664 | 77.422 | -1.974 | 1.00 | 36.20 |
| 2077 | N | TYR | 360 | 55.584 | 75.475 | -1.867 | 1.00 | 33.15 |
| 2078 | H | TYR | 360 | 54.723 | 75.002 | -1.843 | 1.00 | 0.00 |
| 2079 | CA | TYR | 360 | 56.814 | 74.710 | -2.053 | 1.00 | 28.52 |
| 2080 | CB | TYR | 360 | 56.902 | 73.528 | -1.079 | 1.00 | 30.16 |
| 2081 | CG | TYR | 360 | 56.910 | 74.022 | 0.333 | 1.00 | 28.83 |
| 2082 | CD1 | TYR | 360 | 55.765 | 73.873 | 1.087 | 1.00 | 30.92 |
| 2083 | CE1 | TYR | 360 | 55.711 | 74.433 | 2.342 | 1.00 | 33.76 |
| 2084 | CD2 | TYR | 360 | 58.022 | 74.677 | 0.824 | 1.00 | 30.38 |
| 2085 | CE2 | TYR | 360 | 57.974 | 75.239 | 2.080 | 1.00 | 32.36 |
| 2086 | CZ | TYR | 360 | 56.813 | 75.114 | 2.823 | 1.00 | 35.09 |
| 2087 | OH | TYR | 360 | 56.737 | 75.692 | 4.073 | 1.00 | 41.75 |

FIG. 5UUU

| Atom | Atom Type | Residue | # | X | Y | Z | OCC | B |
|---|---|---|---|---|---|---|---|---|
| 2088 | HH | TYR | 360 | 55.852 | 75.603 | 4.430 | 1.00 | 0.00 |
| 2089 | C | TYR | 360 | 57.148 | 74.120 | -3.389 | 1.00 | 27.85 |
| 2090 | O | TYR | 360 | 58.243 | 73.583 | -3.525 | 1.00 | 27.93 |
| 2091 | N | ALA | 361 | 56.288 | 74.169 | -4.411 | 1.00 | 27.66 |
| 2092 | H | ALA | 361 | 55.459 | 74.682 | -4.320 | 1.00 | 0.00 |
| 2093 | CA | ALA | 361 | 56.544 | 73.494 | -5.678 | 1.00 | 28.82 |
| 2094 | CB | ALA | 361 | 55.328 | 73.717 | -6.600 | 1.00 | 26.34 |
| 2095 | C | ALA | 361 | 57.818 | 73.954 | -6.355 | 1.00 | 32.26 |
| 2096 | O | ALA | 361 | 58.461 | 73.249 | -7.116 | 1.00 | 35.01 |
| 2097 | N | CYS | 362 | 58.273 | 75.178 | -6.133 | 1.00 | 38.50 |
| 2098 | H | CYS | 362 | 57.694 | 75.795 | -5.620 | 1.00 | 0.00 |
| 2099 | CA | CYS | 362 | 59.576 | 75.578 | -6.659 | 1.00 | 42.41 |
| 2100 | C | CYS | 362 | 60.768 | 74.919 | -5.987 | 1.00 | 41.51 |
| 2101 | O | CYS | 362 | 61.761 | 74.529 | -6.575 | 1.00 | 41.46 |
| 2102 | CB | CYS | 362 | 59.746 | 77.086 | -6.546 | 1.00 | 47.61 |
| 2103 | SG | CYS | 362 | 61.400 | 77.655 | -7.050 | 1.00 | 64.18 |
| 2104 | N | SER | 363 | 60.741 | 74.757 | -4.681 | 1.00 | 40.95 |
| 2105 | H | SER | 363 | 59.909 | 74.803 | -4.165 | 1.00 | 0.00 |
| 2106 | CA | SER | 363 | 61.955 | 74.338 | -4.026 | 1.00 | 43.35 |
| 2107 | CB | SER | 363 | 62.122 | 75.236 | -2.800 | 1.00 | 44.65 |
| 2108 | OG | SER | 363 | 60.899 | 75.837 | -2.362 | 1.00 | 53.93 |
| 2109 | HG | SER | 363 | 60.553 | 76.414 | -3.046 | 1.00 | 0.00 |
| 2110 | C | SER | 363 | 61.985 | 72.866 | -3.661 | 1.00 | 40.77 |
| 2111 | O | SER | 363 | 63.036 | 72.255 | -3.593 | 1.00 | 43.37 |
| 2112 | N | CYS | 364 | 60.857 | 72.220 | -3.399 | 1.00 | 38.31 |
| 2113 | H | CYS | 364 | 59.976 | 72.633 | -3.542 | 1.00 | 0.00 |
| 2114 | CA | CYS | 364 | 60.937 | 70.839 | -2.979 | 1.00 | 33.39 |
| 2115 | CB | CYS | 364 | 60.056 | 70.623 | -1.755 | 1.00 | 32.55 |
| 2116 | SG | CYS | 364 | 60.508 | 71.767 | -0.422 | 1.00 | 40.02 |

FIG. 5VVV

| Atom | Atom Type | Residue | # | X | Y | Z | OCC | B |
|---|---|---|---|---|---|---|---|---|
| 2117 | C | CYS | 364 | 60.478 | 69.967 | -4.121 | 1.00 | 29.84 |
| 2118 | O | CYS | 364 | 59.610 | 70.346 | -4.887 | 1.00 | 30.07 |
| 2119 | N | ASP | 365 | 61.025 | 68.770 | -4.300 | 1.00 | 28.01 |
| 2120 | H | ASP | 365 | 61.859 | 68.579 | -3.828 | 1.00 | 0.00 |
| 2121 | CA | ASP | 365 | 60.406 | 67.784 | -5.164 | 1.00 | 27.07 |
| 2122 | CB | ASP | 365 | 61.379 | 66.619 | -5.419 | 1.00 | 27.73 |
| 2123 | CG | ASP | 365 | 61.757 | 65.825 | -4.171 | 1.00 | 31.83 |
| 2124 | OD1 | ASP | 365 | 61.026 | 64.918 | -3.783 | 1.00 | 34.71 |
| 2125 | OD2 | ASP | 365 | 62.805 | 66.094 | -3.599 | 1.00 | 42.02 |
| 2126 | C | ASP | 365 | 59.111 | 67.254 | -4.538 | 1.00 | 28.95 |
| 2127 | O | ASP | 365 | 58.838 | 67.420 | -3.343 | 1.00 | 27.98 |
| 2128 | N | VAL | 366 | 58.277 | 66.590 | -5.336 | 1.00 | 27.55 |
| 2129 | H | VAL | 366 | 58.544 | 66.434 | -6.268 | 1.00 | 0.00 |
| 2130 | CA | VAL | 366 | 56.968 | 66.183 | -4.857 | 1.00 | 27.84 |
| 2131 | CB | VAL | 366 | 56.251 | 65.513 | -6.051 | 1.00 | 24.13 |
| 2132 | CG1 | VAL | 366 | 55.102 | 64.601 | -5.672 | 1.00 | 23.78 |
| 2133 | CG2 | VAL | 366 | 55.629 | 66.654 | -6.848 | 1.00 | 23.21 |
| 2134 | C | VAL | 366 | 57.007 | 65.309 | -3.611 | 1.00 | 28.22 |
| 2135 | O | VAL | 366 | 56.256 | 65.536 | -2.674 | 1.00 | 30.81 |
| 2136 | N | GLU | 367 | 57.856 | 64.298 | -3.489 | 1.00 | 28.49 |
| 2137 | H | GLU | 367 | 58.450 | 64.111 | -4.237 | 1.00 | 0.00 |
| 2138 | CA | GLU | 367 | 57.867 | 63.516 | -2.259 | 1.00 | 27.85 |
| 2139 | CB | GLU | 367 | 58.939 | 62.428 | -2.289 | 1.00 | 26.64 |
| 2140 | CG | GLU | 367 | 58.553 | 61.219 | -3.144 | 1.00 | 28.69 |
| 2141 | CD | GLU | 367 | 59.442 | 60.019 | -2.820 | 1.00 | 37.41 |
| 2142 | OE1 | GLU | 367 | 59.643 | 59.736 | -1.632 | 1.00 | 42.87 |
| 2143 | OE2 | GLU | 367 | 59.937 | 59.388 | -3.767 | 1.00 | 37.88 |
| 2144 | C | GLU | 367 | 58.106 | 64.352 | -1.012 | 1.00 | 28.61 |
| 2145 | O | GLU | 367 | 57.604 | 64.052 | 0.059 | 1.00 | 31.13 |

FIG. 5WWW

| Atom | Atom Type | Residue | # | X | Y | Z | OCC | B |
|---|---|---|---|---|---|---|---|---|
| 2146 | N | GLU | 368 | 58.872 | 65.437 | -1.099 | 1.00 | 28.39 |
| 2147 | H | GLU | 368 | 59.242 | 65.725 | -1.959 | 1.00 | 0.00 |
| 2148 | CA | GLU | 368 | 59.094 | 66.231 | 0.076 | 1.00 | 26.65 |
| 2149 | CB | GLU | 368 | 60.278 | 67.145 | -0.069 | 1.00 | 34.26 |
| 2150 | CG | GLU | 368 | 61.017 | 66.888 | 1.244 | 1.00 | 53.59 |
| 2151 | CD | GLU | 368 | 61.471 | 68.195 | 1.841 | 1.00 | 63.52 |
| 2152 | OE1 | GLU | 368 | 61.848 | 69.099 | 1.078 | 1.00 | 71.58 |
| 2153 | OE2 | GLU | 368 | 61.444 | 68.298 | 3.071 | 1.00 | 64.40 |
| 2154 | C | GLU | 368 | 57.923 | 67.082 | 0.396 | 1.00 | 23.42 |
| 2155 | O | GLU | 368 | 57.561 | 67.224 | 1.555 | 1.00 | 27.18 |
| 2156 | N | ILE | 369 | 57.268 | 67.677 | -0.591 | 1.00 | 22.22 |
| 2157 | H | ILE | 369 | 57.595 | 67.596 | -1.513 | 1.00 | 0.00 |
| 2158 | CA | ILE | 369 | 56.027 | 68.395 | -0.295 | 1.00 | 19.89 |
| 2159 | CB | ILE | 369 | 55.403 | 68.931 | -1.624 | 1.00 | 22.54 |
| 2160 | CG2 | ILE | 369 | 54.089 | 69.671 | -1.355 | 1.00 | 20.28 |
| 2161 | CG1 | ILE | 369 | 56.360 | 69.917 | -2.281 | 1.00 | 17.77 |
| 2162 | CD1 | ILE | 369 | 55.911 | 70.256 | -3.701 | 1.00 | 15.38 |
| 2163 | C | ILE | 369 | 55.024 | 67.497 | 0.435 | 1.00 | 20.18 |
| 2164 | O | ILE | 369 | 54.331 | 67.885 | 1.371 | 1.00 | 20.19 |
| 2165 | N | PHE | 370 | 54.923 | 66.241 | 0.020 | 1.00 | 21.39 |
| 2166 | H | PHE | 370 | 55.470 | 65.932 | -0.733 | 1.00 | 0.00 |
| 2167 | CA | PHE | 370 | 53.962 | 65.359 | 0.654 | 1.00 | 23.30 |
| 2168 | CB | PHE | 370 | 53.842 | 64.029 | -0.121 | 1.00 | 23.30 |
| 2169 | CG | PHE | 370 | 53.140 | 64.222 | -1.451 | 1.00 | 23.92 |
| 2170 | CD1 | PHE | 370 | 53.037 | 63.153 | -2.304 | 1.00 | 27.01 |
| 2171 | CD2 | PHE | 370 | 52.624 | 65.444 | -1.841 | 1.00 | 29.88 |
| 2172 | CE1 | PHE | 370 | 52.427 | 63.311 | -3.533 | 1.00 | 26.34 |
| 2173 | CE2 | PHE | 370 | 52.013 | 65.595 | -3.069 | 1.00 | 27.67 |
| 2174 | CZ | PHE | 370 | 51.906 | 64.521 | -3.919 | 1.00 | 27.89 |

FIG. 5XXX

| Atom | Atom Type | Residue | # | X | Y | Z | OCC | B |
|---|---|---|---|---|---|---|---|---|
| 2175 | C | PHE | 370 | 54.360 | 65.076 | 2.069 | 1.00 | 23.38 |
| 2176 | O | PHE | 370 | 53.543 | 65.031 | 2.978 | 1.00 | 24.64 |
| 2177 | N | ARG | 371 | 55.654 | 64.883 | 2.314 | 1.00 | 24.62 |
| 2178 | H | ARG | 371 | 56.291 | 64.804 | 1.573 | 1.00 | 0.00 |
| 2179 | CA | ARG | 371 | 56.103 | 64.783 | 3.683 | 1.00 | 26.21 |
| 2180 | CB | ARG | 371 | 57.611 | 64.627 | 3.722 | 1.00 | 25.42 |
| 2181 | CG | ARG | 371 | 57.954 | 64.338 | 5.180 | 1.00 | 26.24 |
| 2182 | CD | ARG | 371 | 59.453 | 64.358 | 5.411 | 1.00 | 27.46 |
| 2183 | NE | ARG | 371 | 60.022 | 65.650 | 5.122 | 1.00 | 34.21 |
| 2184 | HE | ARG | 371 | 60.521 | 65.766 | 4.286 | 1.00 | 0.00 |
| 2185 | CZ | ARG | 371 | 59.899 | 66.694 | 5.969 | 1.00 | 40.22 |
| 2186 | NH1 | ARG | 371 | 59.207 | 66.648 | 7.152 | 1.00 | 39.64 |
| 2187 | HH11 | ARG | 371 | 58.750 | 65.805 | 7.435 | 1.00 | 0.00 |
| 2188 | HH12 | ARG | 371 | 59.163 | 67.463 | 7.729 | 1.00 | 0.00 |
| 2189 | NH2 | ARG | 371 | 60.525 | 67.849 | 5.632 | 1.00 | 39.43 |
| 2190 | HH21 | ARG | 371 | 61.067 | 67.884 | 4.795 | 1.00 | 0.00 |
| 2191 | HH22 | ARG | 371 | 60.471 | 68.649 | 6.231 | 1.00 | 0.00 |
| 2192 | C | ARG | 371 | 55.704 | 65.999 | 4.505 | 1.00 | 29.69 |
| 2193 | O | ARG | 371 | 55.105 | 65.907 | 5.576 | 1.00 | 32.42 |
| 2194 | N | LYS | 372 | 56.020 | 67.200 | 4.020 | 1.00 | 26.46 |
| 2195 | H | LYS | 372 | 56.525 | 67.281 | 3.182 | 1.00 | 0.00 |
| 2196 | CA | LYS | 372 | 55.576 | 68.377 | 4.733 | 1.00 | 23.67 |
| 2197 | CB | LYS | 372 | 56.008 | 69.609 | 3.976 | 1.00 | 25.18 |
| 2198 | CG | LYS | 372 | 57.506 | 69.718 | 4.053 | 1.00 | 21.18 |
| 2199 | CD | LYS | 372 | 57.933 | 70.852 | 3.136 | 1.00 | 33.26 |
| 2200 | CE | LYS | 372 | 59.042 | 71.666 | 3.789 | 1.00 | 42.84 |
| 2201 | NZ | LYS | 372 | 58.499 | 72.323 | 4.969 | 1.00 | 50.90 |
| 2202 | HZ1 | LYS | 372 | 58.138 | 71.612 | 5.636 | 1.00 | 0.00 |
| 2203 | HZ2 | LYS | 372 | 57.717 | 72.944 | 4.674 | 1.00 | 0.00 |

FIG. 5YYY

| Atom | Atom Type | Residue | # | X | Y | Z | OCC | B |
|---|---|---|---|---|---|---|---|---|
| 2204 | HZ3 | LYS | 372 | 59.239 | 72.893 | 5.426 | 1.00 | 0.00 |
| 2205 | C | LYS | 372 | 54.085 | 68.434 | 4.960 | 1.00 | 22.44 |
| 2206 | O | LYS | 372 | 53.617 | 68.867 | 6.008 | 1.00 | 25.03 |
| 2207 | N | VAL | 373 | 53.240 | 68.015 | 4.026 | 1.00 | 24.85 |
| 2208 | H | VAL | 373 | 53.577 | 67.723 | 3.154 | 1.00 | 0.00 |
| 2209 | CA | VAL | 373 | 51.813 | 67.977 | 4.333 | 1.00 | 26.14 |
| 2210 | CB | VAL | 373 | 50.927 | 67.520 | 3.121 | 1.00 | 29.33 |
| 2211 | CG1 | VAL | 373 | 49.442 | 67.520 | 3.541 | 1.00 | 23.06 |
| 2212 | CG2 | VAL | 373 | 51.108 | 68.476 | 1.933 | 1.00 | 20.17 |
| 2213 | C | VAL | 373 | 51.588 | 67.006 | 5.471 | 1.00 | 26.25 |
| 2214 | O | VAL | 373 | 50.792 | 67.332 | 6.336 | 1.00 | 25.40 |
| 2215 | N | ARG | 374 | 52.251 | 65.839 | 5.540 | 1.00 | 22.91 |
| 2216 | H | ARG | 374 | 52.897 | 65.603 | 4.838 | 1.00 | 0.00 |
| 2217 | CA | ARG | 374 | 52.025 | 64.926 | 6.660 | 1.00 | 24.92 |
| 2218 | CB | ARG | 374 | 52.827 | 63.601 | 6.511 | 1.00 | 24.92 |
| 2219 | CG | ARG | 374 | 52.332 | 62.777 | 5.307 | 1.00 | 26.50 |
| 2220 | CD | ARG | 374 | 52.822 | 61.333 | 5.253 | 1.00 | 21.69 |
| 2221 | NE | ARG | 374 | 54.262 | 61.249 | 5.278 | 1.00 | 21.59 |
| 2222 | HE | ARG | 374 | 54.727 | 61.264 | 6.141 | 1.00 | 0.00 |
| 2223 | CZ | ARG | 374 | 54.973 | 61.142 | 4.161 | 1.00 | 19.13 |
| 2224 | NH1 | ARG | 374 | 54.335 | 61.136 | 2.971 | 1.00 | 22.36 |
| 2225 | HH11 | ARG | 374 | 53.340 | 61.217 | 2.923 | 1.00 | 0.00 |
| 2226 | HH12 | ARG | 374 | 54.864 | 61.061 | 2.126 | 1.00 | 0.00 |
| 2227 | NH2 | ARG | 374 | 56.344 | 61.046 | 4.208 | 1.00 | 22.93 |
| 2228 | HH21 | ARG | 374 | 56.811 | 61.053 | 5.094 | 1.00 | 0.00 |
| 2229 | HH22 | ARG | 374 | 56.874 | 60.966 | 3.362 | 1.00 | 0.00 |
| 2230 | C | ARG | 374 | 52.423 | 65.570 | 7.958 | 1.00 | 23.27 |
| 2231 | O | ARG | 374 | 51.724 | 65.539 | 8.955 | 1.00 | 20.79 |
| 2232 | N | PHE | 375 | 53.581 | 66.204 | 7.996 | 1.00 | 24.10 |

FIG. 5ZZZ

| Atom | Atom Type | Residue | # | X | Y | Z | OCC | B |
|---|---|---|---|---|---|---|---|---|
| 2233 | H | PHE | 375 | 54.147 | 66.181 | 7.193 | 1.00 | 0.00 |
| 2234 | CA | PHE | 375 | 54.025 | 66.896 | 9.187 | 1.00 | 23.34 |
| 2235 | CB | PHE | 375 | 55.388 | 67.523 | 8.828 | 1.00 | 29.16 |
| 2236 | CG | PHE | 375 | 56.010 | 68.272 | 9.989 | 1.00 | 35.30 |
| 2237 | CD1 | PHE | 375 | 56.926 | 67.655 | 10.803 | 1.00 | 36.99 |
| 2238 | CD2 | PHE | 375 | 55.684 | 69.589 | 10.221 | 1.00 | 38.65 |
| 2239 | CE1 | PHE | 375 | 57.518 | 68.348 | 11.838 | 1.00 | 36.47 |
| 2240 | CE2 | PHE | 375 | 56.281 | 70.277 | 11.255 | 1.00 | 38.44 |
| 2241 | CZ | PHE | 375 | 57.202 | 69.659 | 12.064 | 1.00 | 37.61 |
| 2242 | C | PHE | 375 | 52.982 | 67.917 | 9.664 | 1.00 | 28.21 |
| 2243 | O | PHE | 375 | 52.775 | 68.135 | 10.857 | 1.00 | 28.91 |
| 2244 | N | SER | 376 | 52.260 | 68.589 | 8.742 | 1.00 | 28.48 |
| 2245 | H | SER | 376 | 52.414 | 68.468 | 7.783 | 1.00 | 0.00 |
| 2246 | CA | SER | 376 | 51.281 | 69.562 | 9.208 | 1.00 | 28.11 |
| 2247 | CB | SER | 376 | 50.715 | 70.398 | 8.047 | 1.00 | 24.30 |
| 2248 | OG | SER | 376 | 49.984 | 69.740 | 7.034 | 1.00 | 26.36 |
| 2249 | HG | SER | 376 | 50.480 | 68.972 | 6.709 | 1.00 | 0.00 |
| 2250 | C | SER | 376 | 50.124 | 68.979 | 9.960 | 1.00 | 30.03 |
| 2251 | O | SER | 376 | 49.395 | 69.683 | 10.647 | 1.00 | 27.69 |
| 2252 | N | PHE | 377 | 49.927 | 67.671 | 9.838 | 1.00 | 33.33 |
| 2253 | H | PHE | 377 | 50.511 | 67.127 | 9.265 | 1.00 | 0.00 |
| 2254 | CA | PHE | 377 | 48.882 | 66.990 | 10.570 | 1.00 | 30.24 |
| 2255 | CB | PHE | 377 | 48.276 | 65.883 | 9.691 | 1.00 | 21.45 |
| 2256 | CG | PHE | 377 | 47.359 | 66.445 | 8.647 | 1.00 | 21.79 |
| 2257 | CD1 | PHE | 377 | 47.815 | 66.654 | 7.363 | 1.00 | 23.05 |
| 2258 | CD2 | PHE | 377 | 46.040 | 66.714 | 8.961 | 1.00 | 22.87 |
| 2259 | CE1 | PHE | 377 | 46.933 | 67.097 | 6.390 | 1.00 | 23.70 |
| 2260 | CE2 | PHE | 377 | 45.173 | 67.155 | 7.981 | 1.00 | 21.35 |
| 2261 | CZ | PHE | 377 | 45.613 | 67.337 | 6.688 | 1.00 | 16.45 |

FIG. 5AAAA

| Atom | Atom Type | Residue | # | X | Y | Z | OCC | B |
|---|---|---|---|---|---|---|---|---|
| 2262 | C | PHE | 377 | 49.407 | 66.381 | 11.860 | 1.00 | 30.42 |
| 2263 | O | PHE | 377 | 48.713 | 65.615 | 12.528 | 1.00 | 29.72 |
| 2264 | N | GLU | 378 | 50.634 | 66.675 | 12.279 | 1.00 | 30.87 |
| 2265 | H | GLU | 378 | 51.151 | 67.389 | 11.850 | 1.00 | 0.00 |
| 2266 | CA | GLU | 378 | 51.169 | 65.910 | 13.374 | 1.00 | 35.50 |
| 2267 | CB | GLU | 378 | 52.649 | 66.182 | 13.534 | 1.00 | 33.01 |
| 2268 | CG | GLU | 378 | 53.146 | 64.886 | 14.168 | 1.00 | 38.65 |
| 2269 | CD | GLU | 378 | 54.632 | 64.790 | 14.234 | 1.00 | 42.24 |
| 2270 | OE1 | GLU | 378 | 55.130 | 63.668 | 14.315 | 1.00 | 45.42 |
| 2271 | OE2 | GLU | 378 | 55.292 | 65.826 | 14.210 | 1.00 | 51.72 |
| 2272 | C | GLU | 378 | 50.502 | 66.092 | 14.719 | 1.00 | 36.27 |
| 2273 | O | GLU | 378 | 50.366 | 65.153 | 15.483 | 1.00 | 39.55 |
| 2274 | N | GLN | 379 | 50.053 | 67.255 | 15.116 | 1.00 | 39.19 |
| 2275 | H | GLN | 379 | 50.149 | 68.039 | 14.543 | 1.00 | 0.00 |
| 2276 | CA | GLN | 379 | 49.268 | 67.367 | 16.328 | 1.00 | 48.22 |
| 2277 | CB | GLN | 379 | 49.380 | 68.788 | 16.896 | 1.00 | 56.51 |
| 2278 | CG | GLN | 379 | 50.771 | 69.437 | 16.941 | 1.00 | 63.32 |
| 2279 | CD | GLN | 379 | 51.711 | 68.603 | 17.767 | 1.00 | 69.92 |
| 2280 | OE1 | GLN | 379 | 51.480 | 68.345 | 18.938 | 1.00 | 74.88 |
| 2281 | NE2 | GLN | 379 | 52.809 | 68.101 | 17.225 | 1.00 | 72.82 |
| 2282 | HE21 | GLN | 379 | 52.996 | 68.281 | 16.281 | 1.00 | 0.00 |
| 2283 | HE22 | GLN | 379 | 53.371 | 67.564 | 17.826 | 1.00 | 0.00 |
| 2284 | C | GLN | 379 | 47.797 | 67.066 | 16.009 | 1.00 | 50.39 |
| 2285 | O | GLN | 379 | 47.241 | 67.723 | 15.130 | 1.00 | 51.95 |
| 2286 | N | PRO | 380 | 47.098 | 66.157 | 16.602 | 1.00 | 51.98 |
| 2287 | CD | PRO | 380 | 47.634 | 65.095 | 17.439 | 1.00 | 50.16 |
| 2288 | CA | PRO | 380 | 45.670 | 65.984 | 16.367 | 1.00 | 58.10 |
| 2289 | CB | PRO | 380 | 45.261 | 64.815 | 17.243 | 1.00 | 53.72 |
| 2290 | CG | PRO | 380 | 46.548 | 64.024 | 17.310 | 1.00 | 49.03 |

FIG. 5BBBB

| Atom | Atom Type | Residue | # | X | Y | Z | OCC | B |
|---|---|---|---|---|---|---|---|---|
| 2291 | C | PRO | 380 | 44.890 | 67.242 | 16.664 | 1.00 | 67.86 |
| 2292 | O | PRO | 380 | 44.736 | 67.733 | 17.776 | 1.00 | 70.34 |
| 2293 | N | ASP | 381 | 44.366 | 67.794 | 15.586 | 1.00 | 77.19 |
| 2294 | H | ASP | 381 | 44.538 | 67.356 | 14.721 | 1.00 | 0.00 |
| 2295 | CA | ASP | 381 | 43.596 | 69.021 | 15.617 | 1.00 | 83.19 |
| 2296 | CB | ASP | 381 | 43.541 | 69.494 | 14.153 | 1.00 | 90.96 |
| 2297 | CG | ASP | 381 | 43.014 | 70.910 | 13.938 | 1.00 | 908.27 |
| 2298 | OD1 | ASP | 381 | 43.143 | 71.746 | 14.843 | 1.00 | 11.43 |
| 2299 | OD2 | ASP | 381 | 42.481 | 71.167 | 12.846 | 1.00 | 102.13 |
| 2300 | C | ASP | 381 | 42.223 | 68.750 | 16.235 | 1.00 | 83.61 |
| 2301 | O | ASP | 381 | 41.197 | 69.227 | 15.766 | 1.00 | 86.07 |
| 2302 | N | GLY | 382 | 42.096 | 67.981 | 17.316 | 1.00 | 80.88 |
| 2303 | H | GLY | 382 | 42.906 | 67.764 | 17.831 | 1.00 | 0.00 |
| 2304 | CA | GLY | 382 | 40.780 | 67.478 | 17.697 | 1.00 | 78.25 |
| 2305 | C | GLY | 382 | 40.321 | 66.448 | 16.669 | 1.00 | 75.15 |
| 2306 | O | GLY | 382 | 40.458 | 65.247 | 16.841 | 1.00 | 79.53 |
| 2307 | N | ARG | 383 | 39.759 | 66.873 | 15.545 | 1.00 | 69.56 |
| 2308 | H | ARG | 383 | 39.519 | 67.824 | 15.480 | 1.00 | 0.00 |
| 2309 | CA | ARG | 383 | 39.629 | 66.003 | 14.381 | 1.00 | 64.31 |
| 2310 | CB | ARG | 383 | 39.071 | 66.738 | 13.173 | 1.00 | 67.34 |
| 2311 | CG | ARG | 383 | 37.832 | 67.576 | 13.414 | 1.00 | 69.84 |
| 2312 | CD | ARG | 383 | 36.696 | 66.741 | 13.993 | 1.00 | 75.22 |
| 2313 | NE | ARG | 383 | 35.525 | 67.573 | 14.194 | 1.00 | 78.64 |
| 2314 | HE | ARG | 383 | 35.556 | 68.516 | 13.929 | 1.00 | 0.00 |
| 2315 | CZ | ARG | 383 | 34.408 | 67.087 | 14.732 | 1.00 | 79.29 |
| 2316 | NH1 | ARG | 383 | 33.341 | 67.925 | 14.847 | 1.00 | 80.15 |
| 2317 | HH11 | ARG | 383 | 33.413 | 68.873 | 14.534 | 1.00 | 0.00 |
| 2318 | HH12 | ARG | 383 | 32.487 | 67.594 | 15.250 | 1.00 | 0.00 |
| 2319 | NH2 | ARG | 383 | 34.322 | 65.793 | 15.173 | 1.00 | 76.12 |

FIG. 5CCCC

| Atom | Atom Type | Residue | # | X | Y | Z | OCC | B |
|---|---|---|---|---|---|---|---|---|
| 2320 | HH21 | ARG | 383 | 35.108 | 65.180 | 15.101 | 1.00 | 0.00 |
| 2321 | HH22 | ARG | 383 | 33.469 | 65.461 | 15.576 | 1.00 | 0.00 |
| 2322 | C | ARG | 383 | 41.041 | 65.557 | 14.005 | 1.00 | 59.27 |
| 2323 | O | ARG | 383 | 41.896 | 66.385 | 13.710 | 1.00 | 63.51 |
| 2324 | N | ALA | 384 | 41.392 | 64.279 | 13.985 | 1.00 | 51.06 |
| 2325 | H | ALA | 384 | 40.809 | 63.578 | 14.357 | 1.00 | 0.00 |
| 2326 | CA | ALA | 384 | 42.711 | 63.902 | 13.518 | 1.00 | 43.97 |
| 2327 | CB | ALA | 384 | 43.392 | 63.101 | 14.618 | 1.00 | 39.32 |
| 2328 | C | ALA | 384 | 42.614 | 63.088 | 12.237 | 1.00 | 41.10 |
| 2329 | O | ALA | 384 | 41.666 | 62.329 | 12.029 | 1.00 | 42.25 |
| 2330 | N | GLN | 385 | 43.604 | 63.245 | 11.349 | 1.00 | 30.93 |
| 2331 | H | GLN | 385 | 44.264 | 63.968 | 11.422 | 1.00 | 0.00 |
| 2332 | CA | GLN | 385 | 43.794 | 62.325 | 10.258 | 1.00 | 26.81 |
| 2333 | CB | GLN | 385 | 42.964 | 62.733 | 9.034 | 1.00 | 23.54 |
| 2334 | CG | GLN | 385 | 43.318 | 64.098 | 8.481 | 1.00 | 27.75 |
| 2335 | CD | GLN | 385 | 42.355 | 64.422 | 7.399 | 1.00 | 29.52 |
| 2336 | OE1 | GLN | 385 | 41.375 | 65.120 | 7.586 | 1.00 | 30.67 |
| 2337 | NE2 | GLN | 385 | 42.598 | 63.875 | 6.223 | 1.00 | 29.71 |
| 2338 | HE21 | GLN | 385 | 43.370 | 63.272 | 6.110 | 1.00 | 0.00 |
| 2339 | HE22 | GLN | 385 | 42.007 | 64.105 | 5.478 | 1.00 | 0.00 |
| 2340 | C | GLN | 385 | 45.276 | 62.394 | 9.937 | 1.00 | 26.43 |
| 2341 | O | GLN | 385 | 45.955 | 63.312 | 10.363 | 1.00 | 26.69 |
| 2342 | N | MET | 386 | 45.844 | 61.457 | 9.197 | 1.00 | 25.50 |
| 2343 | H | MET | 386 | 45.253 | 60.770 | 8.827 | 1.00 | 0.00 |
| 2344 | CA | MET | 386 | 47.281 | 61.417 | 8.921 | 1.00 | 25.53 |
| 2345 | CB | MET | 386 | 47.980 | 60.448 | 9.881 | 1.00 | 22.77 |
| 2346 | CG | MET | 386 | 49.459 | 60.203 | 9.609 | 1.00 | 22.60 |
| 2347 | SD | MET | 386 | 50.369 | 61.710 | 9.227 | 1.00 | 24.47 |
| 2348 | CE | MET | 386 | 50.297 | 62.580 | 10.768 | 1.00 | 22.26 |

FIG. 5DDDD

| Atom | Atom Type | Residue | # | X | Y | Z | OCC | B |
|---|---|---|---|---|---|---|---|---|
| 2349 | C | MET | 386 | 47.376 | 60.904 | 7.503 | 1.00 | 25.56 |
| 2350 | O | MET | 386 | 47.187 | 59.706 | 7.306 | 1.00 | 24.42 |
| 2351 | N | PRO | 387 | 47.623 | 61.710 | 6.539 | 1.00 | 24.46 |
| 2352 | CD | PRO | 387 | 47.479 | 63.144 | 6.670 | 1.00 | 25.50 |
| 2353 | CA | PRO | 387 | 47.706 | 61.309 | 5.134 | 1.00 | 22.74 |
| 2354 | CB | PRO | 387 | 47.813 | 62.609 | 4.355 | 1.00 | 21.24 |
| 2355 | CG | PRO | 387 | 48.153 | 63.635 | 5.396 | 1.00 | 25.14 |
| 2356 | C | PRO | 387 | 48.825 | 60.365 | 4.853 | 1.00 | 24.30 |
| 2357 | O | PRO | 387 | 49.849 | 60.377 | 5.523 | 1.00 | 23.73 |
| 2358 | N | THR | 388 | 48.671 | 59.504 | 3.859 | 1.00 | 22.51 |
| 2359 | H | THR | 388 | 47.904 | 59.580 | 3.255 | 1.00 | 0.00 |
| 2360 | CA | THR | 388 | 49.646 | 58.448 | 3.685 | 1.00 | 23.26 |
| 2361 | CB | THR | 388 | 49.037 | 57.083 | 4.100 | 1.00 | 26.15 |
| 2362 | OG1 | THR | 388 | 48.399 | 57.238 | 5.359 | 1.00 | 34.81 |
| 2363 | HG1 | THR | 388 | 49.021 | 57.669 | 5.956 | 1.00 | 0.00 |
| 2364 | CG2 | THR | 388 | 50.105 | 56.009 | 4.257 | 1.00 | 24.27 |
| 2365 | C | THR | 388 | 50.062 | 58.416 | 2.233 | 1.00 | 19.72 |
| 2366 | O | THR | 388 | 49.262 | 58.508 | 1.316 | 1.00 | 20.10 |
| 2367 | N | THR | 389 | 51.357 | 58.279 | 2.016 | 1.00 | 20.14 |
| 2368 | H | THR | 389 | 51.974 | 58.285 | 2.771 | 1.00 | 0.00 |
| 2369 | CA | THR | 389 | 51.933 | 58.099 | 0.709 | 1.00 | 22.14 |
| 2370 | CB | THR | 389 | 53.304 | 58.762 | 0.775 | 1.00 | 22.05 |
| 2371 | OG1 | THR | 389 | 53.043 | 60.143 | 0.521 | 1.00 | 32.86 |
| 2372 | HG1 | THR | 389 | 52.584 | 60.204 | -0.321 | 1.00 | 0.00 |
| 2373 | CG2 | THR | 389 | 54.305 | 58.266 | -0.223 | 1.00 | 26.26 |
| 2374 | C | THR | 389 | 51.981 | 56.611 | 0.446 | 1.00 | 27.05 |
| 2375 | O | THR | 389 | 52.421 | 55.845 | 1.307 | 1.00 | 23.21 |
| 2376 | N | GLU | 390 | 51.532 | 56.183 | -0.742 | 1.00 | 23.67 |
| 2377 | H | GLU | 390 | 51.265 | 56.821 | -1.440 | 1.00 | 0.00 |

FIG. 5EEEE

| Atom | Atom Type | Residue | # | X | Y | Z | OCC | B |
|---|---|---|---|---|---|---|---|---|
| 2378 | CA | GLU | 390 | 51.461 | 54.770 | -1.017 | 1.00 | 21.51 |
| 2379 | CB | GLU | 390 | 49.993 | 54.334 | -0.902 | 1.00 | 27.17 |
| 2380 | CG | GLU | 390 | 49.716 | 54.258 | 0.612 | 1.00 | 35.02 |
| 2381 | CD | GLU | 390 | 48.453 | 53.567 | 1.001 | 1.00 | 38.42 |
| 2382 | OE1 | GLU | 390 | 47.644 | 53.290 | 0.129 | 1.00 | 50.83 |
| 2383 | OE2 | GLU | 390 | 48.274 | 53.314 | 2.192 | 1.00 | 47.46 |
| 2384 | C | GLU | 390 | 52.032 | 54.416 | -2.351 | 1.00 | 22.05 |
| 2385 | O | GLU | 390 | 52.148 | 55.236 | -3.244 | 1.00 | 25.04 |
| 2386 | N | ARG | 391 | 52.406 | 53.145 | -2.449 | 1.00 | 20.72 |
| 2387 | H | ARG | 391 | 52.314 | 52.613 | -1.634 | 1.00 | 0.00 |
| 2388 | CA | ARG | 391 | 52.871 | 52.472 | -3.655 | 1.00 | 20.99 |
| 2389 | CB | ARG | 391 | 51.677 | 52.087 | -4.548 | 1.00 | 24.04 |
| 2390 | CG | ARG | 391 | 51.351 | 50.594 | -4.650 | 1.00 | 27.32 |
| 2391 | CD | ARG | 391 | 51.041 | 50.062 | -6.066 | 1.00 | 27.94 |
| 2392 | NE | ARG | 391 | 49.890 | 49.159 | -6.094 | 1.00 | 36.16 |
| 2393 | HE | ARG | 391 | 49.248 | 49.211 | -5.356 | 1.00 | 0.00 |
| 2394 | CZ | ARG | 391 | 49.642 | 48.255 | -7.068 | 1.00 | 38.21 |
| 2395 | NH1 | ARG | 391 | 50.302 | 48.156 | -8.246 | 1.00 | 39.70 |
| 2396 | HH11 | ARG | 391 | 51.042 | 48.794 | -8.455 | 1.00 | 0.00 |
| 2397 | HH12 | ARG | 391 | 50.046 | 47.453 | -8.910 | 1.00 | 0.00 |
| 2398 | NH2 | ARG | 391 | 48.749 | 47.269 | -6.849 | 1.00 | 47.46 |
| 2399 | HH21 | ARG | 391 | 48.279 | 47.209 | -5.968 | 1.00 | 0.00 |
| 2400 | HH22 | ARG | 391 | 48.561 | 46.597 | -7.567 | 1.00 | 0.00 |
| 2401 | C | ARG | 391 | 53.842 | 53.303 | -4.477 | 1.00 | 24.89 |
| 2402 | O | ARG | 391 | 53.590 | 53.655 | -5.630 | 1.00 | 24.46 |
| 2403 | N | VAL | 392 | 54.998 | 53.634 | -3.892 | 1.00 | 25.48 |
| 2404 | H | VAL | 392 | 55.287 | 53.159 | -3.085 | 1.00 | 0.00 |
| 2405 | CA | VAL | 392 | 55.880 | 54.629 | -4.494 | 1.00 | 21.84 |
| 2406 | CB | VAL | 392 | 56.630 | 55.422 | -3.404 | 1.00 | 19.22 |

FIG. 5FFFF

| Atom | Atom Type | Residue | # | X | Y | Z | OCC | B |
|---|---|---|---|---|---|---|---|---|
| 2407 | CG1 | VAL | 392 | 57.408 | 56.628 | -3.936 | 1.00 | 11.40 |
| 2408 | CG2 | VAL | 392 | 55.579 | 55.918 | -2.436 | 1.00 | 18.72 |
| 2409 | C | VAL | 392 | 56.865 | 53.948 | -5.392 | 1.00 | 24.62 |
| 2410 | O | VAL | 392 | 57.628 | 53.121 | -4.915 | 1.00 | 20.00 |
| 2411 | N | THR | 393 | 56.890 | 54.255 | -6.691 | 1.00 | 23.61 |
| 2412 | H | THR | 393 | 56.183 | 54.810 | -7.081 | 1.00 | 0.00 |
| 2413 | CA | THR | 393 | 57.958 | 53.731 | -7.506 | 1.00 | 20.89 |
| 2414 | CB | THR | 393 | 57.450 | 52.681 | -8.535 | 1.00 | 21.30 |
| 2415 | OG1 | THR | 393 | 56.238 | 53.135 | -9.148 | 1.00 | 22.68 |
| 2416 | HG1 | THR | 393 | 56.027 | 52.485 | -9.822 | 1.00 | 0.00 |
| 2417 | CG2 | THR | 393 | 57.220 | 51.333 | -7.855 | 1.00 | 17.80 |
| 2418 | C | THR | 393 | 58.633 | 54.850 | -8.235 | 1.00 | 22.52 |
| 2419 | O | THR | 393 | 59.201 | 54.661 | -9.303 | 1.00 | 22.98 |
| 2420 | N | LEU | 394 | 58.605 | 56.072 | -7.719 | 1.00 | 19.99 |
| 2421 | H | LEU | 394 | 58.080 | 56.246 | -6.913 | 1.00 | 0.00 |
| 2422 | CA | LEU | 394 | 59.379 | 57.138 | -8.338 | 1.00 | 20.68 |
| 2423 | CB | LEU | 394 | 59.097 | 58.483 | -7.647 | 1.00 | 18.77 |
| 2424 | CG | LEU | 394 | 57.683 | 59.073 | -7.778 | 1.00 | 17.38 |
| 2425 | CD1 | LEU | 394 | 57.642 | 60.395 | -7.031 | 1.00 | 16.87 |
| 2426 | CD2 | LEU | 394 | 57.320 | 59.347 | -9.243 | 1.00 | 17.98 |
| 2427 | C | LEU | 394 | 60.851 | 56.789 | -8.181 | 1.00 | 21.53 |
| 2428 | O | LEU | 394 | 61.273 | 56.518 | -7.073 | 1.00 | 21.60 |
| 2429 | N | THR | 395 | 61.659 | 56.769 | -9.243 | 1.00 | 24.17 |
| 2430 | H | THR | 395 | 61.325 | 56.899 | -10.160 | 1.00 | 0.00 |
| 2431 | CA | THR | 395 | 63.090 | 56.503 | -9.136 | 1.00 | 22.29 |
| 2432 | CB | THR | 395 | 63.474 | 55.581 | -10.303 | 1.00 | 19.28 |
| 2433 | OG1 | THR | 395 | 63.062 | 56.260 | -11.471 | 1.00 | 22.57 |
| 2434 | HG1 | THR | 395 | 63.298 | 55.742 | -12.244 | 1.00 | 0.00 |
| 2435 | CG2 | THR | 395 | 62.748 | 54.238 | -10.343 | 1.00 | 15.70 |

FIG. 5GGGG

| Atom | Atom Type | Residue | # | X | Y | Z | OCC | B |
|---|---|---|---|---|---|---|---|---|
| 2436 | C | THR | 395 | 63.957 | 57.778 | -9.146 | 1.00 | 23.98 |
| 2437 | O | THR | 395 | 65.167 | 57.754 | -8.943 | 1.00 | 25.97 |
| 2438 | N | ARG | 396 | 63.362 | 58.947 | -9.392 | 1.00 | 23.31 |
| 2439 | H | ARG | 396 | 62.385 | 58.998 | -9.428 | 1.00 | 0.00 |
| 2440 | CA | ARG | 396 | 64.097 | 60.187 | -9.519 | 1.00 | 26.02 |
| 2441 | CB | ARG | 396 | 64.189 | 60.695 | -10.936 | 1.00 | 28.35 |
| 2442 | CG | ARG | 396 | 64.986 | 59.799 | -11.825 | 1.00 | 32.64 |
| 2443 | CD | ARG | 396 | 64.666 | 60.158 | -13.248 | 1.00 | 43.18 |
| 2444 | NE | ARG | 396 | 65.266 | 59.145 | -14.075 | 1.00 | 51.29 |
| 2445 | HE | ARG | 396 | 64.830 | 58.271 | -14.157 | 1.00 | 0.00 |
| 2446 | CZ | ARG | 396 | 66.403 | 59.385 | -14.715 | 1.00 | 57.25 |
| 2447 | NH1 | ARG | 396 | 66.982 | 58.338 | -15.382 | 1.00 | 62.75 |
| 2448 | HH11 | ARG | 396 | 66.539 | 57.441 | -15.369 | 1.00 | 0.00 |
| 2449 | HH12 | ARG | 396 | 67.836 | 58.466 | -15.885 | 1.00 | 0.00 |
| 2450 | NH2 | ARG | 396 | 66.961 | 60.635 | -14.722 | 1.00 | 55.06 |
| 2451 | HH21 | ARG | 396 | 66.516 | 61.394 | -14.247 | 1.00 | 0.00 |
| 2452 | HH22 | ARG | 396 | 67.815 | 60.786 | -15.219 | 1.00 | 0.00 |
| 2453 | C | ARG | 396 | 63.286 | 61.210 | -8.805 | 1.00 | 25.66 |
| 2454 | O | ARG | 396 | 62.133 | 60.990 | -8.488 | 1.00 | 25.00 |
| 2455 | N | CYS | 397 | 63.840 | 62.377 | -8.546 | 1.00 | 27.52 |
| 2456 | H | CYS | 397 | 64.766 | 62.545 | -8.830 | 1.00 | 0.00 |
| 2457 | CA | CYS | 397 | 63.114 | 63.404 | -7.849 | 1.00 | 25.75 |
| 2458 | CB | CYS | 397 | 64.086 | 64.447 | -7.306 | 1.00 | 33.69 |
| 2459 | SG | CYS | 397 | 65.267 | 63.936 | -6.027 | 1.00 | 39.19 |
| 2460 | C | CYS | 397 | 62.170 | 64.045 | -8.834 | 1.00 | 24.55 |
| 2461 | O | CYS | 397 | 62.531 | 64.263 | -9.977 | 1.00 | 23.49 |
| 2462 | N | PHE | 398 | 60.945 | 64.386 | -8.464 | 1.00 | 21.44 |
| 2463 | H | PHE | 398 | 60.638 | 64.172 | -7.560 | 1.00 | 0.00 |
| 2464 | CA | PHE | 398 | 60.072 | 65.094 | -9.380 | 1.00 | 20.44 |

FIG. 5HHHH

| Atom | Atom Type | Residue | # | X | Y | Z | OCC | B |
|---|---|---|---|---|---|---|---|---|
| 2634 | OH2 | WAT | 289 | 45.077 | 74.284 | -19.985 | 1.00 | 58.31 |
| 2635 | H1 | WAT | 289 | 44.803 | 75.186 | -19.856 | 1.00 | 0.00 |
| 2636 | H2 | WAT | 289 | 45.225 | 73.984 | -19.086 | 1.00 | 0.00 |
| 2637 | OH2 | WAT | 290 | 36.463 | 68.596 | -18.372 | 1.00 | 41.38 |
| 2638 | H1 | WAT | 290 | 36.206 | 68.878 | -19.244 | 1.00 | 0.00 |
| 2639 | H2 | WAT | 290 | 37.302 | 69.021 | -18.240 | 1.00 | 0.00 |
| 2640 | OH2 | WAT | 291 | 42.509 | 73.175 | -18.360 | 1.00 | 30.40 |
| 2641 | H1 | WAT | 291 | 42.018 | 73.868 | -17.902 | 1.00 | 0.00 |
| 2642 | H2 | WAT | 291 | 41.926 | 72.928 | -19.071 | 1.00 | 0.00 |
| 2643 | OH2 | WAT | 292 | 52.772 | 54.057 | -17.864 | 1.00 | 34.00 |
| 2644 | H1 | WAT | 292 | 52.675 | 54.050 | -16.919 | 1.00 | 0.00 |
| 2645 | H2 | WAT | 292 | 53.709 | 54.139 | -17.997 | 1.00 | 0.00 |
| 2646 | OH2 | WAT | 293 | 58.499 | 51.544 | -17.264 | 1.00 | 39.19 |
| 2647 | H1 | WAT | 293 | 58.896 | 50.712 | -17.042 | 1.00 | 0.00 |
| 2648 | H2 | WAT | 293 | 59.231 | 52.121 | -17.413 | 1.00 | 0.00 |
| 2649 | OH2 | WAT | 294 | 55.293 | 76.832 | -15.365 | 1.00 | 77.96 |
| 2650 | H1 | WAT | 294 | 55.586 | 76.689 | -14.489 | 1.00 | 0.00 |
| 2651 | H2 | WAT | 294 | 55.894 | 76.271 | -15.896 | 1.00 | 0.00 |
| 2652 | OH2 | WAT | 295 | 50.254 | 47.990 | -11.950 | 1.00 | 34.08 |
| 2653 | H1 | WAT | 295 | 49.709 | 48.063 | -12.721 | 1.00 | 0.00 |
| 2654 | H2 | WAT | 295 | 49.755 | 47.316 | -11.486 | 1.00 | 0.00 |
| 2655 | OH2 | WAT | 296 | 37.749 | 48.038 | -8.897 | 1.00 | 50.16 |
| 2656 | H1 | WAT | 296 | 36.805 | 48.072 | -8.734 | 1.00 | 0.00 |
| 2657 | H2 | WAT | 296 | 37.815 | 47.302 | -9.501 | 1.00 | 0.00 |
| 2658 | OH2 | WAT | 297 | 61.144 | 72.978 | -8.832 | 1.00 | 30.80 |
| 2659 | H1 | WAT | 297 | 62.021 | 72.636 | -8.821 | 1.00 | 0.00 |
| 2660 | H2 | WAT | 297 | 61.120 | 73.515 | -8.053 | 1.00 | 0.00 |
| 2661 | OH2 | WAT | 298 | 46.716 | 77.808 | -7.102 | 1.00 | 36.58 |
| 2662 | H1 | WAT | 298 | 47.000 | 78.075 | -6.217 | 1.00 | 0.00 |
| 2663 | H2 | WAT | 298 | 47.380 | 78.176 | -7.649 | 1.00 | 0.00 |
| 2664 | OH2 | WAT | 299 | 43.918 | 76.808 | -6.081 | 1.00 | 35.53 |

FIG. 5IIII

| Atom | Atom Type | Residue | # | X | Y | Z | OCC | B |
|---|---|---|---|---|---|---|---|---|
| 2494 | CD2 | LEU | 400 | 54.550 | 69.476 | -11.022 | 1.00 | 24.92 |
| 2495 | C | LEU | 400 | 58.422 | 71.858 | -11.293 | 1.00 | 36.21 |
| 2496 | O | LEU | 400 | 59.402 | 72.088 | -10.612 | 1.00 | 44.83 |
| 2497 | N | PHE | 401 | 58.287 | 72.708 | -12.295 | 1.00 | 36.07 |
| 2498 | H | PHE | 401 | 57.660 | 72.565 | -13.041 | 1.00 | 0.00 |
| 2499 | CA | PHE | 401 | 59.210 | 73.839 | -12.269 | 1.00 | 33.57 |
| 2500 | CB | PHE | 401 | 60.245 | 73.706 | -13.407 | 1.00 | 32.22 |
| 2501 | CG | PHE | 401 | 61.399 | 72.857 | -12.928 | 1.00 | 33.80 |
| 2502 | CD1 | PHE | 401 | 61.474 | 71.519 | -13.260 | 1.00 | 32.31 |
| 2503 | CD2 | PHE | 401 | 62.416 | 73.423 | -12.173 | 1.00 | 39.98 |
| 2504 | CE1 | PHE | 401 | 62.582 | 70.764 | -12.892 | 1.00 | 33.77 |
| 2505 | CE2 | PHE | 401 | 63.512 | 72.653 | -11.790 | 1.00 | 40.60 |
| 2506 | CZ | PHE | 401 | 63.611 | 71.326 | -12.167 | 1.00 | 36.46 |
| 2507 | C | PHE | 401 | 58.367 | 75.031 | -12.475 | 1.00 | 32.19 |
| 2508 | O | PHE | 401 | 58.334 | 75.584 | -13.558 | 1.00 | 29.45 |
| 2509 | N | PRO | 402 | 57.638 | 75.512 | -11.527 | 1.00 | 29.88 |
| 2510 | CD | PRO | 402 | 57.751 | 75.159 | -10.125 | 1.00 | 27.11 |
| 2511 | CA | PRO | 402 | 56.710 | 76.609 | -11.755 | 1.00 | 31.83 |
| 2512 | CB | PRO | 402 | 56.137 | 76.946 | -10.380 | 1.00 | 27.59 |
| 2513 | CG | PRO | 402 | 57.161 | 76.376 | -9.428 | 1.00 | 24.71 |
| 2514 | C | PRO | 402 | 57.461 | 77.757 | -12.427 | 1.00 | 37.62 |
| 2515 | O | PRO | 402 | 58.588 | 78.123 | -12.070 | 1.00 | 38.17 |
| 2516 | N | GLY | 403 | 56.770 | 78.302 | -13.431 | 1.00 | 37.83 |
| 2517 | H | GLY | 403 | 55.816 | 78.096 | -13.558 | 1.00 | 0.00 |
| 2518 | CA | GLY | 403 | 57.339 | 79.300 | -14.327 | 1.00 | 40.55 |
| 2519 | C | GLY | 403 | 58.024 | 78.691 | -15.553 | 1.00 | 39.74 |
| 2520 | O | GLY | 403 | 58.363 | 79.436 | -16.458 | 1.00 | 40.77 |
| 2521 | N | HIS | 404 | 58.258 | 77.372 | -15.646 | 1.00 | 40.90 |
| 2522 | H | HIS | 404 | 57.856 | 76.702 | -15.043 | 1.00 | 0.00 |

FIG. 5JJJJ

| Atom | Atom Type | Residue | # | X | Y | Z | OCC | B |
|---|---|---|---|---|---|---|---|---|
| 2523 | CA | HIS | 404 | 59.038 | 76.818 | -16.735 | 1.00 | 41.51 |
| 2524 | CB | HIS | 404 | 60.391 | 76.313 | -16.275 | 1.00 | 43.86 |
| 2525 | CG | HIS | 404 | 61.057 | 77.377 | -15.470 | 1.00 | 47.48 |
| 2526 | CD2 | HIS | 404 | 62.077 | 78.167 | -15.913 | 1.00 | 46.94 |
| 2527 | ND1 | HIS | 404 | 60.694 | 77.798 | -14.262 | 1.00 | 50.29 |
| 2528 | HD1 | HIS | 404 | 59.973 | 77.436 | -13.710 | 1.00 | 0.00 |
| 2529 | CE1 | HIS | 404 | 61.438 | 78.828 | -13.970 | 1.00 | 47.33 |
| 2530 | NE2 | HIS | 404 | 62.266 | 79.045 | -14.963 | 1.00 | 49.11 |
| 2531 | HE2 | HIS | 404 | 62.923 | 79.771 | -14.979 | 1.00 | 0.00 |
| 2532 | C | HIS | 404 | 58.318 | 75.633 | -17.302 | 1.00 | 41.65 |
| 2533 | O | HIS | 404 | 58.804 | 75.085 | -18.288 | 1.00 | 44.03 |
| 2534 | OT | HIS | 404 | 57.304 | 75.238 | -16.718 | 1.00 | 41.54 |
| 2535 | OH2 | WAT | 256 | 57.131 | 53.937 | -16.157 | 1.00 | 21.86 |
| 2536 | H1 | WAT | 256 | 57.956 | 53.989 | -16.611 | 1.00 | 0.00 |
| 2537 | H2 | WAT | 256 | 56.715 | 53.157 | -16.559 | 1.00 | 0.00 |
| 2538 | OH2 | WAT | 257 | 59.288 | 45.222 | -12.720 | 1.00 | 24.45 |
| 2539 | H1 | WAT | 257 | 59.678 | 44.463 | -12.289 | 1.00 | 0.00 |
| 2540 | H2 | WAT | 257 | 59.326 | 45.020 | -13.638 | 1.00 | 0.00 |
| 2541 | OH2 | WAT | 258 | 61.365 | 66.988 | -12.454 | 1.00 | 18.38 |
| 2542 | H1 | WAT | 258 | 61.282 | 66.754 | -11.566 | 1.00 | 0.00 |
| 2543 | H2 | WAT | 258 | 61.920 | 66.336 | -12.878 | 1.00 | 0.00 |
| 2544 | OH2 | WAT | 259 | 54.401 | 52.311 | -15.488 | 1.00 | 26.12 |
| 2545 | H1 | WAT | 259 | 53.455 | 52.320 | -15.423 | 1.00 | 0.00 |
| 2546 | H2 | WAT | 259 | 54.685 | 52.959 | -14.831 | 1.00 | 0.00 |
| 2547 | OH2 | WAT | 260 | 52.948 | 45.165 | -10.748 | 1.00 | 22.53 |
| 2548 | H1 | WAT | 260 | 53.471 | 44.927 | -9.991 | 1.00 | 0.00 |
| 2549 | H2 | WAT | 260 | 52.622 | 46.039 | -10.552 | 1.00 | 0.00 |
| 2550 | OH2 | WAT | 261 | 39.932 | 72.422 | -0.681 | 1.00 | 41.66 |
| 2551 | H1 | WAT | 261 | 40.131 | 72.039 | 0.168 | 1.00 | 0.00 |

FIG. 5KKKK

| Atom | Atom Type | Residue | # | X | Y | Z | OCC | B |
|---|---|---|---|---|---|---|---|---|
| 2552 | H2 | WAT | 261 | 39.184 | 71.954 | -1.011 | 1.00 | 0.00 |
| 2553 | OH2 | WAT | 262 | 40.595 | 65.620 | 4.462 | 1.00 | 27.37 |
| 2554 | H1 | WAT | 262 | 40.213 | 65.976 | 5.270 | 1.00 | 0.00 |
| 2555 | H2 | WAT | 262 | 39.866 | 65.614 | 3.842 | 1.00 | 0.00 |
| 2556 | OH2 | WAT | 263 | 59.703 | 63.723 | -5.839 | 1.00 | 23.97 |
| 2557 | H1 | WAT | 263 | 59.734 | 63.118 | -5.108 | 1.00 | 0.00 |
| 2558 | H2 | WAT | 263 | 59.203 | 63.239 | -6.512 | 1.00 | 0.00 |
| 2559 | OH2 | WAT | 264 | 57.975 | 70.486 | -7.257 | 1.00 | 26.26 |
| 2560 | H1 | WAT | 264 | 57.886 | 69.546 | -7.232 | 1.00 | 0.00 |
| 2561 | H2 | WAT | 264 | 58.580 | 70.685 | -6.537 | 1.00 | 0.00 |
| 2562 | OH2 | WAT | 265 | 49.889 | 74.051 | 7.407 | 1.00 | 51.01 |
| 2563 | H1 | WAT | 265 | 49.381 | 73.658 | 6.713 | 1.00 | 0.00 |
| 2564 | H2 | WAT | 265 | 49.717 | 74.986 | 7.331 | 1.00 | 0.00 |
| 2565 | OH2 | WAT | 266 | 55.224 | 73.467 | -12.629 | 1.00 | 54.87 |
| 2566 | H1 | WAT | 266 | 56.050 | 73.568 | -12.183 | 1.00 | 0.00 |
| 2567 | H2 | WAT | 266 | 55.324 | 73.889 | -13.488 | 1.00 | 0.00 |
| 2568 | OH2 | WAT | 267 | 57.220 | 72.666 | -15.238 | 1.00 | 33.22 |
| 2569 | H1 | WAT | 267 | 57.189 | 73.255 | -16.021 | 1.00 | 0.00 |
| 2570 | H2 | WAT | 267 | 56.964 | 71.837 | -15.606 | 1.00 | 0.00 |
| 2571 | OH2 | WAT | 268 | 35.858 | 66.670 | -2.607 | 1.00 | 29.58 |
| 2572 | H1 | WAT | 268 | 36.152 | 66.629 | -1.699 | 1.00 | 0.00 |
| 2573 | H2 | WAT | 268 | 35.860 | 67.587 | -2.844 | 1.00 | 0.00 |
| 2574 | OH2 | WAT | 269 | 48.789 | 71.281 | -21.710 | 1.00 | 49.48 |
| 2575 | H1 | WAT | 269 | 47.897 | 71.644 | -21.837 | 1.00 | 0.00 |
| 2576 | H2 | WAT | 269 | 49.355 | 71.928 | -22.109 | 1.00 | 0.00 |
| 2577 | OH2 | WAT | 270 | 59.440 | 63.444 | -17.067 | 1.00 | 23.58 |
| 2578 | H1 | WAT | 270 | 59.959 | 62.711 | -16.814 | 1.00 | 0.00 |
| 2579 | H2 | WAT | 270 | 58.513 | 63.193 | -17.097 | 1.00 | 0.00 |
| 2580 | OH2 | WAT | 271 | 48.923 | 44.941 | -15.001 | 1.00 | 59.67 |

FIG. 5LLLL

| Atom | Atom Type | Residue | # | X | Y | Z | OCC | B |
|---|---|---|---|---|---|---|---|---|
| 2581 | H1 | WAT | 271 | 48.905 | 44.016 | -14.762 | 1.00 | 0.00 |
| 2582 | H2 | WAT | 271 | 49.386 | 44.932 | -15.826 | 1.00 | 0.00 |
| 2583 | OH2 | WAT | 272 | 44.435 | 59.093 | 9.639 | 1.00 | 24.08 |
| 2584 | H1 | WAT | 272 | 44.989 | 59.185 | 8.877 | 1.00 | 0.00 |
| 2585 | H2 | WAT | 272 | 44.990 | 58.678 | 10.300 | 1.00 | 0.00 |
| 2586 | OH2 | WAT | 273 | 53.920 | 52.043 | -8.038 | 1.00 | 23.85 |
| 2587 | H1 | WAT | 273 | 54.603 | 52.710 | -8.021 | 1.00 | 0.00 |
| 2588 | H2 | WAT | 273 | 54.232 | 51.362 | -8.608 | 1.00 | 0.00 |
| 2589 | OH2 | WAT | 274 | 62.871 | 68.183 | -1.698 | 1.00 | 38.92 |
| 2590 | H1 | WAT | 274 | 62.632 | 67.292 | -1.909 | 1.00 | 0.00 |
| 2591 | H2 | WAT | 274 | 63.467 | 68.466 | -2.393 | 1.00 | 0.00 |
| 2592 | OH2 | WAT | 275 | 46.942 | 70.044 | -23.874 | 1.00 | 49.11 |
| 2593 | H1 | WAT | 275 | 47.058 | 69.784 | -24.775 | 1.00 | 0.00 |
| 2594 | H2 | WAT | 275 | 47.406 | 69.414 | -23.326 | 1.00 | 0.00 |
| 2595 | OH2 | WAT | 276 | 50.771 | 63.408 | 17.889 | 1.00 | 54.39 |
| 2596 | H1 | WAT | 276 | 50.872 | 64.350 | 17.946 | 1.00 | 0.00 |
| 2597 | H2 | WAT | 276 | 50.541 | 63.304 | 16.967 | 1.00 | 0.00 |
| 2598 | OH2 | WAT | 277 | 45.555 | 65.749 | 12.972 | 1.00 | 27.42 |
| 2599 | H1 | WAT | 277 | 46.291 | 65.423 | 12.436 | 1.00 | 0.00 |
| 2600 | H2 | WAT | 277 | 44.772 | 65.498 | 12.518 | 1.00 | 0.00 |
| 2601 | OH2 | WAT | 278 | 57.066 | 46.788 | -11.771 | 1.00 | 27.22 |
| 2602 | H1 | WAT | 278 | 56.509 | 46.154 | -12.204 | 1.00 | 0.00 |
| 2603 | H2 | WAT | 278 | 56.806 | 47.667 | -12.005 | 1.00 | 0.00 |
| 2604 | OH2 | WAT | 279 | 50.499 | 65.012 | -29.411 | 1.00 | 47.42 |
| 2605 | H1 | WAT | 279 | 50.711 | 64.860 | -28.494 | 1.00 | 0.00 |
| 2606 | H2 | WAT | 279 | 51.009 | 65.791 | -29.571 | 1.00 | 0.00 |
| 2607 | OH2 | WAT | 280 | 42.398 | 64.363 | -27.639 | 1.00 | 73.43 |
| 2608 | H1 | WAT | 280 | 41.614 | 64.685 | -28.072 | 1.00 | 0.00 |
| 2609 | H2 | WAT | 280 | 42.691 | 65.121 | -27.145 | 1.00 | 0.00 |

FIG. 5MMMM

| Atom | Atom Type | Residue | # | X | Y | Z | OCC | B |
|---|---|---|---|---|---|---|---|---|
| 2610 | OH2 | WAT | 281 | 47.580 | 50.658 | -26.241 | 1.00 | 45.60 |
| 2611 | H1 | WAT | 281 | 47.146 | 51.280 | -26.806 | 1.00 | 0.00 |
| 2612 | H2 | WAT | 281 | 48.027 | 50.065 | -26.836 | 1.00 | 0.00 |
| 2613 | OH2 | WAT | 282 | 40.354 | 58.806 | -25.242 | 1.00 | 51.46 |
| 2614 | H1 | WAT | 282 | 39.834 | 59.191 | -25.936 | 1.00 | 0.00 |
| 2615 | H2 | WAT | 282 | 41.237 | 58.816 | -25.588 | 1.00 | 0.00 |
| 2616 | OH2 | WAT | 283 | 59.582 | 57.507 | -22.297 | 1.00 | 50.06 |
| 2617 | H1 | WAT | 283 | 59.205 | 58.060 | -22.973 | 1.00 | 0.00 |
| 2618 | H2 | WAT | 283 | 60.461 | 57.302 | -22.574 | 1.00 | 0.00 |
| 2619 | OH2 | WAT | 284 | 62.787 | 66.431 | -21.929 | 1.00 | 64.67 |
| 2620 | H1 | WAT | 284 | 62.786 | 67.378 | -21.776 | 1.00 | 0.00 |
| 2621 | H2 | WAT | 284 | 63.310 | 66.298 | -22.709 | 1.00 | 0.00 |
| 2622 | OH2 | WAT | 285 | 42.178 | 68.676 | -21.635 | 1.00 | 47.92 |
| 2623 | H1 | WAT | 285 | 42.226 | 68.152 | -20.834 | 1.00 | 0.00 |
| 2624 | H2 | WAT | 285 | 41.528 | 68.220 | -22.154 | 1.00 | 0.00 |
| 2625 | OH2 | WAT | 286 | 59.860 | 64.459 | -20.626 | 1.00 | 45.90 |
| 2626 | H1 | WAT | 286 | 59.529 | 63.613 | -20.882 | 1.00 | 0.00 |
| 2627 | H2 | WAT | 286 | 60.034 | 64.935 | -21.429 | 1.00 | 0.00 |
| 2628 | OH2 | WAT | 287 | 38.592 | 60.429 | -19.380 | 1.00 | 45.23 |
| 2629 | H1 | WAT | 287 | 37.765 | 59.995 | -19.240 | 1.00 | 0.00 |
| 2630 | H2 | WAT | 287 | 38.339 | 61.266 | -19.751 | 1.00 | 0.00 |
| 2631 | OH2 | WAT | 288 | 49.737 | 64.079 | -19.712 | 1.00 | 31.09 |
| 2632 | H1 | WAT | 288 | 49.889 | 64.551 | -20.540 | 1.00 | 0.00 |
| 2633 | H2 | WAT | 288 | 48.791 | 63.991 | -19.646 | 1.00 | 0.00 |
| 2634 | OH2 | WAT | 289 | 45.077 | 74.284 | -19.985 | 1.00 | 58.31 |
| 2635 | H1 | WAT | 289 | 44.803 | 75.186 | -19.856 | 1.00 | 0.00 |
| 2636 | H2 | WAT | 289 | 45.225 | 73.984 | -19.086 | 1.00 | 0.00 |
| 2637 | OH2 | WAT | 290 | 36.463 | 68.596 | -18.372 | 1.00 | 41.38 |
| 2638 | H1 | WAT | 290 | 36.206 | 68.878 | -19.244 | 1.00 | 0.00 |

FIG. 5NNNN

| Atom | Atom Type | Residue | # | X | Y | Z | OCC | B |
|---|---|---|---|---|---|---|---|---|
| 2639 | H2 | WAT | 290 | 37.302 | 69.021 | -18.240 | 1.00 | 0.00 |
| 2640 | OH2 | WAT | 291 | 42.509 | 73.175 | -18.360 | 1.00 | 30.40 |
| 2641 | H1 | WAT | 291 | 42.018 | 73.868 | -17.902 | 1.00 | 0.00 |
| 2642 | H2 | WAT | 291 | 41.926 | 72.928 | -19.071 | 1.00 | 0.00 |
| 2643 | OH2 | WAT | 292 | 52.772 | 54.057 | -17.864 | 1.00 | 34.00 |
| 2644 | H1 | WAT | 292 | 52.675 | 54.050 | -16.919 | 1.00 | 0.00 |
| 2645 | H2 | WAT | 292 | 53.709 | 54.139 | -17.997 | 1.00 | 0.00 |
| 2646 | OH2 | WAT | 293 | 58.499 | 51.544 | -17.264 | 1.00 | 39.19 |
| 2647 | H1 | WAT | 293 | 58.896 | 50.712 | -17.042 | 1.00 | 0.00 |
| 2648 | H2 | WAT | 293 | 59.231 | 52.121 | -17.413 | 1.00 | 0.00 |
| 2649 | OH2 | WAT | 294 | 55.293 | 76.832 | -15.365 | 1.00 | 77.96 |
| 2650 | H1 | WAT | 294 | 55.586 | 76.689 | -14.489 | 1.00 | 0.00 |
| 2651 | H2 | WAT | 294 | 55.894 | 76.271 | -15.896 | 1.00 | 0.00 |
| 2652 | OH2 | WAT | 295 | 50.254 | 47.990 | -11.950 | 1.00 | 34.08 |
| 2653 | H1 | WAT | 295 | 49.709 | 48.063 | -12.721 | 1.00 | 0.00 |
| 2654 | H2 | WAT | 295 | 49.755 | 47.316 | -11.486 | 1.00 | 0.00 |
| 2655 | OH2 | WAT | 296 | 37.749 | 48.038 | -8.897 | 1.00 | 50.16 |
| 2656 | H1 | WAT | 296 | 36.805 | 48.072 | -8.734 | 1.00 | 0.00 |
| 2657 | H2 | WAT | 296 | 37.815 | 47.302 | -9.501 | 1.00 | 0.00 |
| 2658 | OH2 | WAT | 297 | 61.144 | 72.978 | -8.832 | 1.00 | 30.80 |
| 2659 | H1 | WAT | 297 | 62.021 | 72.636 | -8.821 | 1.00 | 0.00 |
| 2660 | H2 | WAT | 297 | 61.120 | 73.515 | -8.053 | 1.00 | 0.00 |
| 2661 | OH2 | WAT | 298 | 46.716 | 77.808 | -7.102 | 1.00 | 36.58 |
| 2662 | H1 | WAT | 298 | 47.000 | 78.075 | -6.217 | 1.00 | 0.00 |
| 2663 | H2 | WAT | 298 | 47.380 | 78.176 | -7.649 | 1.00 | 0.00 |
| 2664 | OH2 | WAT | 299 | 43.918 | 76.808 | -6.081 | 1.00 | 35.53 |
| 2665 | H1 | WAT | 299 | 43.850 | 77.750 | -6.052 | 1.00 | 0.00 |
| 2666 | H2 | WAT | 299 | 44.809 | 76.650 | -5.782 | 1.00 | 0.00 |
| 2667 | OH2 | WAT | 300 | 60.882 | 61.010 | -5.837 | 1.00 | 32.21 |

FIG. 50000

| Atom | Atom Type | Residue | # | X | Y | Z | OCC | B |
|---|---|---|---|---|---|---|---|---|
| 2668 | H1 | WAT | 300 | 60.547 | 60.543 | -5.092 | 1.00 | 0.00 |
| 2669 | H2 | WAT | 300 | 60.943 | 61.933 | -5.683 | 1.00 | 0.00 |
| 2670 | OH2 | WAT | 301 | 56.234 | 77.147 | -5.325 | 1.00 | 45.88 |
| 2671 | H1 | WAT | 301 | 55.449 | 77.454 | -4.859 | 1.00 | 0.00 |
| 2672 | H2 | WAT | 301 | 56.348 | 77.843 | -5.971 | 1.00 | 0.00 |
| 2673 | OH2 | WAT | 302 | 43.603 | 47.976 | -4.116 | 1.00 | 46.63 |
| 2674 | H1 | WAT | 302 | 43.969 | 48.651 | -4.654 | 1.00 | 0.00 |
| 2675 | H2 | WAT | 302 | 43.745 | 47.160 | -4.601 | 1.00 | 0.00 |
| 2676 | OH2 | WAT | 303 | 41.712 | 55.660 | -0.536 | 1.00 | 36.50 |
| 2677 | H1 | WAT | 303 | 41.333 | 54.851 | -0.150 | 1.00 | 0.00 |
| 2678 | H2 | WAT | 303 | 42.325 | 55.359 | -1.193 | 1.00 | 0.00 |
| 2679 | OH2 | WAT | 304 | 51.729 | 51.156 | -0.590 | 1.00 | 72.02 |
| 2680 | H1 | WAT | 304 | 52.459 | 50.567 | -0.423 | 1.00 | 0.00 |
| 2681 | H2 | WAT | 304 | 51.363 | 51.290 | 0.284 | 1.00 | 0.00 |
| 2682 | OH2 | WAT | 305 | 44.576 | 76.180 | 0.284 | 1.00 | 70.30 |
| 2683 | H1 | WAT | 305 | 44.696 | 75.258 | 0.070 | 1.00 | 0.00 |
| 2684 | H2 | WAT | 305 | 44.178 | 76.553 | -0.493 | 1.00 | 0.00 |
| 2685 | OH2 | WAT | 306 | 38.913 | 54.669 | 0.203 | 1.00 | 39.19 |
| 2686 | H1 | WAT | 306 | 39.203 | 55.452 | -0.255 | 1.00 | 0.00 |
| 2687 | H2 | WAT | 306 | 38.207 | 54.284 | -0.306 | 1.00 | 0.00 |
| 2688 | OH2 | WAT | 307 | 42.134 | 58.338 | 1.150 | 1.00 | 29.79 |
| 2689 | H1 | WAT | 307 | 41.312 | 57.982 | 1.511 | 1.00 | 0.00 |
| 2690 | H2 | WAT | 307 | 42.564 | 57.551 | 0.838 | 1.00 | 0.00 |
| 2691 | OH2 | WAT | 308 | 56.648 | 60.941 | 0.737 | 1.00 | 38.97 |
| 2692 | H1 | WAT | 308 | 55.700 | 60.977 | 0.666 | 1.00 | 0.00 |
| 2693 | H2 | WAT | 308 | 56.928 | 61.839 | 0.583 | 1.00 | 0.00 |
| 2694 | OH2 | WAT | 309 | 45.030 | 48.554 | 9.192 | 1.00 | 48.96 |
| 2695 | H1 | WAT | 309 | 44.943 | 47.651 | 9.474 | 1.00 | 0.00 |
| 2696 | H2 | WAT | 309 | 45.909 | 48.606 | 8.834 | 1.00 | 0.00 |

FIG. 5PPPP

| Atom | Atom Type | Residue | # | X | Y | Z | OCC | B |
|---|---|---|---|---|---|---|---|---|
| 2697 | OH2 | WAT | 310 | 41.590 | 59.650 | 10.888 | 1.00 | 32.65 |
| 2698 | H1 | WAT | 310 | 41.965 | 59.981 | 11.702 | 1.00 | 0.00 |
| 2699 | H2 | WAT | 310 | 41.171 | 60.430 | 10.534 | 1.00 | 0.00 |
| 2700 | OH2 | WAT | 311 | 30.678 | 62.812 | 10.599 | 1.00 | 48.30 |
| 2701 | H1 | WAT | 311 | 31.519 | 63.059 | 10.280 | 1.00 | 0.00 |
| 2702 | H2 | WAT | 311 | 30.787 | 61.904 | 10.876 | 1.00 | 0.00 |
| 2703 | OH2 | WAT | 312 | 44.035 | 51.425 | 12.296 | 1.00 | 49.62 |
| 2704 | H1 | WAT | 312 | 43.759 | 51.313 | 11.383 | 1.00 | 0.00 |
| 2705 | H2 | WAT | 312 | 43.889 | 50.557 | 12.653 | 1.00 | 0.00 |
| 2706 | OH2 | WAT | 313 | 53.084 | 69.483 | 13.408 | 1.00 | 45.11 |
| 2707 | H1 | WAT | 313 | 53.666 | 68.732 | 13.409 | 1.00 | 0.00 |
| 2708 | H2 | WAT | 313 | 52.885 | 69.526 | 12.474 | 1.00 | 0.00 |
| 2709 | OH2 | WAT | 314 | 33.280 | 54.578 | 14.147 | 1.00 | 71.20 |
| 2710 | H1 | WAT | 314 | 32.487 | 54.073 | 14.271 | 1.00 | 0.00 |
| 2711 | H2 | WAT | 314 | 33.372 | 54.689 | 13.208 | 1.00 | 0.00 |
| 2712 | OH2 | WAT | 315 | 60.509 | 60.787 | -18.332 | 1.00 | 30.28 |
| 2713 | H1 | WAT | 315 | 60.849 | 61.538 | -18.810 | 1.00 | 0.00 |
| 2714 | H2 | WAT | 315 | 60.079 | 61.112 | -17.565 | 1.00 | 0.00 |
| 2715 | OH2 | WAT | 316 | 36.436 | 51.291 | 10.254 | 1.00 | 49.82 |
| 2716 | H1 | WAT | 316 | 36.114 | 50.786 | 9.515 | 1.00 | 0.00 |
| 2717 | H2 | WAT | 316 | 35.650 | 51.562 | 10.727 | 1.00 | 0.00 |
| 2718 | OH2 | WAT | 317 | 47.543 | 66.402 | -29.189 | 1.00 | 49.95 |
| 2719 | H1 | WAT | 317 | 46.808 | 66.985 | -29.300 | 1.00 | 0.00 |
| 2720 | H2 | WAT | 317 | 48.149 | 66.611 | -29.900 | 1.00 | 0.00 |
| 2721 | OH2 | WAT | 318 | 39.908 | 61.653 | -21.569 | 1.00 | 55.32 |
| 2722 | H1 | WAT | 318 | 39.811 | 62.356 | -20.946 | 1.00 | 0.00 |
| 2723 | H2 | WAT | 318 | 40.435 | 61.009 | -21.097 | 1.00 | 0.00 |
| 2724 | OH2 | WAT | 319 | 43.648 | 51.317 | -20.053 | 1.00 | 55.22 |
| 2725 | H1 | WAT | 319 | 44.217 | 51.632 | -19.345 | 1.00 | 0.00 |

FIG. 5QQQQ

| Atom | Atom Type | Residue | # | X | Y | Z | OCC | B |
|---|---|---|---|---|---|---|---|---|
| 2726 | H2 | WAT | 319 | 42.798 | 51.245 | -19.643 | 1.00 | 0.00 |
| 2727 | OH2 | WAT | 320 | 42.904 | 66.185 | -19.404 | 1.00 | 43.44 |
| 2728 | H1 | WAT | 320 | 43.844 | 66.182 | -19.470 | 1.00 | 0.00 |
| 2729 | H2 | WAT | 320 | 42.797 | 66.244 | -18.456 | 1.00 | 0.00 |
| 2730 | OH2 | WAT | 321 | 52.576 | 73.792 | -19.312 | 1.00 | 47.88 |
| 2731 | H1 | WAT | 321 | 52.248 | 73.438 | -18.497 | 1.00 | 0.00 |
| 2732 | H2 | WAT | 321 | 51.924 | 73.486 | -19.932 | 1.00 | 0.00 |
| 2733 | OH2 | WAT | 322 | 61.556 | 50.185 | -16.806 | 1.00 | 60.71 |
| 2734 | H1 | WAT | 322 | 60.747 | 49.697 | -16.824 | 1.00 | 0.00 |
| 2735 | H2 | WAT | 322 | 62.307 | 49.596 | -16.932 | 1.00 | 0.00 |
| 2736 | OH2 | WAT | 323 | 24.851 | 56.075 | -3.153 | 1.00 | 38.05 |
| 2737 | H1 | WAT | 323 | 25.114 | 55.419 | -2.507 | 1.00 | 0.00 |
| 2738 | H2 | WAT | 323 | 25.365 | 55.812 | -3.916 | 1.00 | 0.00 |
| 2739 | OH2 | WAT | 324 | 30.036 | 71.409 | -2.744 | 1.00 | 45.31 |
| 2740 | H1 | WAT | 324 | 29.383 | 70.770 | -3.022 | 1.00 | 0.00 |
| 2741 | H2 | WAT | 324 | 29.785 | 71.599 | -1.852 | 1.00 | 0.00 |
| 2742 | OH2 | WAT | 325 | 33.127 | 79.276 | 0.558 | 1.00 | 57.23 |
| 2743 | H1 | WAT | 325 | 33.528 | 79.402 | -0.294 | 1.00 | 0.00 |
| 2744 | H2 | WAT | 325 | 32.600 | 80.047 | 0.708 | 1.00 | 0.00 |
| 2745 | OH2 | WAT | 326 | 35.907 | 47.459 | 2.721 | 1.00 | 52.14 |
| 2746 | H1 | WAT | 326 | 35.224 | 48.120 | 2.665 | 1.00 | 0.00 |
| 2747 | H2 | WAT | 326 | 36.753 | 47.864 | 2.620 | 1.00 | 0.00 |
| 2748 | OH2 | WAT | 327 | 54.215 | 72.016 | 6.546 | 1.00 | 52.02 |
| 2749 | H1 | WAT | 327 | 55.027 | 71.530 | 6.405 | 1.00 | 0.00 |
| 2750 | H2 | WAT | 327 | 54.516 | 72.859 | 6.883 | 1.00 | 0.00 |
| 2751 | OH2 | WAT | 328 | 41.269 | 52.487 | 1.122 | 1.00 | 51.87 |
| 2752 | H1 | WAT | 328 | 40.694 | 51.781 | 1.440 | 1.00 | 0.00 |
| 2753 | H2 | WAT | 328 | 42.127 | 52.127 | 1.259 | 1.00 | 0.00 |
| 2754 | OH2 | WAT | 329 | 34.066 | 58.806 | 13.164 | 1.00 | 55.71 |

FIG. 5RRRR

| Atom | Atom Type | Residue | # | X | Y | Z | OCC | B |
|---|---|---|---|---|---|---|---|---|
| 2755 | H1 | WAT | 329 | 34.724 | 59.474 | 13.292 | 1.00 | 0.00 |
| 2756 | H2 | WAT | 329 | 34.564 | 58.010 | 12.945 | 1.00 | 0.00 |
| 2757 | OH2 | WAT | 330 | 41.816 | 52.756 | 13.918 | 1.00 | 44.03 |
| 2758 | H1 | WAT | 330 | 42.281 | 53.408 | 13.395 | 1.00 | 0.00 |
| 2759 | H2 | WAT | 330 | 42.525 | 52.335 | 14.395 | 1.00 | 0.00 |
| 2760 | OH2 | WAT | 331 | 39.370 | 62.098 | 14.302 | 1.00 | 54.70 |
| 2761 | H1 | WAT | 331 | 38.736 | 62.661 | 14.727 | 1.00 | 0.00 |
| 2762 | H2 | WAT | 331 | 39.761 | 62.569 | 13.574 | 1.00 | 0.00 |
| 2763 | OH2 | WAT | 332 | 50.309 | 69.365 | 13.364 | 1.00 | 54.23 |
| 2764 | H1 | WAT | 332 | 50.055 | 69.719 | 12.508 | 1.00 | 0.00 |
| 2765 | H2 | WAT | 332 | 51.043 | 69.910 | 13.645 | 1.00 | 0.00 |
| 2766 | OH2 | WAT | 333 | 40.562 | 55.451 | 15.773 | 1.00 | 61.39 |
| 2767 | H1 | WAT | 333 | 39.723 | 55.080 | 16.041 | 1.00 | 0.00 |
| 2768 | H2 | WAT | 333 | 40.748 | 55.017 | 14.937 | 1.00 | 0.00 |

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 404 amino acids
       (B) TYPE: amino acid
       (D) TOPOLOGY: linear (ii) MOLECULE TYPE: protein (iii) HYPOTHETICAL: NO (xi) SEQUENCE DESCRIPTION: SEQ ID NO:1:

```
Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320
```

-continued

```
Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His
```

CRYSTAL STRUCTURE AND MUTANTS OF INTERLEUKIN-1β CONVERTING ENZYME

This is a division, of application Ser. No. 08/261.582, filed Jun. 17, 1994, now abandoned entitled Crystal Structure and Mutants of Interleukin-1β Converting Enzyme.

TECHNICAL FIELD OF INVENTION

The present invention relates to crystals of interleukin-1β converting enzyme ("ICE") and more particularly to the high resolution structure of ICE obtained by X-ray diffraction. This invention also relates to mutants of ICE. In addition, this invention relates to methods of using the structure coordinates of ICE and mutants thereof to screen and design compounds that bind to the active site and accessory binding site of ICE.

BACKGROUND ART

Interleukin-1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45–56 (1986). As such, it is involved in the pathogenesis of chronic and acute inflammatory and autoimmune diseases. IL-1 is predominantly produced by peripheral blood monocytes and exists in two distinct agonist forms, IL-1α and IL-1β. Mosely, B. S. et al., *Proc. Nat. Acad. Sci.*, 84, pp. 4572–4576 (1987); Lonnemann G. et al., *Eur.J. Immunol.*, 19, pp. 1531–1536 (1989).

IL-1β is synthesized as a biologically inactive precursor, pIL-1β. pIL-1β is a 33 kDa polypeptide that lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp 116 and Ala 117 to produce the biologically active C-terminal fragment of 17 kDa molecular weight found in serum and synovial fluid. Sleath, P. R. et al., *J. Biol. Chem.*, 265, pp. 14526–14528 (1992); Howard, A. D. et al., *J. Immunol.*, 147, pp. 2964–2969 (1991). Processing by ICE is also necessary for the transport of mature IL-1β through the cell membrane.

ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. USA*, 86, pp. 5227–5231 (1989). ICE, or its homologues, also appears to be involved in the regulation of cell death or apoptosis. Yuan, J. et al., *Cell*, 75, pp. 641–652 (1993); Miura, M. et al., *Cell*, 75, pp. 653–660 (1993); Nett-Fiordalisi, M. A. et al., *J. Cell Biochem.*, 17B, p. 117 (1993). In particular, ICE or ICE homologues are thought to be associated with the regulation of apoptosis in neurogenerative diseases, such as Alzheimer's and Parkinson's disease. Marx, J. and M. Baringa, *Science*, 259, pp. 760–762 (1993); Gagliardini, V. et al., *Science*, 263, pp. 826–828 (1994).

ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768–774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., *Ann. N.Y. Acad. Sci.*, 696, pp. 133–148 (1993); Molineaux, S. M. et al., *Proc. Nat. Acad. Sci.*, 90, pp. 1809–1813 (1993). Knowledge of the primary structure of ICE, however, does not allow prediction of its tertiary structure. Nor does it afford an understanding of the structural, conformational and chemical interactions of ICE and its substrate pIL-1β or other substrates or inhibitors.

ICE inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. However, due to their peptidic nature, such inhibitors are typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. This has hampered their development into effective drugs.

SUMMARY OF THE INVENTION

The present invention solves the above problems.

It is an object of this invention to solve the three-dimensional structure of interleukin-1β converting enzyme ("ICE") and to determine its structure coordinates.

It is an object of this invention to use the structure coordinates of an ICE crystal to reveal the atomic details of the active site and one or more accessory binding sites of the enzyme.

It is also an object of this invention to use the structure coordinates of an ICE crystal to solve the structure of a different ICE crystal, or a crystal of a mutant, homologue or co-complex, of ICE.

It is a further object of this invention to provide interleukin-1β converting enzyme mutants characterized by one or more different properties as compared with wild-type ICE. These properties include altered surface charge, increased stability to subunit dissociation, altered substrate specificity or higher specific activity. ICE mutants are useful to identify those amino acids that are most important for the enzymatic activity of ICE. This information, in turn, allows the design of improved inhibitors of ICE as compared with peptidic ICE inhibitors.

It is also an object of this invention to use the structure coordinates and atomic details of ICE, or its mutants or homologues or co-complexes, to design, evaluate computationally, synthesize and use inhibitors of ICE that avoid the undesirable physical and pharmacologic properties of peptidic ICE inhibitors.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1A and 1B represent ribbon drawings of the p20/p10 interleukin-1β converting enzyme heterodimer. The active site is at the top of the figure, roughly at the center of the cluster of displayed side chains.

FIGS. 4A and 4B lists the amino acids of ICE that constitute the tetramer interface contacts between the ICE subunits and that constitute the accessory binding site moiety.

FIGS. 5A–5RRRR lists the atomic structure coordinates for ICE as derived by X-ray diffraction from a crystal of ICE complexed to a tetrapeptide inhibitor.

Figure 2:
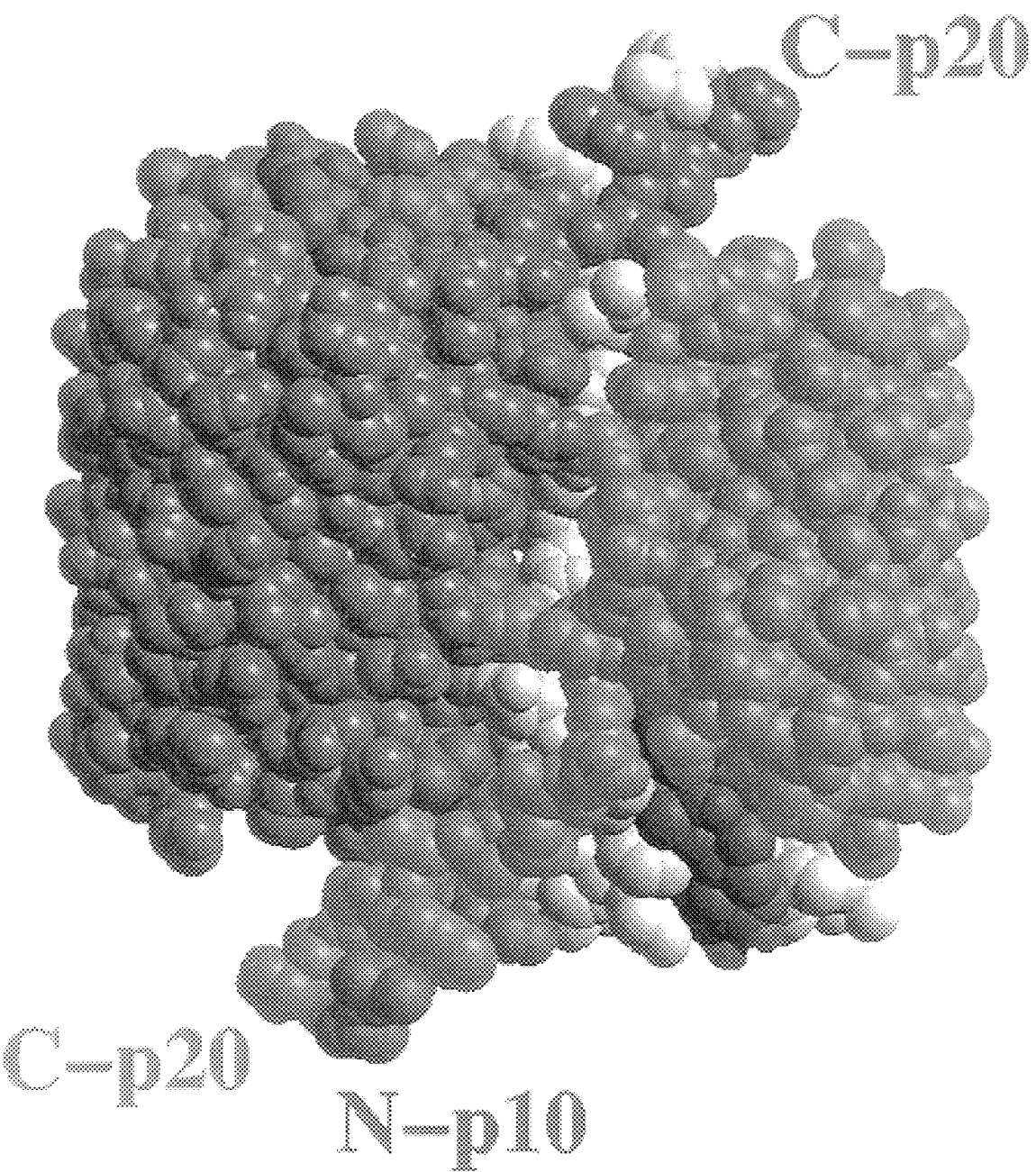
FIG. 2 represents a space-filling model of the $(p20)_2/(p10)_2$ tetramer of interleukin-1β converting enzyme. Two p20 subunits (green,blue) are in contact with two p10 subunits (red,yellow). Magenta coloring on top left and bottom right represents a tetrapeptide aldehyde inhibitor bound in each of the two active sites of the tetramer. The crystallographic two-fold axis is approximately perpendicular to the plane of drawing, and runs through the small hole at the center of the interface between the two p10 subunits. The N-and C-terminal ends of each subunit are labeled.

The following abbreviations are used in FIGS. 5A–5RRRR.

"Atom type" refers to the element whose coordinates are measured. The first letter in the column defines the element.

"X, Y, Z" crystallographically define the atomic position of the element measured.

"B" is a thermal factor that measures movement of the atom around its atomic center.

Atoms numbered 153–158 (Lys-146) and 184–189 (Ser-149) were modeled as Ala residues.

Atoms numbered 1487–1534 and designated "Ald" in the column titled "Residue" are Cys-285 bound to the tetrapeptide aldehyde inhibitor.

Structure coordinates for ICE according to FIGS. 5A–5RRRR may be modified from this original set by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates, and any combination of the above.

ABBREVIATIONS AND DEFINITIONS

ABBREVIATIONS

Amino Acids
A=Ala=Alanine
V=Val=Valine
L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Asn=Asparagine
Q=Gln=Glutamine
D=Asp=Aspartic Acid
E=Glu=Glutamic Acid
K=Lys=Lysine
R=Arg=Arginine
H=His=Histidine

DEFINITIONS

The following terms are also used herein:

The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Unless specifically indicated, all amino acids referred to in this application are in the L-form.

The term "unnatural amino acids" means amino acids that are not naturally found in proteins. Examples of unnatural amino acids used herein, include racemic mixtures of selenocysteine and selenomethionine. In addition, unnatural amino acids include the D or L forms of nor-leucine, para-nitrophenylalanine, homophenylalanine, para-fluorophenylalanine, 3-amino-p2-benzylpropionic acid, homoarginine, and D-phenylalanine.

The term "positively charged amino acid" includes any naturally occurring or unnatural amino acid having a positively charged side chain under normal physiological conditions. Examples of positively charged naturally occurring amino acids are arginine, lysine and histidine.

The term "negatively charged amino acid" includes any naturally occurring or unnatural amino acid having a negatively charged side chain under normal physiological conditions. Examples of negatively charged naturally occurring amino acids are aspartic acid and glutamic acid.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

The term "mutant" refers to an ICE polypeptide, i.e. a polypeptide displaying the biological activity of wild-type, human ICE, characterized by the replacement of at least one amino acid from the wild-type, human ICE sequence according to Thornberry, N. A. et al., *Nature*, 356, pp. 768–774 (1992). Such a mutant may be prepared, for example, by expression of ICE cDNA previously altered in its coding sequence by oligonucleotide-directed mutagenesis.

ICE mutants may also be generated by site-specific incorporation of unnatural amino acids into ICE proteins using the general biosynthetic method of Noren, C. J., et al., *Science*, 244, pp. 182–188 (1989). In this method, the codon encoding the amino acid of interest in wild-type ICE is replaced by a "blank" nonsense codon, TAG, using oligonucleotide-directed mutagenesis (described in detail, infra). A suppressor tRNA directed against this codon is then chemically aminoacylated in vitro with the desired unnatural amino acid. The aminoacylated tRNA is then added to an in vitro translation system to yield a mutant ICE enzyme with the site-specific incorporated unnatural amino acid.

Selenocysteine or selenomethionine may be incorporated into wild-type or mutant ICE by expression of ICE-encoding cDNAs in auxotrophic *E. coli* strains. Hendrickson, W. A. et al., *EMBO J.*, 9(5), pp. 1665–1672 (1990). In this method, the wild-type or mutagenized ICE CDNA may be expressed in a host organism on a growth medium depleted of either natural cysteine or methionine (or both) but enriched in selenocysteine or selenomethionine (or both).

The term "altered surface charge" means a change in one or more of the charge units of a mutant polypeptide, at physiological pH, as compared to wild-type ICE. This is preferably achieved by mutation of at least one amino acid of wild-type ICE to an amino acid comprising a side chain with a different charge at physiological pH than the original wild-type side chain.

The change in surface charge is determined by measuring the isoelectric point (pI) of the polypeptide molecule containing the substituted amino acid and comparing it to the isoelectric point of the wild-type ICE molecule.

The term "high specific activity" refers to a specific activity of ICE where the second order rate constant ($k_{cat}/K_m$) for hydrolysis of the substrate Ac-Tyr-Val-Ala-Asp-aminomethylcoumarin exceeds $7 \times 10^4$ $M^{-1}s^{-1}$ at 25° C., using the assay described by Pennington, M. W. and N. A. Thornberry, *Peptide Res.*, 7(2), pp. 72–76 (1994). Alternatively, the specific activity of ICE may be determined by monitoring hydrolysis of the substrate Ac-Tyr-Val-Ala-Asp-p-nitroaniline. Reiter, L. A., *Intr. J. Peptide Protein Res.*, 43, pp. 8796 (1994).

The term "altered substrate specificity" refers to a change in the ability of a mutant ICE to cleave a substrate as compared to wild-type ICE. Substrate specificity may be measured by hydrolysis of fluorogenic peptide substrates or of unmodified peptide substrates by ICE, as described in Thornberry et al., supra. ICE mutants with altered substrate specificity demonstrate a second order rate constant ($k_{cat}/K_m$) for a substrate $X_1$-Tyr-Val-Ala-$X_2$-$X_3$ that exceeds the $k_{cat}/K_m$ for the analogous peptide substrate $X_1$-Tyr-Val-Ala-Asp-$X_3$. For both substrates, $X_1$ is an amino protecting group, such as acetyl; $X_2$ is a natural or unnatural amino acid residue other than L-aspartate; and $X_3$ is a carboxyl protecting group, such as aminomethylcoumarin or p-nitroaniline.

The "kinetic form" of ICE refers to the condition of the enzyme in its free or unbound form or bound to a chemical entity at either its active site or accessory binding site.

A "competitive" inhibitor is one that inhibits ICE activity by binding to the same kinetic form, of ICE, as its substrate binds—thus directly competing with the substrate for the active site of ICE. Competitive inhibition can be reversed completely by increasing the substrate concentration.

An "uncompetitive" inhibitor is one that inhibits ICE by binding to a different kinetic form of the enzyme than does the substrate. Such inhibitors bind to ICE already bound with the substrate and not to the free enzyme. Uncompetitive inhibition cannot be reversed completely by increasing the substrate concentration.

A "non-competitive" inhibitor is one that can bind to either the free or substrate bound form of ICE.

Those of skill in the art may identify inhibitors as competitive, uncompetitive or non-competitive, by computer fitting enzyme kinetic data using standard equations according to Segel, I. H., *Enzyme Kinetics*, J. Wiley & Sons, (1975). It should also be understood that uncompetitive or non-competitive inhibitors according to this invention may bind to the accessory binding site.

The term "homologue" means a protein having at least 30% amino acid sequence identity with ICE or any functional domain of ICE as defined by Thornberry et al., supra and Casano et al., supra.

The term "subunit dissociation" refers to the fact that at very high dilutions of wild-type ICE, or at concentrations of the enzyme below 10 nM, enzymatic activity shows a time dependent loss assayed in the presence of a tetrapeptide substrate. Reconcentration of the dilute, inactive mixture results in complete recovery of ICE activity. Wild-type ICE demonstrates a Kd for subunit dissociation between 1 and 10 nM. Enzymatic activity is determined by measuring the activity of ICE according to the assay of Penninaton and Thornberry, supra, at varying concentrations of the enzyme. The concentration of the enzyme is determined by active site titration.

The term "co-complex" means ICE or a mutant or homologue of ICE in covalent or non-covalent association with a chemical entity or compound.

The term "associating with" refers to a condition of proximity between a chemical entity or compound, or portions thereof, and an ICE molecule or portions thereof. The association may be non-covalent—wherein the juxtaposition is energetically favored by hydrogen bonding or van der Waals or electrostatic interactions—or it may be covalent.

The term "β-sheet" refers to the conformation of a polypeptide chain stretched into an extended zig-zig conformation. Portions of polypeptide chains that run "parallel" all run in the same direction. Polypeptide chains that are "antiparallel" run in the opposite direction from the parallel chains.

The term "active site" or "active site moiety" refers to any or all of the following sites in ICE: the substrate binding site; the site where the tetrapeptide inhibitor binds and the site where the cleavage of a substrate occurs. The active site is characterized by at least amino acid residues 173, 176, 177, 178, 179, 180, 236, 237, 238, 239, 244, 248, 283, 284, 285, 290, 338, 339, 340, 341, 342, 343, 344, 345, 348, 352, 381 and 383, using the sequence and numbering according to Thornberry et al., supra (SEQ ID No: 1).

The term "accessory binding site" or "accessory binding site moiety" refers to a binding site of ICE comprising amino acid residues adjacent to the two-fold axis of ICE but external to the active site, according to FIGS. 4A and 4B. An accessory binding site may be a locus of ICE inhibition, although it is not the site of substrate cleavage.

The accessory binding site is characterized by at least amino acid residues 150, 151, 240, 259, 267, 268, 274, 291, 292, 293, 294, 295, 296, 297, 317, 318, 319, 320, 321, 322, 323, 324, 325, 327, 334, 335, 367, 371, 374, 375, 377, 378, 380, 382, 384, 386, 388, 389, 390, 391, 392, 393, 394, 395 and 396, using the sequence and numbering according to Thornberry et al., supra (SEQ ID No: 1).

The term "P binding pocket" refers to a binding subsite, or portion of the binding site on the ICE molecule. The amino acid residues of an ICE substrate are given designations according to their position relative to the scissile bond, i.e. the bond that is broken by the protease. Residues are designated P1, P2, etc., for those extending toward the N-terminus from the scissile bond of the substrate. The residues are designated P1', P2', etc., for those extending toward the C-terminus from the scissile bond of the substrate.

The portions of an ICE inhibitor that correspond to the P or P' residues of the substrate are also labeled P1, P1', etc., by analogy with the substrate. The binding subsites of the ICE molecule that receive the residues labeled P1, P1', etc., are designated "the S1 site""the P1' binding pocket"etc. Schechter, I. and A. Berger, "On the Size of the Active Site in Proteases", *Biochem. Biophys. Res. Commun.*, 27, pp. 157–162 (1967).

The "P1 binding pocket" of the ICE active site is defined as the space surrounded by amino acid residues Arg-179, His-237, Gln-283 and Arg-341.

The "P2 binding pocket" of the ICE active site is defined as the space surrounded by amino acid residues Pro-290, Val-338 and Trp-340.

The "P3 binding pocket" of the ICE active site is defined as the space surrounded by amino acid residues Pro-177, Arg-178, Thr-180, Arg-341 and Pro-343.

The "P4 binding socket" of the ICE active site is defined as the space surrounded by amino acid residues Trp-340, His-342, Met-345, Val-348, Arg-352, Asp-381 and Arg-383.

The "P' binding pocket" of the ICE active site is defined as the space surrounded by amino acid residues Phe-173, Ile-176, His-237, Gly-238, Ile-239, Cys-244 and His-248.

The term "p10 subunits interacting across the two-fold axis" means having at least 50% of the interface contacts according to FIGS. 4A and 4B.

The term "structure coordinates" refers to mathematical coordinates derived from mathematical equations related to the patterns obtained on diffraction of a monochromatic beam of X-rays by the atoms (scattering centers) of an ICE molecule in crystal form. The diffraction data are used to calculate an electron density map of the repeating unit of the crystal. The electron density maps are used to establish the positions of the individual atoms within the unit cell of the crystal.

The term "heavy atom derivatization" refers to the method of producing a chemically modified form of a crystal of ICE. In practice, a crystal is soaked in a solution containing heavy metal atom salts, or organometallic compounds, e.g., lead chloride, gold thiomalate, thimerosal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the enzyme. Blundel, T. L. and N. L. Johnson, *Protein Crystallography*, Academic Press (1976).

Those of skill in the art understand that a set of structure coordinates determined by X-ray crystallography is not without standard error. For the purpose of this invention, any set of structure coordinates for ICE or ICE homologues or ICE mutants that have a root mean square deviation of protein backbone atoms (N, Cα, C and O) of less than 0.75 Å when superimposed—using backbone atoms—on the structure coordinates listed in FIGS 5A–5RRRR shall be considered identical.

The term "unit cell" refers to a basic parallelipiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal.

The term "molecular replacement" refers to a method that involves generating a preliminary model of an ICE crystal whose structure coordinates are unknown, by orienting and positioning a molecule whose structure coordinates are known (e.g., ICE coordinates from FIGS. 5A–5RRRR within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, E., "Use of the Rotation and Translation Functions", in *Methods in Enzymology*, 115, pp. 55–77 (1985); M. G. Rossmann, ed., "The Molecular Replacement Method", *Int. Sci. Rev. Ser.*, No. 13, Gordon & Breach, New York, (1972). Using the structure coordinates of ICE provided by this invention, molecular replacement may be used to determine the structure coordinates of a crystalline mutant or homologue of ICE or of a different crystal form of ICE.

DETAILED DESCRIPTION OF THE INVENTION

In order that the invention described herein may be more fully understood, the following detailed description is set forth.

The present invention relates to crystalline interleukin-1β converting enzyme ("ICE"), the structure of ICE as determined by X-ray crystallography, the use of that structure to solve the structure of ICE homologues and of other crystal forms of ICE, mutants and co-complexes of ICE, and the use of the ICE structure and that of its homologues, mutants and co-complexes to design inhibitors of ICE.

A. The Structure of ICE

The present invention provides, for the first time, crystals of human ICE grown in the presence of a tetrapeptide inhibitor from solutions of polyethylene glycol, as well as the structure of ICE as determined therefrom. The crystals have tetragonal space group symmetry $P4_32_12$. The unit cell of said crystals has a rectangular shape of dimensions a=b=65±5 Å, and c=162±5 Å. The structure coordinates of ICE, as determined by X-ray crystallography of crystalline ICE, are listed in FIGS. 5A–5RRRR.

Crystal packing reveals that ICE is a $(p20)_2/(p10)_2$ tetramer. In the tetramer, two p20 subunits contact two adjacent p10 subunits which interact across the crystallographic two-fold axis (FIG. 2). This axis corresponds to an oligomer interface in solution. Most of the dimer-dimer interface consists of p20 residues 291–297 and of p10 residues 318–322 and 386–396.

FIG. 1 represents a ribbon drawing of the p20/p10 ICE heterodimer. As depicted in the figure, the p20 and p10 subunits are intimately associated and the active site is at the top of the figure, roughly at the center of the cluster of displayed side chains.

The enzyme core is a six-stranded β-sheet with 5 parallel strands (numbered 1, 2, 3, 4 and 7) and one anti-parallel strand (numbered 8). Six α-helices (lettered A, B, C, D, E and F) lie roughly parallel to the β-strands. The last seven residues of p20 and the first seven of p10 protrude from this compact structure and form two anti-parallel β-strands [5 (residues 291–297)] and 6 (residues 317–323)]. A few key residues are labelled according to their position in the p45 amino acid sequence of ICE (Thornberry et al., supra).

Our understanding of the structure of ICE has enabled, for the first time, identification of the active site and accessory binding site of the enzyme. The p10 subunit from one ICE molecule contacts the p20 subunit from a different molecule and together they create an active site. The active site spans both the p20 and p10 subunits and comprises amino acid residues from both subunits. The active site moiety is characterized by at least amino acid residues 173, 176, 177, 178, 179, 180, 236, 237, 238, 239, 244, 248, 283, 284, 285, 290, 338, 339, 340, 341, 342, 343, 344, 345, 348, 352, 381 and 383 using the sequence numbering according to Thornberry et al., supra (SEQ ID No: 1).

An accessory binding site is formed by amino acid residues on the p10 subunits that interact across the two-fold axis. The accessory binding site moiety is characterized by at least amino acid residues 150, 151, 240, 259, 267, 268, 274, 291, 292, 293, 294, 295, 296, 297, 317, 318, 319, 320, 321, 322, 323, 324, 325, 327, 334, 335, 367, 371, 374, 375, 377, 378, 378, 380, 382, 384, 386, 388, 389, 390, 391, 392, 393, 394, 395 and 396 using the sequence numbering according to Thornberry et al., supra (SEQ ID No: 1).

B. Uses of the Structure Coordinates of ICE

For the first time, the present invention permits the use of molecular design techniques to design, select and synthesize chemical entities and compounds, including inhibitory compounds, capable of binding to the active site or accessory binding site of ICE, in whole or in part.

On approach enabled by this invention, is to use the structure coordinates of ICE to design compounds that bind to the enzyme and alter the physical properties of the compounds in different ways, e.g., solubility. For example, this invention enables the design of compounds that act as competitive inhibitors of the ICE enzyme by binding to, all or a portion of, the active site of ICE. This invention also enables the design of compounds that act as uncompetitive inhibitors of the ICE enzyme. These inhibitors may bind to, all or a portion of, the accessory binding site of an ICE already bound to its substrate and may be more potent and less non-specific than known competitive inhibitors that compete only for the ICE active site. Similarly, non-competitive inhibitors that bind to and inhibit ICE whether or not it is bound to another chemical entity may be designed using the structure coordinates of ICE of this invention.

A second design approach is to probe an ICE crystal with molecules composed of a variety of different chemical entities to determine optimal sites for interaction between candidate ICE inhibitors and the enzyme. For example, high resolution X-ray diffraction data collected from crystals saturated with solvent allows the determination of where eachtype of solvent molecule sticks. Small molecules that bind tightly to those sites can then be designed and synthesized and tested for their ICE inhibitor activity. Travis, J., *Science*, 262, p. 1374 (1993).

This invention also enables the development of compounds that can isomerize to short-lived reaction intermediates in the chemical reaction of a substrate or other compound that binds to ICE, with ICE. Thus, the time-dependent analysis of structural changes in ICE during its interaction with other molecules is enabled. The reaction intermediates of ICE can also be deduced from the reaction product in co-complex with ICE. Such information is useful to design improved analogues of known ICE inhibitors or to design novel classes of inhibitors based on the reaction intermediates of the ICE enzyme and ICE-inhibitor co-complex. This provides a novel route for designing ICE inhibitors with both high specificity and stability.

Another approach made possible and enabled by this invention, is to screen computationally small molecule data bases for chemical entities or compounds that can bind in whole, or in part, to the ICE enzyme. In this screening, the quality of fit of such entities or compounds to the binding site may be judged either by shape complementarity or by estimated interaction energy. Meng, E. C. et al., *J. Coma. Chem.*, 13, pp. 505–524 (1992).

Because ICE may crystallize in more than one crystal form, the structure coordinates of ICE, or portions thereof, as provided by this invention are particularly useful to solve the structure of those other crystal forms of ICE. They may also be used to solve the structure of ICE mutants, ICE co-complexes, or of the crystalline form of any other protein with significant amino acid sequence homology to any functional domain of ICE.

One method that may be employed for this purpose is molecular replacement. In this method, the unknown crystal structure, whether it is another crystal form of ICE, an ICE mutant, or an ICE co-complex, or the crystal of some other protein with significant amino acid sequence homology to any functional domain of ICE, may be determined using the ICE structure coordinates of this invention as provided in FIGS. 5A–5RRRR. This method will provide an accurate structural form for the unknown crystal more quickly and efficiently than attempting to determine such information ab initio.

In addition, in accordance with this invention, ICE mutants may be crystallized in co-complex with known ICE inhibitors. The crystal structures of a series of such complexes may then be solved by molecular replacement and compared with that of wild-type ICE. Potential sites for modification within the various binding sites of the enzyme may thus be identified. This information provides an additional tool for determining the most efficient binding interactions, for example, increased hydrophobic interactions, between ICE and a chemical entity or compound.

All of the complexes referred to above may be studied using well-known X-ray diffraction techniques and may be refined versus 2-3 Å resolution X-ray date to an R value of about 0.20 or less using computer software, such as X-PLOR (Yale University, ©1992, distributed by Molecular Simulations, Inc.). See, e.g., Blundel & Johnson, supra; *Methods in Enzvmoloav*, vol. 114 & 115, H. W. Wyckoff et al., eds., Academic Press (1985). This information may thus be used to optimize known classes of ICE inhibitors, and more importantly, to design and synthesize novel classes of ICE inhibitors.

The structure coordinates of ICE mutants provided in this invention also facilitate the identification of related proteins or enzymes analogous to ICE in function, structure or both, thereby further leading to novel therapeutic modes for treating or preventing IL-1 mediated diseases.

The design of compounds that bind to or inhibit ICE according to this invention generally involves consideration of two factors. First, the compound must be capable of physically and structurally associating with ICE. Non-covalent molecular interactions important in the association of ICE with its substrate include hydrogen bonding, van der Waals and hydrophobic interactions.

Second, the compound must be able to assume a conformation that allows it to associate with ICE. Although certain portions of the compound will not directly participate in this association with ICE, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of ICE, or the spacing between functional groups of a compound comprising several chemical entities that directly interact with ICE.

The potential inhibitory or binding effect of a chemical compound on ICE may be analyzed prior to its actual synthesis and testing by the use of computer modelling techniques. If the theoretical structure of the given compound suggests insufficient interaction and association between it and ICE, synthesis and testing of the compound is obviated. However, if computer modelling indicates a strong interaction, the molecule may then be synthesized and tested for its ability to bind to ICE and inhibit using the fluorescent substrate assay of Thornberry et al., supra. In this manner, synthesis of inoperative compounds may be avoided.

An inhibitory or other binding compound of ICE may be computationally evaluated and designed by means of a series of steps in which chemical entities or fragments are screened and selected for their ability to associate with the individual binding pockets or other areas of ICE.

One skilled in the art may use one of several methods to screen chemical entities or fragments for their ability to associate with ICE and more particularly with the individual binding pockets of the ICE active site or accessory binding site. This process may begin by visual inspection of, for example, the active site on the computer screen based on the ICE coordinates in FIGS. 5A–5RRRR. Selected fragments or chemical entities may then be positioned in a variety of orientations, or docked, within an individual binding pocket of ICE as defined supra. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:
1. GRID (Goodford, P. J., "A Computational Procedure for Determining Energetically Favorable Binding Sites on Biologically Important Macromolecules" *J. Med. Chem.*, 28, pp. 849–857 (1985)). GRID is available from Oxford University, Oxford, UK.
2. MCSS (Miranker, A. and M. Karplus, "Functionality Maps of Binding Sites: A Multiple Copy Simultaneous Search Method." *Proteins: Structure, Function and Genetics*, 11, pp. 29–34 (1991)). MCSS is available from Molecular Simulations, Burlington, Mass.
3. AUTODOCK (Goodsell, D. S. and A. J. Olsen, "Automated Docking of Substrates to Proteins by Simulated Annealing" *Proteins: Structure. Function, and Genetics*, 8, pp. 195–202 (1990)).
AUTODOCK is available from Scripps Research Institute, La Jolla, Calif.
4. DOCK (Kuntz, I. D. et al., "A Geometric Approach to Macromolecule-Ligand Interactions" *J. Mol. Biol.*, 161, pp. 269–288 (1982)). DOCK is available from University of California, San Francisco, Calif.

Once suitable chemical entities or fragments have been selected, they can be assembled into a single compound or inhibitor. Assembly may be proceed by visual inspection of the relationship of the fragments to each other on the three-dimensional image displayed on a computer screen in relation to the structure coordinates of ICE. This would be followed by manual model building using software such as Quanta or Sybyl.

Useful programs to aid one of skill in the art in connecting the individual chemical entities or fragments include:
1. CAVEAT (Bartlett, P. A. et al, "CAVEAT: A Program to Facilitate the Structure-Derived Design of Biologically Active Molecules". In *Molecular Recognition in Chemical and Biological Problems*", Special Pub., Royal Chem. Soc., 78, pp. 182–196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", *J. Med. Chem.*, 35, pp. 2145–2154 (1992)).
3. HOOK (available from Molecular Simulations, Burlington, Mass.).

Instead of proceeding to build an ICE inhibitor in a step-wise fashion one fragment or chemical entity at a time as described above, inhibitory or other ICE binding compounds may be designed as a whole or "de novo" using either an empty active site or optionally including some portion(s) of a known inhibitor(s). These methods include:
1. LUDI (Bohm, H.-J., "The Computer Program LUDI: A New Method for the De Novo Design of Enzyme Inhibitors", *J. ComR. Aid. Molec. Design*, 6, pp. 61–78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St. Louis, Mo.).

Other molecular modelling techniques may also be employed in accordance with this invention. See, e.g., Cohen, N. C. et al., "Molecular Modeling Software and Methods for Medicinal Chemistry, *J. Med. Chem.*, 33, pp. 883–894 (1990). See also, Navia, M. A. and M. A. Murcko, "The Use of Structural Information in Drug Design", *Current Opinions in Structural Biology*, 2, pp. 202–210 (1992).

Once a compound has been designed or selected by the above methods, the efficiency with which that compound may bind to ICE may be tested and optimized by computational evaluation. For example, a compound that has been designed or selected to function as an ICE-inhibitor must also preferably traverse a volume not overlapping that occupied by the active site when it is bound to the native substrate. An effective ICE inhibitor must preferably demonstrate a relatively small difference in energy between its bound and free states (i.e., a small deformation energy of binding). Thus, the most efficient ICE inhibitors should preferably be designed with a deformation energy of binding of not greater than about 10 kcal/mole, preferably, not greater than 7 kcal/mole. ICE inhibitors may interact with the enzyme in more than one conformation that is similar in overall binding energy. In those cases, the deformation energy of binding is taken to be the difference between the energy of the free compound and the average energy of the conformations observed when the inhibitor binds to the enzyme.

A compound designed or selected as binding to ICE may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the inhibitor and the enzyme when the inhibitor is bound to ICE, preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A.

Kollman, University of California at San Francisco, ©1994]; QUANTA/CHARMM [Molecular Simulations, Inc., Burlington, Mass. ©1994]; and Insight II/Discover (Biosysm Technologies Inc., San Diego, Calif. ©1994). These programs may be implemented, for instance, using a Silicon Graphics workstation, IRIS 4D/35 or IBM RISC/6000 workstation model 550. Other hardware systems and software packages will be known to those skilled in the art.

Once an ICE-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to ICE by the same computer methods described in detail, above.

C. Mutants Of ICE

The present invention also enables mutants of ICE and the solving of their crystal structure. More particularly, by virtue of the present invention, the location of the active site, accessory binding site and interface of ICE based on its crystal structure permits the identification of desirable sites for mutation.

For example, mutation may be directed to a particular site or combination of sites of wild-type ICE, i.e., the accessory binding site or only the active site, or a location on the interface site may be chosen for mutagenesis. Similarly, only a location on, at or near the enzyme surface may be replaced, resulting in an altered surface charge of one or more charge units, as compared to the wild-type enzyme. Alternatively, an amino acid residue in ICE may be chosen for replacement based on its hydrophilic or hydrophobic characteristics.

Such mutants may be characterized by any one of several different properties as compared with wild-type ICE. For example, such mutants may have altered surface charge of one or more charge units, or have an increased stability to subunit dissociation. Or such mutants may have an altered substrate specificity in comparison with, or a higher specific activity than, wild-type ICE.

The mutants of ICE prepared by this invention may be prepared in a number of ways. For example, the wild-type sequence of ICE may be mutated in those sites identified using this invention as desirable for mutation, by means of oligonucleotide-directed mutagenesis or other conventional methods, e.g. deletion. Alternatively, mutants of ICE may be generated by the site specific replacement of a particular amino acid with an unnaturally occurring amino acid. In addition, ICE mutants may be generated through replacement of an amino acid residue, or a particular cysteine or methionine residue, with selenocysteine or selenomethionine. This may be achieved by growing a host organism capable of expressing either the wild-type or mutant polypeptide on a growth medium depleted of either natural cysteine or methionine (or both) but enriched in selenocysteine or selenomethionine (or both).

Mutations may be introduced into a DNA sequence coding for ICE using synthetic oligonucleotides. These oligonucleotides contain nucleotide sequences flanking the desired mutation sites. Mutations may be generated in the full-length DNA sequence of ICE (p45) or in any sequence coding for p30, or p20 or p10 polypeptides.

According to this invention, a mutated ICE DNA sequence produced by the methods described above, or any alternative methods known in the art, can be expressed using an expression vector. An expression vector, as is well known in the art, typically includes elements that permit autonomous replication in a host cell independent of the host genome, and one or more phenotypic markers for selection purposes. Either prior to or after insertion of the DNA sequences surrounding the desired ICE mutant coding sequence, an expression vector also will include control sequences encoding a promoter, operator, ribosome binding site, translation initiation signal, and, optionally, a repressor gene or various activator genes and a signal for termination. In some embodiments, where secretion of the produced mutant is desired, nucleotides encoding a "signal sequence" may be inserted prior to the ICE mutant coding sequence. For expression under the direction of the control sequences, a desired DNA sequence must be operatively linked to the control sequences—i.e., they must have an appropriate start signal in front of the DNA sequence encoding the ICE mutant and maintaining the correct reading frame to permit expression of that sequence under the control of the control sequences and production of the desired product encoded by that ICE sequence.

Any of a wide variety of well known available expression vectors are useful to express the mutated ICE coding sequences of this invention.

These include for example, vectors consisting of segments of chromosomal, non-chromosomal and synthetic DNA sequences, such as various known derivatives of SV40, known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single stranded DNA phages, yeast plasmids such as the 2μ plasmid or derivatives thereof, and vectors derived from combinations of plasmids and phage DNAS, such as plasmids which have been modified to employ phage DNA or other expression control sequences. In the preferred embodiments of this invention, we employ *E. coli* vectors.

In addition, any of a wide variety of expression control sequences—sequences that control the expression of a DNA sequence when operatively linked to it—may be used in these vectors to express the mutated DNA sequences according to this invention. Such useful expression control sequences, include, for example, the early and late promoters of SV40 for animal cells, the lac system, the trp system the TAC or TRC system, the major operator and promoter regions of phage λ the control regions of fd coat protein, all for *E. coli*, the promoter for 3-phosphoglycerate kinase or other glycolytic enzymes, the promoters of acid phosphatase, e.g., Pho5, the promoters of the yeast α-mating factors for yeast, and other sequences known to control the expression of genes of prokaryotic or eukaryotic cells or their viruses, and various combinations thereof. In the preferred embodiments of this invention, we employ either *E. coli* or eukaryotic expression in COS-1 cells, a monkey kidney cell line.

A wide variety of hosts are also useful for producing mutated ICE according to this invention. These hosts include, for example, bacteria, such as *E. coli*, Bacillus and Streptomvces, fungi, such as yeasts, and animal cells, such as CHO and COS-1 cells, plant cells and transgenic host cells. In preferred embodiments of this invention, the host cells are *E. coli* or COS-1 cells.

It should be understood that not all expression vectors and expression systems function in the same way to express mutated DNA sequences of this invention and to produce modified ICE or ICE mutants. Neither do all hosts function equally well with the same expression system. However, one of skill in the art may make a selection among these vectors, expression control sequences and hosts without undue experimentation and without departing from the scope of this invention. For example, an important consideration in selecting a vector, will be the ability of the vector to replicate in a given host. The copy number of the vector, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, its compatibility with the DNA sequence encoding the modified ICE of this invention, particularly with regard to potential secondary structures.

Hosts should be selected by consideration of their compatibility with the chosen vector, the toxicity of the modified ICE to them, their ability to secrete mature products, their ability to fold proteins correctly, and to form tetramers, their fermentation requirements, the ease of the purification of the modified ICE from them and safety. Within these parameters, one of skill in the art may select various vector/expression control system/host combinations that will produce useful amounts of the mutant ICE.

The mutant ICE produced in these systems may be purified by a variety of conventional steps and strategies, including those used to purify wild-type ICE.

Once the ICE mutants have been generated in the desired location, i.e., active site or accessory binding site, the mutants may be tested for any one of several properties of interest.

For example, mutants may be screened for an altered charge at physiological pH. This is determined by measuring the mutant ICE isoelectric point (pI) in comparison with that of the wild-type parent. Isoelectric point may be measured by gel-electrophoresis according to the method of Wellner, D., *Analyt. Chem.*, 43, p. 597 (1971). A mutant with an altered surface charge is an ICE polypeptide containing a replacement amino acid located at the surface of the enzyme, as provided by the structural information of this invention, and an altered pI.

Furthermore, mutants may be screened for high specific activity in relation to the wild-type ICE. A mutant would demonstrate high specific activity if its second order rate constant ($K_{cat}/K_m$) for hydrolysis of the substrate Ac-Tyr-Val-Ala-Asp-amino methylcoumarin exceeds $7 \times 10^4$ $M^{-1}s^{-1}$ at 25° C., using the assay in Penninaton & Thornberry, supra.

A mutant would be tested for altered ICE substrate specificity by measuring the hydrolysis of fluorgenic peptide substrates or unmodified ICE peptide substrates as described in Thornberry et al., supra. An enzyme with altered substrate specificity is an enzyme whose second order rate constant ($k_{cat}/K_m$) for a substrate $X_1$-Tyr-Val-Ala-$X_2$-$X_3$ that exceeds the $k_{cat}/K_m$ for the analogous peptide substrate $X_1$-Tyr-Val-Ala-Asp-$X_3$. $X_1$ is an amino protecting group, such as acetyl; $X_2$ is a natural or unnatural amino acid residue other than L-aspartate; $X_3$ is a carboxyl protecting group such as aminomethylcoumarin or p-nitroaniline.

Further properties of interest also include mutants with increased stability to subunit dissociation. An ICE mutant with increased stability to subunit dissociation would demonstrate no loss of enzymatic activity at concentrations of the enzyme below 10 nM in comparison with the wild-type ICE, which demonstrates a Kd between 1–10 nM.

In order that the invention described herein may be more fully understood, the following examples are set forth. It should be understood that these examples are for illustrative purposes only and are not to be construed as limiting this invention in any manner.

EXAMPLE 1

Crystal Structure of ICE

The cDNA encoding the p30 precursor of active human ICE (residues Asn 120 to His 404 of p45 (Thornberry et al., supra]) was cloned into a $P_L$ promoter expression vector (provided by Dr. J. Mankovich) and expressed in *E. coli* by temperature-shift induction.

Pre-induction repression of the $P_L$ promoter was achieved by co-expression of the cI repressor gene on a co-resident, compatible plasmid (pACYC184cI) in the *E. coli* host, JM109. Yanish-Perron, C., et al., *Gene*, 33, pp. 103–199 (1985; ATCC #53323). The promoter was induced by increasing the temperature from 28° C. to 42° C., at which point the temperature sensitive cI repressor gene product denatures and gene expression is initiated, directed by the $P_L$ promoter. Maintenance of the temperature at 42° C. for a further 4 hours resulted in the accumulation of high levels of the inactive ICE p30 precursor product within the host cell cytoplasm, in the form of inactive inclusion bodies.

After mechanical disruption of the cells, and harvesting of the insoluble fraction, the inclusion bodies were washed by suspension in 2M urea, 25 mM tris, 0.5 mM DTT, 0.1 mM EDTA, 0.1 mM PMSF, pH 7.5 at 4° C., followed by centrifugation. The inclusion bodies were solubilized in the above buffer containing 7M urea, centrifuged and subjected to size-exclusion chromatography in the same buffer. The p30 fractions, identified by SDS-PAGE and N-terminal sequence analysis, were pooled and diluted to 0.3 mg/ml using column buffer. This was followed by dialysis at 4° C. against 25 mM tris, 1 mM DTT, pH 7.5, until the urea concentration was less than 20 mM, thereby allowing the enzyme to refold.

The protein was concentrated to 3–5 mg/ml by ultrafiltration at 4° C., followed by incubation at room temperature. The disappearance of the p30 precursor, and the concomitant appearance of the p20 and p10 subunits, was monitored by SDS-PAGE, evidence that autocatalytic processing of the enzyme had occurred. ICE enzymatic activity was assayed by hydrolysis of a Succinyl-Tyr-Val-Ala-Asp-p-nitroanilide substrate at 37° C. and correlated closely with conversion to subunits.

The autoprocessed ICE was inhibited fully by adding a 2× molar excess of a tetrapeptide aldehyde inhibitor (acetyl-Tyr-Vol-Ala-Asp-H). The protein-inhibitor complex sample was concentrated and fractionated by size-exclusion chromatography, in final preparation for crystallization experiments.

Crystals of ICE in complex with the inhibitor were grown by vapor diffusion. Davies, D. R. and D. M. Segal, *Meth. Enzvmol.*, 22, p. 266 (1971). Protein (20 mg/ml in 50 mM citrate, 2.0 mM DTT, pH 6.5) was mixed with an equal volume of reservoir buffer (15% (w/v) PEG 4K, 400 mM LiSO$_4$, 200 mM sodium Hepes, 5 mM sodium cacodylate, 0.5% beta-octyl glucoside, pH 7.0) and allowed to stand over the reservoir solution at 4° C. Crystals grew over a six week period to form tetragonal bipyramids and were equilibrated with 18% PEG 4K, 400 mM LiSo$_4$, 200 mM sodium Hepes, 5 mM sodium cacodylate, 0.5% beta-octyl glucoside, pH 7.0 prior to data collection or heavy atom derivatization.

Those of skill in the art will appreciate that the aforesaid crystallization conditions can be varied. Such variations may be used alone or in combination, and include final protein/inhibitor complex concentrations between 5 mg/ml and 35 mg/ml; all combinations of ICE/inhibitor to precipitant ratios; citrate concentrations between 1 mM and 200 mM; DTT concentrations between 0 mM and 10 mM; and any concentration of β-mercaptoethanol; pH ranges between 5.5 and 9.5; PEG concentrations between 10% and 25% (gms/100 ml); PEG weights between 2000 and 8000; LiSO$_4$ concentrations between 50 and 750 mM; HEPES concentrations between 5 and 395 mM; and any concentration or type of detergent; any temperature between −50° C. and 30° C.; and crystallization of ICE/inhibitor complexes by batch, liquid bridge, or dialysis method using these conditions or variations thereof.

All X-ray data sets were collected on a R-axis IIC image plate system except for the 2.2 Å Synchrotron data set that was used for refinement of the final model. This data was collected at Cornell High Energy Synchrotron Source ("CHESS") on a charge-couple device and was reduced to structure factor amplitudes using the Denzo Software Package (Denzo—An Oscillation Data Processing Program For Macro Molecular Crystallography, ©1993, Daniel Gewirth, Yale University). Oscillation photographs were integrated and reduced to structure factor amplitudes using software supplied by the manufacturer (Molecular Structures Corp., Dallas, Tex.).

Refined heavy atom parameters were used to compute multiple isomorphous replacement phases. Inclusion of the anomalous data for the Hg derivative in cross-phased difference Fourier maps showed the space group to be P4$_3$2$_1$2 rather than its enantiomorph. The mean figure of merit, including anomalous data for the Hg derivative, was 0.65 to 3.5 Å resolution (Table 1).

Solvent flattening and phase extension (CCP4-Collaborative Computing Project No. 4, A Suite of Programs for Protein Crystallography; Daresbury Laboratory, Warrington, WA4 4AD, U.K. (1979)) improved the map and allowed identification of some of the residues in the protein core. Cycles of model building (Quanta, version 4.0b, Molecular Simulations Inc., Burlington Mass.), positional refinement, (Brunger, A. T., *J. Acta Cryst.*, A46, pp. 46–57 (1990); Brunger, A. T. et al., *J. Acta Cryst.*, A46, pp. 585–93 (1990)) and phase combination (CCP4-Collaborative Computing Project, supra) were carried out until the switch to phases calculated from the model could be made. Refinement continued against the −16° C., 2.2 Å data (Table 1), which allowed the more difficult loop regions of the protein to be constructed.

The following table summarizes the X-ray crystallography data sets of ICE derivatives that were used to determine the structure of ICE according to this invention.

TABLE 1

| Protein Modification | Resolution Å | Completeness of data % | Rmerge % | Unit cell dimensions, Å | | No. of sites | Rc % | Phasing Power |
| --- | --- | --- | --- | --- | --- | --- | --- | --- |
| | | | | a,b | c | | | |
| Tetrapeptide aldehyde* | 20–2.2 | 87 | 7.1 | 64.9 | 164.1 | — | — | — |
| Tetrapeptide aldehyde** | 20–2.6 | 90 | 8.3 | 64.4 | 163.3 | — | — | — |
| Tetrapeptide aldehyde | 20–2.8 | 78 | 8.3 | 64.7 | 162.9 | — | — | — |
| Iodinated tetrapeptide aldehyde | 20–3.5 | 86 | 9.4 | 64.4 | 162.8 | 2 | 0.88 | 1.09 |
| Thimerosal | 20–3.5 | 88 | 8.4 | 64.4 | 162.3 | 5 | 0.67 | 1.08 |
| Gold Thiomalate | 20–3.5 | 74 | 9.5 | 64.7 | 162.7 | 3 | 0.72 | 1.22 |
| Uranyl Acetate | 20–4.0 | 80 | 10.8 | 64.7 | 162.9 | 2 | 0.79 | 1.32 |
| Lead Chloride | 20–3.5 | 64 | 8.9 | 64.7 | 162.8 | 2 | 0.76 | 1.38 |

*Data collected at −16° C. at CHESS
**Data collected at −16° C.

Definitions: Rmerge gives the agreement between repeated intensity measurements, with the number of crystals used in the data set given in parentheses. The number of heavy-atom binding sites is given where appropriate. $R_c$ is the Cullis R factor for centrosymmetric reflections, and the phasing power is the ratio of average heavy-atom scattering to the average lack of closure of the phase triangles. Blundell, T. L. and Johnson, L. N., *Protein Crystallography*, Academic Press, New York (1976).

The ICE tetrameric model according to this invention has an R-factor of 19% against all observed data between 7 Å and 2.2 Å resolution, with root-mean-square deviation from ideal bond lengths and angles of 0.011 Å and 2.84 Å respectively.

EXAMPLE 2

Confirmation of the Active Site of ICE

In order to confirm the location of the active site in the tetrameric ICE molecule, as deduced from the structure coordinates of ICE, a series of p30 ICE mutants was generated.

Oligonucleotide-directed mutagenesis was performed on pcDNA3 (Invitrogen) constructs using uracil-enrichment of single-strand DNA. Kunkel, T. A., *Proc. Nat. Acad. Sci.*, 82, pp. 488–492 (1985); Kunkel, T. A. et al., *Meth. Enzymol.*, 154, pp. 367–382 (1987). This is a modification of the method originally described for M13 mutagenesis. Zoller, M. J. and M. Smith, *Nucleic Acids Res.*, 10, pp. 6487–6500 (1983); Zoller M. J. and M. Smith, *Meth. Enzymol.*, 100, pp. 468–500 (1983).

Mutagenesis was performed using the reagents provided in the Muta-Gene Kit (BioRad). Mutagenesis primers were synthesized in the (+) coding orientation. The dut−una− *E. coli* strain CJ326 was used for uracil enrichment of single-strand DNA, and the MV1190 strain was used for selection of heteroduplex DNA after extension-ligation reactions. All oligonucleotides were synthesized on an applied Biosystems 380 DNA synthesizer and purified by electrophoreses in polyacrylamide-urea slab gels. Mutations made in the 30 kDa ICE-encoding cDNA were fully sequenced in the coding region by the dideoxy method. Sanger, F. et al., *Proc. Nat. Acad. Sci.* 74, pp. 5463–5467 (1977). Mutant DNA in preparation for COS-1 cell transfection, or alternatively *E. coli* transfection, was purified by alkaline lysis and cesium gradient centrifugation prior to transfection.

Each mutant cDNA was transfected into a COS-1 cell line, then tested for its ability to process pIL-1β in vitro, i.e., to secrete mature IL-1β. The COS-1 cell line used, had previously been transfected with a pIL-1β encoding cDNA cloned into an MNC stuffer vector (B. Seed, Harvard Medical School) which had subsequently integrated into the chromosome. pIL-1β production was maintained by the addition of 0.5 mg/ml G-418 Sulfate to culture media.

Approximately $3\times10^6$ COS-1 cells in 100 mm tissue culture plates were transfected with 15 $\mu$g of each plasmid. DNA was mixed with 200 $\mu$l DEAE-Dextran, brought to 4 ml with phosphate-buffered saline, and added to the plates. Cells were incubated at 37° C. for 30 min. 8 ml of an 80 $\mu$M chloroquine/serum-free DMEM solution was added and the cells were incubated for 2.5 hr. This solution was aspirated and cells were treated for two minutes with 10% DMSO/serum-free DMEM. After washing with serum-free media, 10 ml complete media was added. Conditioned media were sampled at 16 and 24 hr. Activity in this assay requires that transcription, translation and protein folding of mutants are not arrested. The amount of mutant ICE present in cell lysates was determined by Western blot using an anti-p20 rabbit antiserum that recognizes amino acids 136–150 inclusive and which also recognizes the intact p30 precursor.

Figure 3:
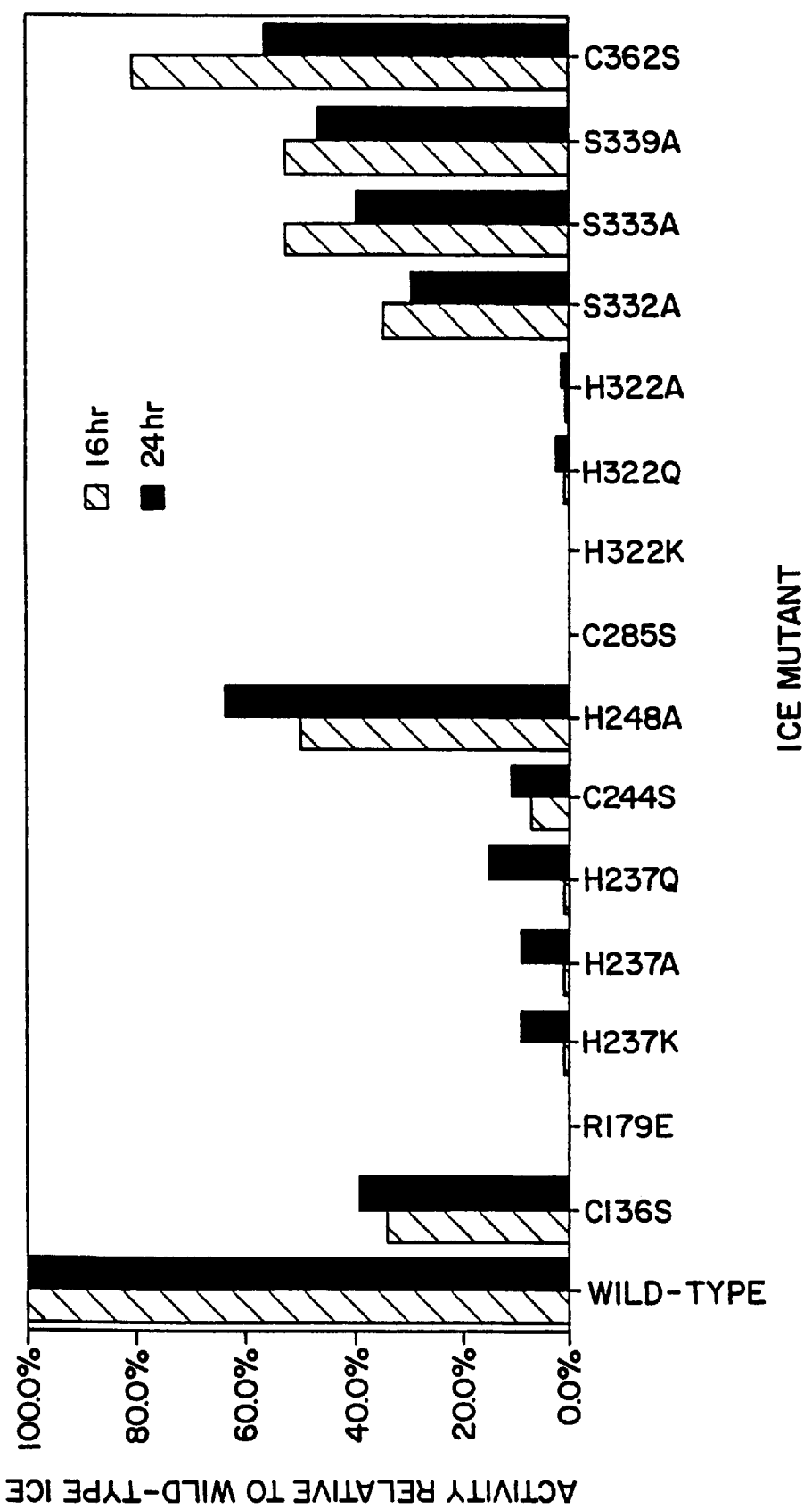
FIG. 3 is a graphic depiction of the activity of various interleukin-1β converting enzyme mutants in processing pIL-1β intracellularly, relative to wild-type interleukin-1β converting enzyme activity. The particular mutants tested are designated on the x-axis using nomenclature listing the specific amino acid and its residue number. For example, "C285S" indicates replacement of amino acid Cys-285 with serine. Activity levels were measured at 16 hours (hatched bar) and 24 hours (solid bars).

Mature IL-1β in the cell medium was detected by ELISA (R&D Systems). Samples were diluted to achieve concentrations in the linear range of the ELISA assay (8–60 pg/ml). Background IL-1β levels were determined in cells transfected with the expression vector lacking ICE cDNA, and this value was subtracted from all other concentrations. The % activity values were calculated as the ratio of secreted IL-1β from cells transfected with mutant ICE divided by IL-1β secreted by cells transfected with wild-type ICE. The final ratio is the mean of at least two experiments. These data are recorded in FIG. 3.

Based on these data, it was determined that mutation of Cys-285 or His-237 eliminates pIL-1β processing activity, as well as autoprocessing. Mutation of Arg-179, which contacts the P1 Asp to Glu, also abolishes activity. Mutation of Cys-244 to Ala, which may contact P' side chains of substrates, reduces enzymatic activity significantly. In contrast, mutation of other residues proximal to Cys-285, including Ser-332, -333 or -339, and His-249, does not eliminate activity. Accordingly, we confirmed the importance of various residues in the ICE active site.

EXAMPLE 3

The Use of Molecular Replacement To Solve An Unknown ICE Crystal Structure

The method of molecular replacement was used to determine the structure coordinates of crystals of ICE in complex with the tetrapeptide aldehyde inhibitor Ac-Tyr-Val-Pro-Asp-H in comparison with crystals of ICE in complex with the tetrapeptide aldehyde inhibitor Ac-Tyr-Val-Ala-Asp-H (as prepared in Example 1). Crystals of ICE in complex with the tetrapeptide aldehyde inhibitor, Ac-Tyr-Val-Pro-Asp-H ("Pro") were grown under conditions identical to those for crystals of ICE in complex with the tetrapeptide aldehyde inhibitor, Ac-Tyr-Val-Ala-Asp-H ("Ala").

X-ray diffraction data to 2.8 Å resolution was collected on the ICE/Pro co-complex. A difference electron density map that combined diffraction data of the form $|F_{pro}-F_{Ala}|$ and phases calculated from the refined model of the Ala inhibited enzyme was used to locate structure changes that had occurred in the ICE/Pro co-complex.

Negative features were found in the map wherever localized atoms in the Ala complex were removed or shifted by switching to the new ligand. Positive features were found when localized atoms were introduced into the structure, and indicated the new positions of shifted atoms.

Replacement of the alanine that sits in the P2 binding pocket in Ala with proline in Pro introduced two methylene groups into the structure of the ICE co-complex. The location of these new atoms was indicated by the presence of positive difference electron density adjacent to the beta-carbon of the alanine in the binding pocket P2. Another positive peak nearby indicated the binding of a new water molecule in the Pro complex relative to the Ala complex. There were also pairs of positive and negative peaks near the tyrosine moiety that sits in the P4 binding pocket of the inhibitor. These peaks indicated shifts in the position of these atoms in the Pro complex relative to their location in the Ala complex.

These shifts, plus the new atoms referred to above, were modeled, and the resulting structure was refined against the X-ray data to determine a final picture of the co-complex of Pro with ICE. The space group ($P4_32_12$) and unit cell dimensions (a=b=65±5 Å c=162±5Å) for the Pro complex were the same as those observed for the-Ala complex.

The ICE structure coordinates known for the first time by virtue of this invention may be used to solve the unknown structure of any mutant, homologue or co-complex of ICE using the above-described method. This method may also be used to determine the binding or orientation of a ligand or chemical entity in the active site or accessory binding site of ICE.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A method for identifying a potential inhibitor of a mutant interleukin-1β converting enzyme, the method comprising the steps of:

a. using a three-dimensional structure of interleukin-1β converting enzyme as defined by atomic coordinates of interleukin-1β converting enzyme according to FIG. 5;

b. replacing one or more interleukin-1β converting enzyme amino acids selected from 150,151,173,176, 177,178,179,180,236,237,238,239,240,244, 248,259, 267,268,274,283,284,285,290,291,292,293,294,295, 296,297,317,318, 319,320,321,322,323,324,325,327, 334,335,338,339,340,341,342,343,345,348, 352,367, 371,374,375,377,378,380,381,382,383,384,386,388, 389,390,391,392, 393,394,395 or 396 of SEQ ID NO;1 in said three-dimensional structure with a different a naturally occuring amino acid;

c. employing said three-dimensional structure to design or select said potential inhibitor;

d. synthesizing said potential inhibitor; and e. contacting said potential inhibitor with said mutant interleukin-1β converting enzyme or said interleuldn-1β converting enzyme in the presence of a substrate to test the ability of said potential inhibitor to inhibit said interleukin-1β converting or said mutant interleukin-1β converting enzyme.

2. The method according to claim 1, wherein said potential is selected from a database.

3. The method according to claim 1, wherein said potential inhibitor is designed de novo.

4. The method according to claim 1, wherein said potential inhibitor is designed from a known inhibitor.

5. The method according to claim 1, wherein said step of employing said three-dimensional structure to design or select said potential inhibitor comprises the steps of:

a. identifying chemical entities or fragments capable of associating with mutant interleukin-1β converting enzyme; and b. assembling the identified chemical entities or fragments into a single molecule to provide the structure of said potential inhibitor.

6. The method according to any one of claims 1 or 3–5, wherein the potential inhibitor is a competitive inhibitor of mutant interleukin-1β converting enzyme.

7. The method according to any one of claims 1 or 3–5, wherein said potential inhibitor is a non-competitive or uncompetitive inhibitor of mutant interleukin-1β converting enzyme.

* * * * *